US010385112B2

(12) United States Patent
Samulski

(10) Patent No.: US 10,385,112 B2
(45) Date of Patent: Aug. 20, 2019

(54) MODIFIED SOLUBLE VEGF RECEPTOR-1 GENES AND VECTORS FOR GENE THERAPY

(71) Applicants: Richard J. Samulski, Chapel Hill, NC (US); ASKLEPIOS BIOPHARMACEUTICAL, INC., Chapel Hill, NC (US)

(72) Inventor: Richard J. Samulski, Chapel Hill, NC (US)

(73) Assignee: ASKLEPIOS BIOPHARMACEUTICAL, INC., Chapel Hill, NC (US)

(*) Notice: Subject to any disclaimer, the term of this patent is extended or adjusted under 35 U.S.C. 154(b) by 0 days.

(21) Appl. No.: 14/770,991

(22) PCT Filed: Mar. 12, 2014

(86) PCT No.: PCT/US2014/024119
§ 371 (c)(1),
(2) Date: Aug. 27, 2015

(87) PCT Pub. No.: WO2014/159546
PCT Pub. Date: Oct. 2, 2014

(65) Prior Publication Data

US 2016/0009786 A1 Jan. 14, 2016

Related U.S. Application Data

(60) Provisional application No. 61/782,450, filed on Mar. 14, 2013.

(51) Int. Cl.

| | |
|---|---|
| ***A61K 48/00*** | (2006.01) |
| ***A61K 31/7088*** | (2006.01) |
| ***A61K 35/76*** | (2015.01) |
| ***C12N 15/864*** | (2006.01) |
| ***C12N 15/12*** | (2006.01) |
| ***C12N 7/01*** | (2006.01) |
| ***C07K 14/71*** | (2006.01) |
| ***C12N 15/86*** | (2006.01) |

(52) U.S. Cl.
CPC .............. *C07K 14/71* (2013.01); *C12N 15/86* (2013.01); *A61K 48/00* (2013.01); *A61K 48/0066* (2013.01); *C12N 2750/14141* (2013.01); *C12N 2750/14143* (2013.01); *C12N 2800/22* (2013.01)

(58) Field of Classification Search
None
See application file for complete search history.

(56) References Cited

U.S. PATENT DOCUMENTS 5,478,745 A 12/1995 Samulski et al.
6,051,698 A 4/2000 Jangic et al.
6,204,059 B1 3/2001 Samulski et al.
6,491,907 B1 12/2002 Rabinowotz et al.
2004/0029106 A1 2/2004 Samulski et al.

FOREIGN PATENT DOCUMENTS

WO WO 2001/58494 8/2001
WO WO2007149852 12/2007

OTHER PUBLICATIONS

Kudla et al, High Guanine and Cytosine Content Increases mRNA Levels in Mammalian Cells, PLOS, 2006, pp. 933-942.*
Verrax et al, Delivery of Soluble VEGF Receptor 1 (sFlt1) by Gene Electrotransfer as a New Antiangiogenic Cancer Therapy, Molecular Pharmaceutics, 2011, pp. 701-708.*
Lai et al, rAAV.sFlt-1 Gene Therapy Achieves Lasting Reversal of Retinal Neovascularization in the Absence of a Strong Immune Response to the Viral Vector, Immunology and Microbiology, 2009, pp. 4279-4287.*
Mingozzi and High, Immune responses to AAV vectors: overcoming barriers to successful gene therapy, Blood, Jul. 4, 2013 x vol. 122, No. 1, pp. 23-36.*
Liu et al, Republished review: Gene therapy for ocular diseases, Postgrad Med J. Jul. 2011 ; 87(1029): 487-495.*
Kudla, Grzegorz et al. "High guanine and cytosine content increases mRNA levels in mammalian cells." PLOS Biology, Public Library of Science, 2006, vol. 4, No. 6, pp. e180-933-e180/942.
Zhao, Kong-Nan et al. "BPV1 E2 Protein Enhances Packaging of Full-Length Plasmid DNA in BPV1 Pseudovirions." Virology, 2000, vol. 272, pp. 382-393.
Ambati, B.K. et al. "Corneal avascularity is due to soluble VEGF receptor-1." *Nature*, 2006, vol. 443, No. 7114, pp. 993-997.
Bainbridge, J.W.B et al. "Inhibition of retinal neovascularization be gene transfer of soluble VEGF receptor sFlt-1." *Gene Therapy*, 2002, vol. 9, pp. 320-326.
Kajigaya, S. et al. "Self-assembled B19 parvovirus capsids, produced in a baculovirus system, are antigenically and immunogenically similar to native virons." *Proc. Natl. Acad. Sci*, 1991, vol. 88, pp. 4646-4650.
Kirnbauer, R. et al. "Virus-like Particles of Bovine Papillomavirus Type 4 in Prophylactic and Therapeutic Immunization." *Virology*, 1996, vol. 219, pp. 37-44.
Lai, C.M. et al. "Long-term evaluation of AAV-mediated sFlt-1 gene therapy for ocular neovascularization in mice and monkeys." *Molecular Therapy*, 2005, vol. 12, No. 4, pp. 659-668.
Ruffing, M. et al. "Assembly of Viruslike Particles by Recombinant Structural Proteins of Adeno-Associated Virus Type 2 in Insect Cells." *Journal of Virology*, 1992, vol. 66, No. 12, pp. 6922-6930.
Samulski, R. et al. "Helper-Free Stocks of Recombinant Adeno-Associated Viruses: Normal Integration Does Not Require Viral Gene Expression." *Journal of Virology*, 1989, vol. 63, No. 9, pp. 3822-3828.

(Continued)

*Primary Examiner* — Maria Marvich
(74) *Attorney, Agent, or Firm* — Tristan A. Fuierer; Marianne Fuierer; Olive Law Group, PLLC

(57) ABSTRACT

The present invention relates to a modified and optimized sFlt1 nucleic acid for inclusion in a virus vector. Use of such vectors can be used for treatment of ocular disorders causing neovascularization, such as macular degeneration.

13 Claims, 32 Drawing Sheets

Specification includes a Sequence Listing.

(56) References Cited

OTHER PUBLICATIONS

Shen, J. et al. "Suppression of ocular neovascularization with siRNA targeting VEGF receptor1." *Gene Therapy*, 2006, vol. 13, No. 3, pp. 225-234.

Xiao, X. et al. "A Novel 165-Base-Pair Terminal Repeat Sequence is the Sole cis Requirement for the Adeno-Associated Virus Life Cycle." *Journal of Virology*, 1997, vol. 71, No. 2, pp. 941-948.

Lebherz, Corinna, et al.; "Novel AAV serotypes for improved ocular gene transfer," J Gene Med, 2008, vol. 10, pp. 375-382.

Surace, Enrico M.; "Versatility of AAV vectors for retinal gene transfer," Vision Research, 2008, vol. 48, pp. 353-359.

Weber, Michel, et al.; "Recombinant Adeno-associated Virus Serotype 4 Mediates Unique and Exclusive Long-Term Transduction of Retinal Pigmented Epithelium in rat, Dog, and Nonhuman Primate after Subretinal Delivery," Molecular Therapy, 2003, vol. 7, pp. 774-781.

* cited by examiner

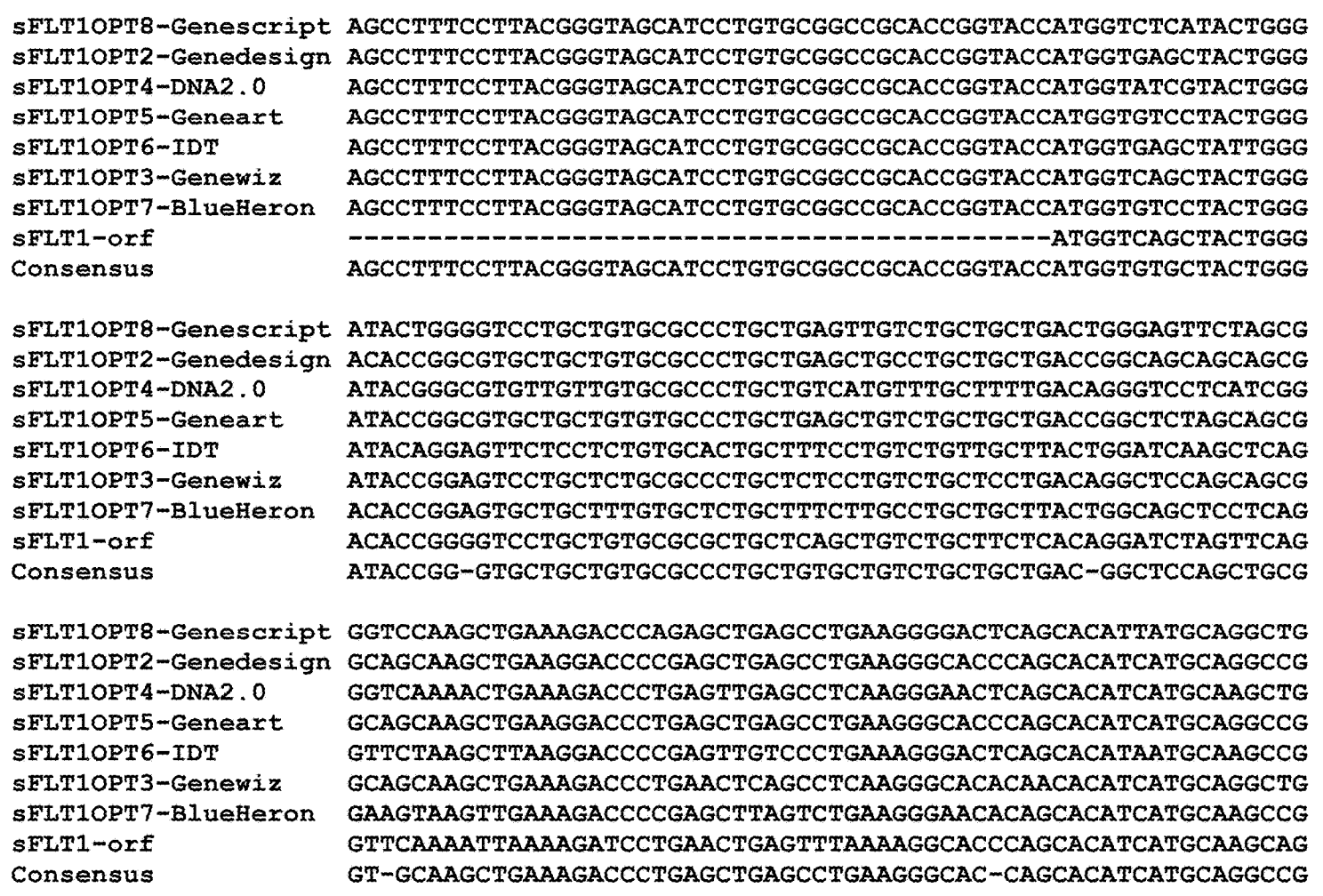

```
sFLT1OPT8-Genescript AGCCTTTCCTTACGGGTAGCATCCTGTGCGGCCGCACCGGTACCATGGTCTCATACTGGG
sFLT1OPT2-Genedesign AGCCTTTCCTTACGGGTAGCATCCTGTGCGGCCGCACCGGTACCATGGTGAGCTACTGGG
sFLT1OPT4-DNA2.0     AGCCTTTCCTTACGGGTAGCATCCTGTGCGGCCGCACCGGTACCATGGTATCGTACTGGG
sFLT1OPT5-Geneart    AGCCTTTCCTTACGGGTAGCATCCTGTGCGGCCGCACCGGTACCATGGTGTCCTACTGGG
sFLT1OPT6-IDT        AGCCTTTCCTTACGGGTAGCATCCTGTGCGGCCGCACCGGTACCATGGTGAGCTATTGGG
sFLT1OPT3-Genewiz    AGCCTTTCCTTACGGGTAGCATCCTGTGCGGCCGCACCGGTACCATGGTCAGCTACTGGG
sFLT1OPT7-BlueHeron  AGCCTTTCCTTACGGGTAGCATCCTGTGCGGCCGCACCGGTACCATGGTGTCCTACTGGG
sFLT1-orf            --------------------------------------------ATGGTCAGCTACTGGG
Consensus            AGCCTTTCCTTACGGGTAGCATCCTGTGCGGCCGCACCGGTACCATGGTGTGCTACTGGG

sFLT1OPT8-Genescript ATACTGGGGTCCTGCTGTGCGCCCTGCTGAGTTGTCTGCTGCTGACTGGGAGTTCTAGCG
sFLT1OPT2-Genedesign ACACCGGCGTGCTGCTGTGCGCCCTGCTGAGCTGCCTGCTGCTGACCGGCAGCAGCAGCG
sFLT1OPT4-DNA2.0     ATACGGGCGTGTTGTTGTGCGCCCTGCTGTCATGTTTGCTTTTGACAGGGTCCTCATCGG
sFLT1OPT5-Geneart    ATACCGGCGTGCTGCTGTGTGCCCTGCTGAGCTGTCTGCTGCTGACCGGCTCTAGCAGCG
sFLT1OPT6-IDT        ATACAGGAGTTCTCCTCTGTGCACTGCTTTCCTGTCTGTTGCTTACTGGATCAAGCTCAG
sFLT1OPT3-Genewiz    ATACCGGAGTCCTGCTCTGCGCCCTGCTCTCCTGTCTGCTCCTGACAGGCTCCAGCAGCG
sFLT1OPT7-BlueHeron  ACACCGGAGTGCTGCTTTGTGCTCTGCTTTCTTGCCTGCTGCTTACTGGCAGCTCCTCAG
sFLT1-orf            ACACCGGGGTCCTGCTGTGCGCGCTGCTCAGCTGTCTGCTTCTCACAGGATCTAGTTCAG
Consensus            ATACCGG-GTGCTGCTGTGCGCCCTGCTGTGCTGTCTGCTGCTGAC-GGCTCCAGCTGCG

sFLT1OPT8-Genescript GGTCCAAGCTGAAAGACCCAGAGCTGAGCCTGAAGGGGACTCAGCACATTATGCAGGCTG
sFLT1OPT2-Genedesign GCAGCAAGCTGAAGGACCCCGAGCTGAGCCTGAAGGGCACCCAGCACATCATGCAGGCCG
sFLT1OPT4-DNA2.0     GGTCAAAACTGAAAGACCCTGAGTTGAGCCTCAAGGGAACTCAGCACATCATGCAAGCTG
sFLT1OPT5-Geneart    GCAGCAAGCTGAAGGACCCTGAGCTGAGCCTGAAGGGCACCCAGCACATCATGCAGGCCG
sFLT1OPT6-IDT        GTTCTAAGCTTAAGGACCCCGAGTTGTCCCTGAAAGGGACTCAGCACATAATGCAAGCCG
sFLT1OPT3-Genewiz    GCAGCAAGCTGAAAGACCCTGAACTCAGCCTCAAGGGCACACAACACATCATGCAGGCTG
sFLT1OPT7-BlueHeron  GAAGTAAGTTGAAAGACCCCGAGCTTAGTCTGAAGGGAACACAGCACATCATGCAAGCCG
sFLT1-orf            GTTCAAAATTAAAAGATCCTGAACTGAGTTTAAAAGGCACCCAGCACATCATGCAAGCAG
Consensus            GT-GCAAGCTGAAAGACCCTGAGCTGAGCCTGAAGGGCAC-CAGCACATCATGCAGGCCG
```

Figure 1

```
sFLT1OPT8-Genescript GACAGACCCTGCACCTCCAGTGCCGAGGAGAGGCAGCTCACAAATGGTCCCTGCCCGAAA
sFLT1OPT2-Genedesign GCCAGACCCTGCACCTGCAGTGCCGCGGCGAGGCCGCCCACAAGTGGAGCCTGCCCGAGA
sFLT1OPT4-DNA2.0     GTCAGACGCTCCATCTGCAGTGTCGGGGAGAAGCTGCCCACAAGTGGAGCCTGCCCGAGA
sFLT1OPT5-Geneart    GCCAGACACTGCATCTGCAGTGCCGGGGAGAAGCCGCCCACAAATGGTCCCTGCCTGAGA
sFLT1OPT6-IDT        GTCAGACTTTGCATCTGCAGTGCAGGGGGGAGGCCGCTCATAAATGGAGCCTTCCCGAGA
sFLT1OPT3-Genewiz    GACAGACCCTCCATCTCCAGTGCAGAGGCGAGGCCGCTCACAAGTGGTCCCTCCCTGAGA
sFLT1OPT7-BlueHeron  GACAGACACTGCATCTCCAGTGCCGAGGCGAGGCAGCTCACAAGTGGTCCCTGCCCGAGA
sFLT1-orf            GCCAGACACTGCATCTCCAATGCAGGGGGGAAGCAGCCCATAAATGGTCTTTGCCTGAAA
Consensus            GC--AGACCTGCATCTGCAGTGCCGGGG-GAGGCCGCTCACAAGTGGTCCCTGCCCGAGA

sFLT1OPT8-Genescript TGGTGTCCAAGGAGTCTGAAAGACTGAGTATCACCAAATCAGCATGCGGCAGGAACGGGA
sFLT1OPT2-Genedesign TGGTGAGCAAGGAGAGCGAGCGCCTGAGCATCACCAAGAGCGCCTGCGGCCGCAACGGCA
sFLT1OPT4-DNA2.0     TGGTGAGCAAAGAGTCGGAGAGACTTTCGATCACGAAATCCGCATGCGGAAGAAATGGGA
sFLT1OPT5-Geneart    TGGTGTCCAAAGAGAGCGAGCGGCTGAGCATCACCAAGAGCGCCTGCGGCAGAAACGGCA
sFLT1OPT6-IDT        TGGTGTCCAAGGAGTCCGAGAGACTGTCAATCACTAAATCAGCTTGTGGCAGGAACGGCA
sFLT1OPT3-Genewiz    TGGTGTCCAAAGAAAGCGAGAGGCTGAGCATCACCAAGAGCGCTTGCGGCAGGAATGGCA
sFLT1OPT7-BlueHeron  TGGTGTCCAAAGAATCTGAGAGGCTCTCAATCACAAAGAGCGCTTGTGGGAGGAACGGCA
sFLT1-orf            TGGTGAGTAAGGAAAGCGAAAGGCTGAGCATAACTAAATCTGCCTGTGGAAGAAATGGCA
Consensus            TGGTGTCCAAGGAGTGCGAGAGGCTGAGCATCACCAAGTGCGC-TGCGGCAGGAACGGCA

sFLT1OPT8-Genescript AGCAGTTCTGTTCCACTCTGACCCTGAACACAGCACAGGCCAATCATACCGGCTTCTACT
sFLT1OPT2-Genedesign AGCAGTTCTGCAGCACCCTGACCCTGAACACCGCCCAGGCCAACCACACCGGCTTCTACA
sFLT1OPT4-DNA2.0     AACAGTTCTGCTCCACCCTGACATTGAATACCGCGCAGGCCAACCACACTGGATTCTATT
sFLT1OPT5-Geneart    AGCAGTTCTGCAGCACCCTGACCCTGAATACCGCCCAGGCCAACCACACCGGCTTCTACA
sFLT1OPT6-IDT        AGCAGTTCTGTAGCACACTGACTTTGAACACCGCACAGGCCAATCACACTGGCTTCTACT
sFLT1OPT3-Genewiz    AACAGTTCTGCTCCACACTCACCCTGAACACAGCTCAAGCCAATCACACAGGCTTCTACT
sFLT1OPT7-BlueHeron  AGCAGTTCTGTTCCACACTGACTCTGAATACTGCACAAGCTAATCATACCGGATTTTATT
sFLT1-orf            AACAATTCTGCAGTACTTTAACCTTGAACACAGCTCAAGCAAACCACACTGGCTTCTACA
Consensus            AGCAGTTCTGCTGCAC-CTGACCCTGAACACCGC-CAGGCCAATCACACCGGCTTCTACT
```

Figure 1 Cont.(i)

```
sFLT1OPT8-Genescript CTTGCAAGTATCTGGCCGTGCCCACCAGTAAGAAAAAGGAGACAGAATCAGCTATCTATA
sFLT1OPT2-Genedesign GCTGCAAGTACCTGGCCGTGCCCACCAGCAAGAAGAAGGAGACCGAGAGCGCCATCTACA
sFLT1OPT4-DNA2.0     CGTGTAAGTACTTGGCGGTGCCCACGAGCAAAAAGAAAGAGACTGAGTCGGCGATCTACA
sFLT1OPT5-Geneart    GCTGCAAGTACCTGGCCGTGCCCACCAGCAAGAAGAAAGAAACCGAGAGCGCCATCTACA
sFLT1OPT6-IDT        CATGTAAATATCTGGCGGTTCCCACATCTAAAAAAAAGGAAACCGAATCAGCCATCTATA
sFLT1OPT3-Genewiz    CCTGCAAATATCTCGCCGTCCCCACAAGCAAGAAGAAAGAAACAGAGTCCGCCATTTACA
sFLT1OPT7-BlueHeron  CCTGTAAATATCTGGCCGTGCCTACCAGTAAGAAAAAGGAAACCGAGAGTGCCATATATA
sFLT1-orf            GCTGCAAATATCTAGCTGTACCTACTTCAAAGAAGAAGGAAACAGAATCTGCAATCTATA
Consensus            CCTGCAAGTATCTGGCCGTGCCCACCAGCAAGAAGAAGGAAACCGAGT-CGCCATCTATA

sFLT1OPT8-Genescript TTTTCATCAGCGATACCGGACGGCCCTTTGTGGAGATGTACAGTGAGATCCCTGAAATCA
sFLT1OPT2-Genedesign TCTTCATCAGCGACACCGGCCGCCCCTTCGTGGAGATGTACAGCGAGATCCCCGAGATCA
sFLT1OPT4-DNA2.0     TCTTTATCTCAGACACGGGGAGGCCGTTCGTGGAAATGTATTCGGAGATTCCCGAGATCA
sFLT1OPT5-Geneart    TCTTCATCAGCGACACCGGCAGACCCTTCGTGGAAATGTACAGCGAGATCCCCGAGATCA
sFLT1OPT6-IDT        TATTTATTTCAGACACCGGCCGCCCTTTCGTTGAAATGTACTCCGAGATTCCTGAAATTA
sFLT1OPT3-Genewiz    TTTTCATCTCCGATACCGGCAGGCCCTTCGTCGAAATGTACAGCGAGATCCCCGAGATCA
sFLT1OPT7-BlueHeron  TCTTCATTAGCGACACAGGTCGCCCTTTCGTGGAGATGTACTCAGAAATCCCCGAGATCA
sFLT1-orf            TATTTATTAGTGATACAGGTAGACCTTTCGTAGAGATGTACAGTGAAATCCCCGAAATTA
Consensus            TCTTCATCAGCGACACCGGCCG-CCCTTCGTGGAGATGTACAGCGAGATCCCCGAGATCA

sFLT1OPT8-Genescript TTCACATGACTGAGGGCAGGGAGCTGGTCATCCCATGTCGCGTCACCTCACCCAATATCA
sFLT1OPT2-Genedesign TCCACATGACCGAGGGCCGCGAGCTGGTGATCCCCTGCCGCGTGACCAGCCCCAACATCA
sFLT1OPT4-DNA2.0     TCCACATGACAGAAGGGCGAGAGCTCGTCATCCCGTGTCGCGTAACTTCACCCAACATCA
sFLT1OPT5-Geneart    TCCACATGACCGAGGGCCGCGAGCTCGTGATCCCTTGCAGAGTGACCAGCCCCAACATCA
sFLT1OPT6-IDT        TTCATATGACAGAAGGGAGGGAGCTGGTGATACCGTGTAGGGTAACCAGCCCCAACATCA
sFLT1OPT3-Genewiz    TCCATATGACCGAAGGCAGAGAGCTCGTCATTCCCTGCAGGGTCACCAGCCCCAATATTA
sFLT1OPT7-BlueHeron  TCCACATGACTGAAGGCCGAGAACTCGTGATACCTTGTCGGGTGACTAGTCCTAATATCA
sFLT1-orf            TACACATGACTGAAGGAAGGGAGCTCGTCATTCCCTGCCGGGTTACGTCACCTAACATCA
Consensus            TCCACATGACGAAGGCC--GGAGCTCGTGATCCC-TGTCGGGT-ACCAGCCCCAACATCA
```

Figure 1 Cont.(ii)

```
sFLT1OPT8-Genescript CAGTGACTCTGAAAAAGTTCCCTCTGGACACCCTGATTCCAGATGGAAAACGCATCATTT
sFLT1OPT2-Genedesign CCGTGACCCTGAAGAAGTTCCCCCTGGACACCCTGATCCCCGACGGCAAGCGCATCATCT
sFLT1OPT4-DNA2.0     CCGTGACACTCAAGAAGTTTCCACTGGACACACTGATTCCCGACGGAAAGCGGATCATCT
sFLT1OPT5-Geneart    CCGTGACACTGAAGAAGTTCCCCCTGGACACCCTGATCCCCGACGGCAAGAGAATCATCT
sFLT1OPT6-IDT        CTGTGACTCTCAAAAAATTCCCCCTGGACACGCTGATCCCCGATGGAAAGCGGATTATTT
sFLT1OPT3-Genewiz    CCGTGACCCTGAAAAAGTTCCCCCTCGATACACTCATTCCCGACGGCAAGAGGATCATCT
sFLT1OPT7-BlueHeron  CTGTCACACTGAAAAAGTTCCCCCTCGATACACTCATCCCCGATGGAAAACGCATTATCT
sFLT1-orf            CTGTTACTTTAAAAAAGTTTCCACTTGACACTTTGATCCCTGATGGAAAACGCATAATCT
Consensus            CCGTGAC-CTGAAAAAGTTCCCCCTGGACA-CCTGATCCCCGATGGAAAGCGCATCATCT

sFLT1OPT8-Genescript GGGACTCCCGAAAGGGCTTTATCATCTCTAACGCAACATACAAGGAGATCGGGCTGCTGA
sFLT1OPT2-Genedesign GGGACAGCCGCAAGGGCTTCATCATCAGCAACGCCACCTACAAGGAGATCGGCCTGCTGA
sFLT1OPT4-DNA2.0     GGGATTCACGAAAGGGGTTTATCATTTCCAACGCGACTTACAAAGAGATCGGACTGCTGA
sFLT1OPT5-Geneart    GGGACAGCCGGAAGGGCTTCATCATCAGCAACGCCACCTACAAAGAGATCGGCCTGCTGA
sFLT1OPT6-IDT        GGGATTCACGGAAAGGGTTTATTATTTCCAACGCCACCTACAAGGAGATCGGACTGCTGA
sFLT1OPT3-Genewiz    GGGATTCCAGAAAGGGCTTCATTATTAGCAATGCCACCTATAAGGAGATTGGACTGCTGA
sFLT1OPT7-BlueHeron  GGGACAGTCGCAAAGGATTTATTATTTCCAACGCTACATATAAGGAAATCGGGTTGCTCA
sFLT1-orf            GGGACAGTAGAAAGGGCTTCATCATATCAAATGCAACGTACAAAGAAATAGGGCTTCTGA
Consensus            GGGACTGCCGAAAGGGCTTTATCATTTCCAACGCCACCTACAAGGAGATCGG-CTGCTGA

sFLT1OPT8-Genescript CCTGCGAAGCCACAGTGAACGGACATCTGTACAAGACTAATTATCTGACCCACAGACAGA
sFLT1OPT2-Genedesign CCTGCGAGGCCACCGTGAACGGCCACCTGTACAAGACCAACTACCTGACCCACCGCCAGA
sFLT1OPT4-DNA2.0     CGTGCGAGGCCACCGTCAACGGACACCTCTATAAGACGAATTATCTCACGCACAGACAGA
sFLT1OPT5-Geneart    CCTGCGAGGCCACCGTGAATGGCCACCTGTACAAGACCAACTACCTGACCCACAGACAGA
sFLT1OPT6-IDT        CGTGTGAGGCGACTGTCAACGGACACCTGTACAAAACCAACTATCTGACACATCGCCAGA
sFLT1OPT3-Genewiz    CCTGTGAGGCCACCGTGAACGGCCACCTCTACAAGACCAACTACCTCACACACAGGCAGA
sFLT1OPT7-BlueHeron  CCTGCGAAGCTACCGTGAACGGGCATCTCTATAAGACTAATTATCTGACCCACAGGCAGA
sFLT1-orf            CCTGTGAAGCAACAGTCAATGGGCATTTGTATAAGACAAACTATCTCACACATCGACAAA
Consensus            CCTGCGAGGCCACCGTGAACGG-CACCTGTACAAGACCAACTATCTGACCCACAGACAGA
```

Figure 1 Cont.9(iii)

```
sFLT1OPT8-Genescript CCAATACAATCATTGATGTGCAGATCAGCACCCCACGGCCTGTCAAGCTGCTGAGAGGAC
sFLT1OPT2-Genedesign CCAACACCATCATCGACGTGCAGATCAGCACCCCCCGCCCCGTGAAGCTGCTGCGCGGCC
sFLT1OPT4-DNA2.0     CCAACACCATCATCGACGTACAGATCTCAACCCCACGGCCGGTAAAACTGCTCAGGGGGC
sFLT1OPT5-Geneart    CCAACACCATCATCGACGTGCAGATCAGCACCCCCAGACCCGTGAAGCTGCTGAGAGGCC
sFLT1OPT6-IDT        CCAATACCATCATAGATGTGCAAATCTCAACACCAAGGCCCGTGAAACTGCTGCGCGGTC
sFLT1OPT3-Genewiz    CCAACACCATCATTGACGTCCAGATCAGCACCCCCAGGCCTGTGAAACTGCTCAGAGGCC
sFLT1OPT7-BlueHeron  CTAACACAATTATAGACGTACAGATTAGCACACCCAGACCTGTCAAGCTGCTTCGAGGCC
sFLT1-orf            CCAATACAATCATAGATGTCCAAATAAGCACACCACGCCCAGTCAAATTACTTAGAGGCC
Consensus            CCAACACCATCAT-GACGTGCAGATCAGCACCCCCCGGCC-GTGAAGCTGCTGAGAGGCC

sFLT1OPT8-Genescript ATACTCTGGTCCTGAACTGTACCGCCACCACACCTCTGAATACCAGAGTGCAGATGACAT
sFLT1OPT2-Genedesign ACACCCTGGTGCTGAACTGCACCGCCACCACCCCCCTGAACACCCGCGTGCAGATGACCT
sFLT1OPT4-DNA2.0     ACACGCTCGTACTGAATTGCACAGCGACGACGCCCCTGAATACGAGGGTCCAGATGACCT
sFLT1OPT5-Geneart    ACACCCTGGTGCTGAATTGCACCGCCACCACCCCCCTGAACACCAGAGTGCAGATGACCT
sFLT1OPT6-IDT        ACACTCTGGTGCTCAATTGCACTGCAACGACGCCTCTGAATACGCGAGTGCAGATGACTT
sFLT1OPT3-Genewiz    ATACACTGGTCCTCAACTGCACAGCCACAACACCCCTGAACACAAGGGTGCAGATGACCT
sFLT1OPT7-BlueHeron  ATACTCTGGTTCTCAATTGCACCGCTACCACTCCCCTGAATACCCGGGTCCAAATGACAT
sFLT1-orf            ATACTCTTGTCCTCAATTGTACTGCTACCACTCCCTTGAACACGAGAGTTCAAATGACCT
Consensus            ATACTCTGGT-CTGAATTGCACCGCCACCAC-CCCCTGAATACCAGAGTGCAGATGACCT

sFLT1OPT8-Genescript GGTCTTACCCAGACGAGAAAAACAAGAGGGCTAGTGTCCGGAGAAGGATCGACCAGTCTA
sFLT1OPT2-Genedesign GGAGCTACCCCGACGAGAAGAACAAGCGCGCCAGCGTGCGCCGCCGCATCGACCAGAGCA
sFLT1OPT4-DNA2.0     GGTCGTACCCGGACGAAAAGAATAAGCGGGCGTCGGTGCGGAGAAGGATCGACCAGTCGA
sFLT1OPT5-Geneart    GGTCCTACCCCGACGAGAAGAACAAGAGGGCCAGCGTGCGGCGGAGAATCGACCAGAGCA
sFLT1OPT6-IDT        GGTCCTATCCCGATGAGAAAAACAAGCGCGCCTCAGTAAGAAGAAGGATTGACCAAAGCA
sFLT1OPT3-Genewiz    GGAGCTACCCTGACGAGAAAAACAAGAGGGCCAGCGTGAGAAGGAGAATTGACCAGTCCA
sFLT1OPT7-BlueHeron  GGTCATATCCGGATGAGAAGAACAAACGAGCTAGCGTGCGCCGACGCATTGACCAGTCCA
sFLT1-orf            GGAGTTACCCTGATGAAAAAAATAAGAGAGCTTCCGTAAGGCGACGAATTGACCAAAGCA
Consensus            GGTCCTACCC-GACGAGAAGAACAAGCGGGCCAGCGTGCGGCGAAG-ATTGACCAGTGCA
```

Figure 1 Cont. (iv)

```
sFLT1OPT8-Genescript ACAGTCACGCAAATATTTTCTATAGCGTGCTGACAATCGACAAGATGCAGAACAAAGATA
sFLT1OPT2-Genedesign ACAGCCACGCCAACATCTTCTACAGCGTGCTGACCATCGACAAGATGCAGAACAAGGACA
sFLT1OPT4-DNA2.0     ATTCACATGCTAATATCTTCTACTCGGTACTCACGATCGATAAGATGCAGAACAAAGATA
sFLT1OPT5-Geneart    ACAGCCACGCCAACATCTTCTACTCCGTGCTGACCATCGACAAGATGCAGAACAAGGACA
sFLT1OPT6-IDT        ACAGCCATGCCAACATCTTCTATTCAGTCCTGACAATCGACAAAATGCAAAACAAAGATA
sFLT1OPT3-Genewiz    ACAGCCACGCTAACATCTTCTATTCCGTCCTGACAATTGACAAGATGCAGAACAAGGATA
sFLT1OPT7-BlueHeron  ATAGCCACGCGAACATTTTTTATTCTGTTCTTACCATCGACAAGATGCAGAATAAAGATA
sFLT1-orf            ATTCCCATGCCAACATATTCTACAGTGTTCTTACTATTGACAAAATGCAGAACAAAGACA
Consensus            ACAGCCACGCCAACATCTTCTATTCCGT--CTGACATCGACAAGATGCAGAACAAAGATA

sFLT1OPT8-Genescript AGGGCCTGTACACTTGTCGCGTGCGAAGTGGGCCTTCATTCAAAAGCGTGAATACTTCCG
sFLT1OPT2-Genedesign AGGGCCTGTACACCTGCCGCGTGCGCAGCGGCCCCAGCTTCAAGAGCGTGAACACCAGCG
sFLT1OPT4-DNA2.0     AGGGGTTGTACACTTGTAGGGTCAGGAGCGGGCCTTCGTTCAAAAGCGTAAACACCAGCG
sFLT1OPT5-Geneart    AGGGCCTGTACACCTGTAGAGTGCGGAGCGGCCCCAGCTTCAAGAGCGTGAACACCTCCG
sFLT1OPT6-IDT        AGGGCCTTTATACTTGTCGCGTGAGGAGCGGTCCATCTTTCAAAAGTGTAAATACAAGTG
sFLT1OPT3-Genewiz    AGGGCCTCTATACCTGCAGAGTCAGATCCGGACCCAGCTTTAAATCCGTGAATACCAGCG
sFLT1OPT7-BlueHeron  AGGGGTTGTATACGTGTCGAGTCAGAAGCGGGCCTAGCTTCAAGAGTGTCAACACATCCG
sFLT1-orf            AAGGACTTTATACTTGTCGTGTAAGGAGTGGACCATCATTCAAATCTGTTAACACCTCAG
Consensus            AGGGCCTGTATACTTGTCG-GTGAGGAGCGG--CCTGCTTCAAAAGCGTGAACACCTGCG

sFLT1OPT8-Genescript TCCATATCTATGACAAAGCCTTCATCACCGTGAAACACCGGAAGCAGCAGGTGCTGGAGA
sFLT1OPT2-Genedesign TGCACATCTACGACAAGGCCTTCATCACCGTGAAGCACCGCAAGCAGCAGGTGCTGGAGA
sFLT1OPT4-DNA2.0     TCCACATCTACGACAAGGCCTTTATCACGGTCAAGCATAGGAAGCAGCAAGTACTGGAAA
sFLT1OPT5-Geneart    TGCACATCTACGACAAGGCCTTCATCACAGTGAAGCACCGGAAGCAGCAGGTGCTGGAAA
sFLT1OPT6-IDT        TTCATATTTATGATAAAGCTTTCATTACAGTGAAACACCGAAAACAGCAGGTGCTGGAAA
sFLT1OPT3-Genewiz    TCCACATCTACGACAAGGCCTTCATCACAGTGAAACACAGGAAGCAGCAGGTGCTCGAGA
sFLT1OPT7-BlueHeron  TCCACATATACGATAAAGCCTTTATCACTGTGAAGCACCGCAAACAACAAGTCCTGGAGA
sFLT1-orf            TGCATATATATGATAAAGCATTCATCACTGTGAAACATCGAAAACAGCAGGTGCTTGAAA
Consensus            TCCACATCTACGACAAGGCCTTCATCAC-GTGAAGCACCGGAAGCAGCAGGTGCTGGAGA
```

Figure 1 Cont. (v)

```
sFLT1OPT8-Genescript CAGTCGCCGGGAAAAGGAGCTACCGCCTGTCCATGAAAGTGAAGGCTTTTCCATCCCCCG
sFLT1OPT2-Genedesign CCGTGGCCGGCAAGCGCAGCTACCGCCTGAGCATGAAGGTGAAGGCCTTCCCCAGCCCCG
sFLT1OPT4-DNA2.0     CTGTAGCAGGAAAGAGATCATATAGGTTGTCCATGAAAGTCAAGGCGTTCCCATCCCCGG
sFLT1OPT5-Geneart    CCGTGGCCGGCAAGCGGAGCTACAGACTGAGCATGAAAGTGAAAGCCTTCCCCAGCCCCG
sFLT1OPT6-IDT        CAGTGGCTGGCAAGCGCTCCTACCGACTTAGCATGAAGGTAAAAGCGTTCCCTTCTCCTG
sFLT1OPT3-Genewiz    CCGTGGCCGGCAAGAGGTCCTACAGGCTGTCCATGAAGGTCAAAGCTTTCCCTTCCCCCG
sFLT1OPT7-BlueHeron  CAGTGGCTGGCAAGCGATCCTATAGGCTGAGCATGAAGGTAAAGGCCTTCCCCAGCCCGG
sFLT1-orf            CCGTAGCTGGCAAGCGGTCTTACCGGCTCTCTATGAAAGTGAAGGCATTTCCCTCGCCGG
Consensus            CCGTGGCCGGCAAGCGGTCCTACCGGCTGTGCATGAAGGTGAAGGC-TTCCCCTCCCCCG

sFLT1OPT8-Genescript AGGTGGTCTGGCTGAAAGATGGCCTGCCAGCCACAGAAAAGAGCGCCCGATACCTGACTC
sFLT1OPT2-Genedesign AGGTGGTGTGGCTGAAGGACGGCCTGCCCGCCACCGAGAAGAGCGCCCGCTACCTGACCC
sFLT1OPT4-DNA2.0     AGGTCGTATGGCTTAAGGACGGACTCCCCGCCACGGAAAAGTCGGCACGCTATTTGACGC
sFLT1OPT5-Geneart    AGGTCGTGTGGCTGAAAGATGGACTGCCCGCCACCGAGAAGTCCGCCAGATACCTGACCA
sFLT1OPT6-IDT        AAGTCGTGTGGCTGAAGGACGGCCTGCCAGCTACAGAAAAGAGCGCTCGGTATTTGACCA
sFLT1OPT3-Genewiz    AGGTCGTGTGGCTCAAAGACGGCCTCCCCGCCACCGAGAAAAGCGCTAGATACCTCACCA
sFLT1OPT7-BlueHeron  AGGTGGTGTGGCTTAAGGATGGCCTGCCTGCGACAGAGAAATCAGCAAGATATCTGACCA
sFLT1-orf            AAGTTGTATGGTTAAAAGATGGGTTACCTGCGACTGAGAAATCTGCTCGCTATTTGACTC
Consensus            AGGTCGTGTGGCTGAAGGATGGCCTGCCCGCCA-CGAGAAGTGCGCC-GATATCTGACCC

sFLT1OPT8-Genescript GGGGGTATTCCCTGATCATTAAGGACGTGACCGAGGAAGATGCAGGAAACTACACAATCC
sFLT1OPT2-Genedesign GCGGCTACAGCCTGATCATCAAGGACGTGACCGAGGAGGACGCCGGCAACTACACCATCC
sFLT1OPT4-DNA2.0     GGGGTTATTCGCTGATCATTAAGGATGTCACAGAAGAGGATGCGGGGAACTATACAATTC
sFLT1OPT5-Geneart    GAGGCTACAGCCTGATCATCAAGGACGTGACCGAAGAGGACGCCGGCAACTACACCATCC
sFLT1OPT6-IDT        GAGGCTACAGCCTGATTATCAAGGATGTGACTGAAGAGGACGCCGGCAATTACACAATTC
sFLT1OPT3-Genewiz    GAGGCTACAGCCTGATCATCAAGGACGTGACAGAAGAGGATGCTGGCAACTACACCATTC
sFLT1OPT7-BlueHeron  GGGGGTACTCTCTTATAATCAAAGACGTAACGGAAGAGGATGCCGGTAACTACACCATAC
sFLT1-orf            GTGGCTACTCGTTAATTATCAAGGACGTAACTGAAGAGGATGCAGGGAATTATACAATCT
Consensus            G-GGCTACTGCCTGATCATCAAGGACGTGA-CGAAGAGGATGCCGGCAACTACACCATCC
```

Figure 1 Cont. (vi)

```
sFLT1OPT8-Genescript TGCTGAGCATCAAGCAGAGTAACGTGTTCAAGAATCTGACTGCCACCCTGATTGTGAATG
sFLT1OPT2-Genedesign TGCTGAGCATCAAGCAGAGCAACGTGTTCAAGAACCTGACCGCCACCCTGATCGTGAACG
sFLT1OPT4-DNA2.0     TTCTTTCCATCAAGCAGTCCAATGTGTTCAAGAATTTGACAGCAACCCTCATCGTAAACG
sFLT1OPT5-Geneart    TGCTGTCCATCAAGCAGAGCAACGTGTTCAAGAACCTGACCGCCACACTGATCGTGAACG
sFLT1OPT6-IDT        TGCTTTCCATCAAGCAGTCAAACGTTTTCAAAAATCTGACAGCTACGTTGATCGTGAACG
sFLT1OPT3-Genewiz    TCCTGTCCATCAAGCAATCCAACGTCTTCAAGAACCTGACCGCCACACTCATCGTGAATG
sFLT1OPT7-BlueHeron  TGCTCAGCATCAAACAGAGTAACGTTTTTAAGAATTTGACCGCAACCCTGATAGTCAATG
sFLT1-orf            TGCTGAGCATAAAACAGTCAAATGTGTTTAAAAACCTCACTGCCACTCTAATTGTCAATG
Consensus            TGCTGTGCATCAAGCAGTGCAACGTGTTCAAGAATCTGACCGCCACCCTGATCGTGAATG

sFLT1OPT8-Genescript TCAAACCCCAGATCTACGAGAAGGCCGTGAGCAGCTTCCCTGACCCAGCACTGTATCCTC
sFLT1OPT2-Genedesign TGAAGCCCCAGATCTACGAGAAGGCCGTGAGCAGCTTCCCCGACCCCGCCCTGTACCCCC
sFLT1OPT4-DNA2.0     TAAAGCCTCAAATCTACGAAAAGGCAGTGAGCTCATTCCCTGACCCAGCGTTGTACCCTC
sFLT1OPT5-Geneart    TGAAGCCCCAGATCTATGAGAAGGCCGTGTCCAGCTTCCCCGACCCCGCTCTGTATCCTC
sFLT1OPT6-IDT        TCAAACCTCAAATCTACGAGAAAGCCGTTAGCAGCTTTCCAGACCCTGCTCTCTACCCCC
sFLT1OPT3-Genewiz    TCAAGCCCCAGATCTACGAGAAGGCCGTGAGCAGCTTCCCCGATCCTGCCCTGTATCCCC
sFLT1OPT7-BlueHeron  TGAAACCTCAGATCTACGAGAAAGCCGTGTCTTCATTCCCCGACCCCGCCCTGTACCCCC
sFLT1-orf            TGAAACCCCAGATTTACGAAAAGGCCGTGTCATCGTTTCCAGACCCGGCTCTCTACCCAC
Consensus            TGAAGCCCCAGATCTACGAGAAGGCCGTGAGCAGCTTCCCCGACCC--GCCTGTACCCCC

sFLT1OPT8-Genescript TGGGCAGCCGGCAGATCCTGACATGCACTGCCTACGGCATCCCCCAGCCTACCATTAAGT
sFLT1OPT2-Genedesign TGGGCAGCCGCCAGATCCTGACCTGCACCGCCTACGGCATCCCCCAGCCCACCATCAAGT
sFLT1OPT4-DNA2.0     TGGGCTCGAGACAGATCCTTACGTGTACTGCGTACGGGATTCCCCAGCCTACCATTAAGT
sFLT1OPT5-Geneart    TGGGCAGCAGGCAGATCCTGACCTGCACAGCCTACGGCATCCCCCAGCCCACCATCAAGT
sFLT1OPT6-IDT        TCGGATCTCGGCAAATCCTGACCTGTACTGCGTATGGAATCCCCCAACCAACCATCAAGT
sFLT1OPT3-Genewiz    TCGGCTCCAGACAAATTCTCACCTGCACCGCCTACGGAATTCCCCAGCCCACCATCAAGT
sFLT1OPT7-BlueHeron  TGGGTTCTCGCCAGATCCTTACTTGCACTGCCTACGGAATTCCTCAGCCTACGATTAAGT
sFLT1-orf            TGGGCAGCAGACAAATCCTGACTTGTACCGCATATGGTATCCCTCAACCTACAATCAAGT
Consensus            TGGGCTGCCG-CAGATCCTGACCTGCACTGCCTACGG-ATCCCCCAGCCTACCATCAAGT
```

Figure 1 Cont. (vii)

```
sFLT1OPT8-Genescript GGTTCTGGCATCCTTGTAACCACAATCATAGTGAAGCAAGGTGCGATTTCTGTTCCAACA
sFLT1OPT2-Genedesign GGTTCTGGCACCCCTGCAACCACAACCACAGCGAGGCCCGCTGCGACTTCTGCAGCAACA
sFLT1OPT4-DNA2.0     GGTTTTGGCATCCCTGCAACCACAACCACTCGGAGGCGAGGTGCGACTTTTGCAGCAACA
sFLT1OPT5-Geneart    GGTTCTGGCACCCCTGCAACCACAACCACAGCGAGGCCAGATGCGACTTCTGCTCCAACA
sFLT1OPT6-IDT        GGTTTTGGCACCCATGTAATCACAATCATTCTGAAGCCCGCTGTGATTTCTGCTCAAACA
sFLT1OPT3-Genewiz    GGTTTTGGCACCCCTGCAACCACAACCATTCCGAGGCCAGATGCGATTTCTGCTCCAATA
sFLT1OPT7-BlueHeron  GGTTTTGGCATCCTTGTAACCATAACCATAGCGAGGCACGGTGCGACTTCTGTAGCAATA
sFLT1-orf            GGTTCTGGCACCCCTGTAACCATAATCATTCCGAAGCAAGGTGTGACTTTTGTTCCAATA
Consensus            GGTTTTGGCACCCCTGTAACCACAACCATTGCGAGGCCAGGTGCGACTTCTGCTCCAACA

sFLT1OPT8-Genescript ATGAGGAATCTTTTATCCTGGACGCCGATAGTAACATGGGCAATCGAATCGAGTCAATTA
sFLT1OPT2-Genedesign ACGAGGAGAGCTTCATCCTGGACGCCGACAGCAACATGGGCAACCGCATCGAGAGCATCA
sFLT1OPT4-DNA2.0     ACGAAGAATCGTTCATCCTTGATGCAGACTCAAACATGGGTAATCGGATCGAATCGATCA
sFLT1OPT5-Geneart    ACGAGGAAAGCTTCATCCTGGACGCCGACAGCAACATGGGCAACCGGATCGAGTCCATCA
sFLT1OPT6-IDT        ATGAGGAGTCCTTCATCCTGGACGCAGACAGCAATATGGGCAATCGGATTGAGTCAATCA
sFLT1OPT3-Genewiz    ACGAGGAGTCCTTCATCCTCGATGCTGACAGCAACATGGGAAACAGGATCGAATCCATCA
sFLT1OPT7-BlueHeron  ACGAGGAGTCTTTCATTCTGGATGCAGACTCTAATATGGGTAACCGCATTGAGTCCATCA
sFLT1-orf            ATGAAGAGTCCTTTATCCTGGATGCTGACAGCAACATGGGAAACAGAATTGAGAGCATCA
Consensus            ACGAGGAGTCCTTCATCCTGGATG-CGACAGCAACATGGGCAACCGGATCGAGTCCATCA

sFLT1OPT8-Genescript CCCAGCGGATGGCTATCATTGAAGGGAAAAACAAGATGGCATCTACACTGGTGGTCGCCG
sFLT1OPT2-Genedesign CCCAGCGCATGGCCATCATCGAGGGCAAGAACAAGATGGCCAGCACCCTGGTGGTGGCCG
sFLT1OPT4-DNA2.0     CCCAACGCATGGCTATCATTGAGGGGAAGAATAAGATGGCATCGACTTTGGTCGTGGCCG
sFLT1OPT5-Geneart    CCCAGAGAATGGCCATCATTGAGGGCAAGAACAAAATGGCCTCTACCCTGGTGGTGGCCG
sFLT1OPT6-IDT        CACAGAGGATGGCAATTATAGAGGGAAAAAACAAAATGGCGAGCACCCTGGTCGTGGCTG
sFLT1OPT3-Genewiz    CCCAGAGGATGGCCATCATCGAGGGCAAAAATAAAATGGCCAGCACCCTGGTCGTCGCCG
sFLT1OPT7-BlueHeron  CGCAGAGGATGGCCATTATCGAAGGGAAAAATAAGATGGCCTCTACTCTGGTGGTGGCTG
sFLT1-orf            CTCAGCGCATGGCAATAATAGAAGGAAAGAATAAGATGGCTAGCACCTTGGTTGTGGCTG
Consensus            CCCAGCGGATGGCCATCAT--GAGGGAAGAATAAGATGGCCTGCACCCTGGTGGTGGCCG
```

Figure 1 Cont. (viii)

```
sFLT1OPT8-Genescript ACTCCCGCATCTCTGGCATCTACATCTGCATTGCCTCAAACAAAGTGGGAACAGTCGGCC
sFLT1OPT2-Genedesign ACAGCCGCATCAGCGGCATCTACATCTGCATCGCCAGCAACAAGGTGGGCACCGTGGGCC
sFLT1OPT4-DNA2.0     ACTCGCGGATCTCAGGCATCTACATTTGCATCGCAAGCAACAAAGTGGGAACGGTCGGAC
sFLT1OPT5-Geneart    ACTCCAGAATCAGCGGCATCTATATCTGTATCGCCAGCAACAAAGTGGGCACCGTGGGCC
sFLT1OPT6-IDT        ACTCCAGAATCAGTGGCATCTACATCTGTATCGCCTCAAACAAGGTCGGGACAGTCGGTC
sFLT1OPT3-Genewiz    ACAGCAGGATTAGCGGCATCTACATTTGCATCGCCTCCAACAAAGTGGGCACCGTGGGAA
sFLT1OPT7-BlueHeron  ATAGCCGCATCTCAGGCATTTATATCTGCATAGCTTCTAATAAAGTTGGGACAGTGGGGA
sFLT1-orf            ACTCTAGAATTTCTGGAATCTACATTTGCATAGCTTCCAATAAAGTTGGGACTGTGGGAA
Consensus            ACTCCCGATCTG--GGCATCTACATCTGCATCGCCTCCAACAAAGTGGGACGT---GGGC

sFLT1OPT8-Genescript GGAATATCAGCTTCTACATTACTGATGTGCCAAACGGATTTCACGTCAATCTGGAGAAGA
sFLT1OPT2-Genedesign GCAACATCAGCTTCTACATCACCGACGTGCCCAACGGCTTCCACGTGAACCTGGAGAAGA
sFLT1OPT4-DNA2.0     GGAACATTTCGTTCTATATCACTGATGTACCCAATGGGTTTCACGTAAACCTCGAGAAAA
sFLT1OPT5-Geneart    GGAACATCAGCTTCTACATCACCGATGTGCCCAACGGCTTCCACGTGAACCTGGAAAAGA
sFLT1OPT6-IDT        GCAATATCAGCTTCTATATTACAGACGTGCCTAACGGTTTTCATGTGAACCTCGAGAAGA
sFLT1OPT3-Genewiz    GGAATATCAGCTTCTATATCACCGACGTGCCCAACGGATTTCACGTGAATCTGGAGAAGA
sFLT1OPT7-BlueHeron  GGAATATCTCCTTCTACATTACCGATGTCCCAAACGGATTCCATGTGAACCTTGAAAAAA
sFLT1-orf            GAAACATAAGCTTTTATATCACAGATGTGCCAAATGGGTTTCATGTTAACTTGGAAAAAA
Consensus            GGAATATCAGCTTCTATATCACCGATGTGCCCAACGG-TTTCACGTGAACCTGGAGAAGA

sFLT1OPT8-Genescript TGCCCACCGAGGGCGAAGACCTGAAACTGTCTTGTACAGTGAATAAGTTCCTGTATAGGG
sFLT1OPT2-Genedesign TGCCCACCGAGGGCGAGGACCTGAAGCTGAGCTGCACCGTGAACAAGTTCCTGTACCGCG
sFLT1OPT4-DNA2.0     TGCCTACGGAAGGAGAGGATTTGAAGCTTTCGTGCACCGTGAACAAGTTTCTCTACCGCG
sFLT1OPT5-Geneart    TGCCCACCGAGGGCGAGGACCTGAAGCTGTCCTGTACCGTGAACAAGTTTCTGTACCGCG
sFLT1OPT6-IDT        TGCCTACAGAGGGAGAGGATCTGAAACTGTCATGCACTGTAAACAAATTCTTGTACCGCG
sFLT1OPT3-Genewiz    TGCCTACCGAGGGAGAAGATCTCAAGCTCAGCTGCACCGTCAACAAGTTTCTGTACAGGG
sFLT1OPT7-BlueHeron  TGCCGACTGAGGGCGAGGATCTTAAGCTGTCATGCACTGTCAATAAGTTTCTGTATCGAG
sFLT1-orf            TGCCGACGGAAGGAGAGGACCTGAAACTGTCTTGCACAGTTAACAAGTTCTTATACAGAG
Consensus            TG-CCACCGAGGGCGAGGATCTGAAGCTGT-CTGCACCGTGAACAAGTTTCTGTACCGCG
```

Figure 1 Cont. (ix)

```
sFLT1OPT8-Genescript ATGTCACTTGGATTCTGCTGAGAACTGTGAACAATAGGACCATGCATTACTCAATCAGCA
sFLT1OPT2-Genedesign ACGTGACCTGGATTCTGCTGCGCACCGTGAACAACCGCACCATGCACTACAGCATCAGCA
sFLT1OPT4-DNA2.0     ATGTGACGTGGATCTTGCTTAGAACGGTGAACAACAGGACAATGCACTACTCCATCTCGA
sFLT1OPT5-Geneart    ACGTGACCTGGATTCTGCTGCGGACAGTGAACAACCGGACCATGCACTACAGCATCAGCA
sFLT1OPT6-IDT        ACGTCACTTGGATCTTGCTGAGAACAGTCAATAACAGGACCATGCACTACTCAATTAGCA
sFLT1OPT3-Genewiz    ACGTCACATGGATTCTGCTCAGGACCGTCAACAACAGGACCATGCATTACTCCATTTCCA
sFLT1OPT7-BlueHeron  ACGTGACTTGGATACTCCTGCGGACTGTGAATAACCGGACTATGCATTACAGCATATCTA
sFLT1-orf            ACGTTACTTGGATTTTACTGCGGACAGTTAATAACAGAACAATGCACTACAGTATTAGCA
Consensus            ACGTGACTTGGATTCTGCTGCGGAC-GTGAACAACAGGACCATGCACTACTGCATCAGCA

sFLT1OPT8-Genescript AACAGAAGATGGCTATCACCAAGGAACACAGCATTACACTGAACCTGACTATCATGAACG
sFLT1OPT2-Genedesign AGCAGAAGATGGCCATCACCAAGGAGCACAGCATCACCCTGAACCTGACCATCATGAACG
sFLT1OPT4-DNA2.0     AGCAGAAAATGGCAATCACTAAAGAACATAGCATTACGCTCAACTTGACTATTATGAATG
sFLT1OPT5-Geneart    AGCAGAAGATGGCTATCACCAAAGAGCACAGCATCACCCTGAATCTGACCATCATGAACG
sFLT1OPT6-IDT        AGCAGAAGATGGCTATCACCAAAGAGCACTCCATCACACTGAACCTGACTATCATGAATG
sFLT1OPT3-Genewiz    AGCAGAAGATGGCCATCACCAAGGAGCACAGCATCACACTCAACCTGACCATCATGAATG
sFLT1OPT7-BlueHeron  AGCAGAAAATGGCCATCACTAAGGAACACTCCATTACCCTGAACCTCACCATAATGAACG
sFLT1-orf            AGCAAAAAATGGCCATCACTAAGGAGCACTCCATCACTCTTAATCTTACCATCATGAATG
Consensus            AGCAGAAGATGGCCATCACCAAGGAGCACAGCATCAC-CTGAACCTGACCATCATGAATG

sFLT1OPT8-Genescript TGAGCCTCCAGGACAGCGGACCTACGCTTGCCGGGCAAGAAACGTGTATACAGGAGAGG
sFLT1OPT2-Genedesign TGAGCCTGCAGGACAGCGGCACCTACGCCTGCCGCGCCCGCAACGTGTACACCGGCGAGG
sFLT1OPT4-DNA2.0     TATCGCTTCAAGATTCGGGGACCTATGCATGTAGAGCTCGCAACGTCTATACAGGCGAAG
sFLT1OPT5-Geneart    TGTCACTGCAGGACAGCGGCACCTACGCCTGCAGAGCCAGAAACGTGTACACCGGCGAGG
sFLT1OPT6-IDT        TCTCCTTGCAGGACTCTGGCACTTATGCTTGTCGGGCGAGGAATGTGTATACAGGCGAGG
sFLT1OPT3-Genewiz    TGTCCCTCCAGGACAGCGGAACATACGCCTGCAGGGCCAGAAACGTCTACACAGGCGAAG
sFLT1OPT7-BlueHeron  TCAGCCTCCAAGATTCTGGAACCTACGCTTGCAGGGCCCGAAATGTCTACACAGGGGAGG
sFLT1-orf            TTTCCCTGCAAGATTCAGGCACCTATGCCTGCAGAGCCAGGAATGTATACACAGGGGAAG
Consensus            TGTCCCTGCAGGACTGCGGCACCTACGCCTGCAGGGCCAGAAACGTGTACACAGGCGAGG
```

Figure 1 Cont. (x)

```
sFLT1OPT8-Genescript AAATCCTCCAGAAGAAGGAGATCACAATTCGCGGCGAACACTGTAACAAGAAGGCCGTGT
sFLT1OPT2-Genedesign AGATCCTGCAGAAGAAGGAGATCACCATCCGCGGCGAGCACTGCAACAAGAAGGCCGTGT
sFLT1OPT4-DNA2.0     AAATTCTTCAAAAGAAGGAGATTACTATCCGGGGTGAGCACTGCAACAAAAAGGCGGTCT
sFLT1OPT5-Geneart    AAATCCTGCAGAAAAAAGAGATCACCATCCGGGGCGAGCACTGCAACAAGAAAGCCGTGT
sFLT1OPT6-IDT        AAATCCTCCAGAAGAAGGAGATTACAATTAGGGGAGAACATTGTAATAAGAAAGCAGTAT
sFLT1OPT3-Genewiz    AGATCCTGCAGAAAAAGGAGATCACCATCAGAGGCGAGCACTGCAACAAGAAGGCCGTCT
sFLT1OPT7-BlueHeron  AGATACTCCAGAAGAAGGAAATCACCATTCGGGGGGAACACTGCAATAAGAAAGCTGTGT
sFLT1-orf            AAATCCTCCAGAAGAAAGAAATTACAATCAGAGGTGAGCACTGCAACAAAAAGGCTGTTT
Consensus            AAATCCTCCAGAAGAAGGAGATCACCATCCGGGGCGAGCACTGCAACAAGAAGGCCGTGT

sFLT1OPT8-Genescript TTAGCCGAATCTCCAAGTTCAAGTCAACCAGGAATGATTGTACTACCCAGTCAAATGTCA
sFLT1OPT2-Genedesign TCAGCCGCATCAGCAAGTTCAAGAGCACCCGCAACGACTGCACCACCCAGAGCAACGTGA
sFLT1OPT4-DNA2.0     TTAGCCGAATCTCAAAGTTCAAATCGACTAGAAACGACTGTACAACGCAGTCAAACGTCA
sFLT1OPT5-Geneart    TCAGCCGGATCAGCAAGTTCAAGAGCACCCGGAACGACTGCACCACCCAGTCCAATGTGA
sFLT1OPT6-IDT        TTAGTAGAATCAGTAAATTTAAGTCCACCAGGAACGACTGTACTACTCAGTCCAACGTAA
sFLT1OPT3-Genewiz    TCTCCAGGATCAGCAAGTTCAAATCCACCAGGAACGACTGCACAACCCAATCCAATGTCA
sFLT1OPT7-BlueHeron  TCAGCAGGATTTCCAAGTTCAAAAGCACTCGAAACGACTGCACCACTCAGTCAAACGTGA
sFLT1-orf            TCTCTCGGATCTCCAAATTTAAAAGCACAAGGAATGATTGTACCACACAAAGTAATGTAA
Consensus            TCAGCCGGATCTGCAAGTTCAAGTGCACCAGGAACGACTGTACCACCCAGTCCAATGT-A

sFLT1OPT8-Genescript AGCACTAGTAAGGATCCCCAACACACTCTGATCGATGCATCTGAGC
sFLT1OPT2-Genedesign AGCATTAGTAAGGATCCCCAACACACTCTGATCGATGCATCTGAGC
sFLT1OPT4-DNA2.0     AGCATTAGTAAGGATCCCCAACACACTCTGATCGATGCATCTGAGC
sFLT1OPT5-Geneart    AGCACTGATGAGGATCCCCAACACACTCTGATCGATGCATCTGAGC
sFLT1OPT6-IDT        AACATTAGTAAGGATCCCCAACACACTCTGATCGATGCATCTGAGC
sFLT1OPT3-Genewiz    AGCATTAGTAAGGATCCCCAACACACTCTGATCGATGCATCTGAGC
sFLT1OPT7-BlueHeron  AACACTAGTAAGGATCCCCAACACACTCTGATCGATGCATCTGAGC
sFLT1-orf            AACATTAGTAA-----------------------------------
Consensus            AGCATTAGTAAGGATCCCCAACACACTCTGATCGATGCATCTGAGC
```

Figure 1 Cont. (xi)

| Number | Name | sort | %GC content |
|---|---|---|---|
| sFLT-OPT-8 | GeneScript | 1 | 51 |
| sFLT-OPT-2 | Gene Design | 2 | 63 |
| sFLT-OPT-4 | DNA2.0 | 3 | 50 |
| sFLT-OPT-5 | GeneArt | 4 | 58 |
| sFLT-OPT-6 | IDT | 5 | 47 |
| sFLT-OPT-7 | BlueHeron | 6 | 49 |
| sFLT-OPT-3 | Genewiz | 7 | 54 |
| 1 | unoptimized | 8 | 43 |

Figure 2 atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttaaagaaga tacgtctttt gggggcaacc tcggacgagc agtcttccag 360
gcgaaaaaga gggttcttga acctctgggc ctggttgagg aacctgttaa gacggctccg 420
ggaaaaaaga ggccggtaga gcactctcct gtggagccag actcctcctc gggaaccgga 480
aaggcgggcc agcagcctgc aagaaaaaga ttgaattttg gtcagactgg agacgcagac 540
tcagtacctg acccccagcc tctcggacag ccaccagcag ccccctctgg tctgggaact 600
aatacgatgg ctacaggcag tggcgcacca atggcagaca ataacgaggg cgccgacgga 660
gtgggtaatt cctcgggaaa ttggcattgc gattccacat ggatgggcga cagagtcatc 720
accaccagca cccgaacctg ggccctgccc acctacaaca accacctcta caaacaaatt 780
tccagcgctt caacgggagc ctcgaacgac aatcactact ttggctacag caccccttgg 840
gggtattttg acttcaacag attccactgc cacttttcac cacgtgactg gcaaagactc 900
atcaacaaca actggggatt ccgacccaag agactcaact tcaagctctt taacattcaa 960
gtcaaagagg tcacgcagaa tgacggtacg acgacgattg ccaataacct taccagcacg 1020
gttcaggtgt ttactgactc ggagtaccag ctcccgtacg tcctcggctc ggcgcatcaa 1080
ggatgcctcc cgccgttccc agcagacgtc ttcatggtgc cacagtatgg atacctcacc 1140
ctgaacaacg ggagtcaggc agtaggacgc tcttcatttt actgcctgga gtactttcct 1200
tctcagatgc tgcgtaccgg aaacaacttt accttcagct acacttttga ggacgttcct 1260
ttccacagca gctacgctca cagccagagt ctggaccgtc tcatgaatcc tctcatcgac 1320
cagtacctgt attacttgag cagaacaaac actccaagtg gaaccaccac gcagtcaagg 1380
cttcagtttt ctcaggccgg agcgagtgac attcgggacc agtctaggaa ctggcttcct 1440
ggaccctgtt accgccagca gcgagtatca aagacatctg cggataacaa caacagtgaa 1500
tactcgtgga ctggagctac caagtaccac ctcaatggca gagactctct ggtgaatccg 1560
ggcccggcca tggcaagcca caaggacgat gaagaaaagt tttttcctca gagcggggtt 1620
ctcatctttg ggaagcaagg ctcagagaaa acaaatgtgg acattgaaaa ggtcatgatt 1680
acagacgaag aggaaatcag gacaaccaat cccgtggcta cggagcagta tggttctgta 1740
tctaccaacc tccagagagg caacagacaa gcagctaccg cagatgtcaa cacacaaggc 1800
gttcttccag gcatggtctg gcaggacaga gatgtgtacc ttcaggggcc catctgggca 1860
aagattccac acacggacgg acattttcac ccctctcccc tcatgggtgg attcggactt 1920
aaacaccctc ctccacagat tctcatcaag aacaccccgg tacctgcgaa tccttcgacc 1980
accttcagtg cggcaaagtt tgcttccttc atcacacagt actccacggg acaggtcagc 2040
gtggagatcg agtgggagct gcagaaggaa aacagcaaac gctggaatcc cgaaattcag 2100
tacacttcca actacgccaa gtctgtcaat gtggacttta ctgtggacaa taatggcgtg 2160
tattcagagc ctcgccccat tggcaccaga tacctgactc gtaatctgta a 2211

Figure 3

AAV1 capsid atggctgccgatggttatcttccagattggctcgaggacaacctctctgagggcattcgcgagtggtgggactt
gaaacctggagccccgaagcccaaagccaaccagcaaaagcaggacgacggccggggtctggtgcttcctg
gctacaagtacctcggacccttcaacggactcgacaagggggagcccgtcaacgcggcggacgcagcggccc
tcgagcacgacaaggcctacgaccagcagctcaaagcgggtgacaatccgtacctgcggtataaccacgccg
acgccgagtttcaggagcgtctgcaagaagatacgtcttttgggggcaacctcgggcgagcagtcttccaggc
caagaagcgggttctcgaacctctcggtctggttgaggaaggcgctaagacggctcctggaaagaaacgtcc
ggtagagcagtcgccacaagagccagactcctcctcgggcatcggcaagacaggccagcagcccgctaaaa
agagactcaattttggtcagactggcgactcagagtcagtccccgatccacaacctctcggagaacctccagc
aacccccgctgctgtgggacctactacaatggcttcaggcggtggcgcaccaatggcagacaataacgaagg
cgccgacggagtgggtaatgcctcaggaaattggcattgcgattccacatggctgggcgacagagtcatcacc
accagcacccgcacctgggccttgcccacctacaataaccacctctacaagcaaatctccagtgcttcaacgg
gggccagcaacgacaaccactacttcggctacagcaccccctgggggtattttgatttcaacagattccactgc
cacttttcaccacgtgactggcagcgactcatcaacaacaattggggattccggcccaagagactcaacttca
aactcttcaacatccaagtcaaggaggtcacgacgaatgatggcgtcacaaccatcgctaataaccttaccag
cacggttcaagtcttctcggactcggagtaccagcttccgtacgtcctcggctctgcgcaccagggctgcctccc
tccgttcccggcggacgtgttcatgattccgcaatacggctacctgacgctcaacaatggcagccaagccgtgg
gacgttcatccttttactgcctggaatatttcccttctcagatgctgagaacgggcaacaactttaccttcagcta
cacctttgaggaagtgcctttccacagcagctacgcgcacagccagagcctggaccggctgatgaatcctctc
atcgaccaatacctgtattacctgaacagaactcaaaatcagtccggaagtgcccaaaacaaggacttgctgt
ttagccgtgggtctccagctggcatgtctgttcagcccaaaaactggctacctggaccctgttatcggcagcag
cgcgtttctaaaacaaaaacagacaacaacaacagcaattttacctggactggtgcttcaaaatataacctca
atgggcgtgaatccatcatcaaccctggcactgctatggcctcacacaaagacgacgaagacaagttctttcc
catgagcggtgtcatgatttttggaaaagagagcgccggagcttcaaacactgcattggacaatgtcatgatt
acagacgaagaggaaattaaagccactaaccctgtggccaccgaaagatttgggaccgtggcagtcaatttc
cagagcagcagcacagaccctgcgaccggagatgtgcatgctatgggagcattacctggcatggtgtggcaa
gatagagacgtgtacctgcagggtcccatttgggccaaaattcctcacacagatggacactttcacccgtctcc
tcttatgggcggctttggactcaagaacccgcctcctcagatcctcatcaaaaacacgcctgttcctgcgaatcc
tccggcggagttttcagctacaaagtttgcttcattcatcacccaatactccacaggacaagtgagtgtggaaa
ttgaatgggagctgcagaaagaaaacagcaagcgctggaatcccgaagtgcagtacacatccaattatgca
aaatctgccaacgttgattttactgtggacaacaatggactttatactgagcctcgccccattggcacccgttac
cttacccgtcccctgtaa

Figure 4

AAV1 capsid/265del atggctgccgatggttatcttccagattggctcgaggacaacctctctgagggcattcgcgagtggtgggactt
gaaacctggagccccgaagcccaaagccaaccagcaaaagcaggacgacggccggggtctggtgcttcctg
gctacaagtacctcggacccttcaacggactcgacaaggggggagcccgtcaacgcggcggacgcagcggccc
tcgagcacgacaaggcctacgaccagcagctcaaagcgggtgacaatccgtacctgcggtataaccacgccg
acgccgagtttcaggagcgtctgcaagaagatacgtcttttggggggcaacctcgggcgagcagtcttccaggc
caagaagcgggttctcgaacctctcggtctggttgaggaaggcgctaagacggctcctggaaagaaacgtcc
ggtagagcagtcgccacaagagccagactcctcctcgggcatcggcaagacaggccagcagcccgctaaaa
agagactcaattttggtcagactggcgactcagagtcagtccccgatccacaacctctcggagaacctccagc
aacccccgctgctgtgggacctactacaatggcttcaggcggtggcgcaccaatggcagacaataacgaagg
cgccgacggagtgggtaatgcctcaggaaattggcattgcgattccacatggctgggcgacagagtcatcacc
accagcacccgcacctgggccttgcccacctacaataaccacctctacaagcaaatctccagtgcttcagggg
ccagcaacgacaaccactacttcggctacagcaccccctgggggtattttgatttcaacagattccactgccac
ttttcaccacgtgactggcagcgactcatcaacaacaattggggattccggcccaagagactcaacttcaaac
tcttcaacatccaagtcaaggaggtcacgacgaatgatggcgtcacaaccatcgctaataaccttaccagcac
ggttcaagtcttctcggactcggagtaccagcttccgtacgtcctcggctctgcgcaccagggctgcctccctcc
gttcccggcggacgtgttcatgattccgcaatacggctacctgacgctcaacaatggcagccaagccgtggga
cgttcatccttttactgcctggaatatttcccttctcagatgctgagaacgggcaacaactttaccttcagctaca
cctttgaggaagtgcctttccacagcagctacgcgcacagccagagcctggaccggctgatgaatcctctcatc
gaccaatacctgtattacctgaacagaactcaaaatcagtccggaagtgcccaaaacaaggacttgctgttta
gccgtgggtctccagctggcatgtctgttcagcccaaaaactggctacctggaccctgttatcggcagcagcgc
gtttctaaaacaaaaacagacaacaacaacagcaattttacctggactggtgcttcaaaatataacctcaatg
ggcgtgaatccatcatcaaccctggcactgctatggcctcacacaaagacgacgaagacaagttctttcccat
gagcggtgtcatgatttttggaaaagagagcgccggagcttcaaacactgcattggacaatgtcatgattaca
gacgaagaggaaattaaagccactaaccctgtggccaccgaaagatttgggaccgtggcagtcaatttccag
agcagcagcacagaccctgcgaccggagatgtgcatgctatgggagcattacctggcatggtgtggcaagat
agagacgtgtacctgcagggtcccatttgggccaaaattcctcacacagatggacactttcacccgtctcctctt
atgggcggctttggactcaagaacccgcctcctcagatcctcatcaaaaacacgcctgttcctgcgaatcctcc
ggcggagttttcagctacaaagtttgcttcattcatcacccaatactccacaggacaagtgagtgtggaaattg
aatgggagctgcagaaagaaaacagcaagcgctggaatcccgaagtgcagtacacatccaattatgcaaaa
tctgccaacgttgattttactgtggacaacaatggactttatactgagcctcgccccattggcacccgttacctta
cccgtcccctgtaa

Figure 5

AAV6 capsid atggctgccgatggttatcttccagattggctcgaggacaacctctctgagggcattcgcgagtggtgggactt
gaaacctggagccccgaaacccaaagccaaccagcaaaagcaggacgacggccggggtctggtgcttcctg
gctacaagtacctcggacccttcaacggactcgacaagggggagcccgtcaacgcggcggatgcagcggccc
tcgagcacgacaaggcctacgaccagcagctcaaagcgggtgacaatccgtacctgcggtataaccacgccg
acgccgagtttcaggagcgtctgcaagaagatacgtcttttgggggcaacctcgggcgagcagtcttccaggc
caagaagagggttctcgaaccttttggtctggttgaggaaggtgctaagacggctcctggaaagaaacgtccg
gtagagcagtcgccacaagagccagactcctcctcgggcattggcaagacaggccagcagcccgctaaaaa
gagactcaattttggtcagactggcgactcagagtcagtccccgacccacaacctctcggagaacctccagca
acccccgctgctgtgggacctactacaatggcttcaggcggtggcgcaccaatggcagacaataacgaaggc
gccgacggagtgggtaatgcctcaggaaattggcattgcgattccacatggctgggcgacagagtcatcacca
ccagcacccgaacatgggccttgcccacctataacaaccacctctacaagcaaatctccagtgcttcaacggg
ggccagcaacgacaaccactacttcggctacagcaccccctgggggtattttgatttcaacagattccactgcc
atttctcaccacgtgactggcagcgactcatcaacaacaattggggattccggcccaagagactcaacttcaa
gctcttcaacatccaagtcaaggaggtcacgacgaatgatggcgtcacgaccatcgctaataaccttaccagc
acggttcaagtcttctcggactcggagtaccagttgccgtacgtcctcggctctgcgcaccagggctgcctccct
ccgttcccggcggacgtgttcatgattccgcagtacggctacctaacgctcaacaatggcagccaggcagtgg
gacggtcatccttttactgcctggaatatttcccatcgcagatgctgagaacgggcaataactttaccttcagct
acaccttcgaggacgtgcctttccacagcagctacgcgcacagccagagcctggaccggctgatgaatcctctc
atcgaccagtacctgtattacctgaacagaactcagaatcagtccggaagtgcccaaaacaaggacttgctgt
ttagccgggggtctccagctggcatgtctgttcagcccaaaaactggctacctggaccctgttaccggcagcag
cgcgtttctaaaacaaaaacagacaacaacaacagcaactttacctggactggtgcttcaaaatataacctta
atgggcgtgaatctataatcaaccctggcactgctatggcctcacacaaagacgacaaagacaagttctttcc
catgagcggtgtcatgatttttggaaaggagagcgccggagcttcaaacactgcattggacaatgtcatgatc
acagacgaagaggaaatcaaagccactaaccccgtggccaccgaaagatttgggactgtggcagtcaatctc
cagagcagcagcacagaccctgcgaccggagatgtgcatgttatgggagccttacctggaatggtgtggcaa
gacagagacgtatacctgcagggtcctatttgggccaaaattcctcacacggatggacactttcacccgtctcc
tctcatgggcggctttggacttaagcacccgcctcctcagatcctcatcaaaaacacgcctgttcctgcgaatcc
tccggcagagttttcggctacaaagtttgcttcattcatcacccagtattccacaggacaagtgagcgtggaga
ttgaatgggagctgcagaaagaaaacagcaaacgctggaatcccgaagtgcagtatacatctaactatgca
aaatctgccaacgttgatttcactgtggacaacaatggactttatactgagcctcgccccattggcacccgttac
ctcacccgtcccctgtaa

Figure 6

AAV6 capsid/265del atggctgccgatggttatcttccagattggctcgaggacaacctctctgagggcattcgcgagtggtgggactt
gaaacctggagccccgaaacccaaagccaaccagcaaaagcaggacgacggccggggtctggtgcttcctg
gctacaagtacctcggacccttcaacggactcgacaagggggagcccgtcaacgcggcggatgcagcggccc
tcgagcacgacaaggcctacgaccagcagctcaaagcgggtgacaatccgtacctgcggtataaccacgccg
acgccgagtttcaggagcgtctgcaagaagatacgtcttttgggggcaacctcgggcgagcagtcttccaggc
caagaagagggttctcgaaccttttggtctggttgaggaaggtgctaagacggctcctggaaagaaacgtccg
gtagagcagtcgccacaagagccagactcctcctcgggcattggcaagacaggccagcagcccgctaaaaa
gagactcaattttggtcagactggcgactcagagtcagtccccgacccacaacctctcggagaacctccagca
acccccgctgctgtgggacctactacaatggcttcaggcggtggcgcaccaatggcagacaataacgaaggc
gccgacggagtgggtaatgcctcaggaaattggcattgcgattccacatggctgggcgacagagtcatcacca
ccagcacccgaacatgggccttgcccacctataacaaccacctctacaagcaaatctccagtgcttcaggggc
cagcaacgacaaccactacttcggctacagcaccccctgggggtattttgatttcaacagattccactgccattt
ctcaccacgtgactggcagcgactcatcaacaacaattggggattccggcccaagagactcaacttcaagctc
ttcaacatccaagtcaaggaggtcacgacgaatgatggcgtcacgaccatcgctaataaccttaccagcacgg
ttcaagtcttctcggactcggagtaccagttgccgtacgtcctcggctctgcgcaccagggctgcctccctccgtt
cccggcggacgtgttcatgattccgcagtacggctacctaacgctcaacaatggcagccaggcagtgggacgg
tcatccttttactgcctggaatatttcccatcgcagatgctgagaacgggcaataactttaccttcagctacacc
ttcgaggacgtgcctttccacagcagctacgcgcacagccagagcctggaccggctgatgaatcctctcatcga
ccagtacctgtattacctgaacagaactcagaatcagtccggaagtgcccaaaacaaggacttgctgtttagc
cgggggtctccagctggcatgtctgttcagcccaaaaactggctacctggaccctgttaccggcagcagcgcgt
ttctaaaacaaaaacagacaacaacaacagcaactttacctggactggtgcttcaaaatataaccttaatgg
gcgtgaatctataatcaaccctggcactgctatggcctcacacaaagacgacaaagacaagttctttcccatg
agcggtgtcatgatttttggaaaggagagcgccggagcttcaaacactgcattggacaatgtcatgatcacag
acgaagaggaaatcaaagccactaaccccgtggccaccgaaagatttgggactgtggcagtcaatctccaga
gcagcagcacagaccctgcgaccggagatgtgcatgttatgggagccttacctggaatggtgtggcaagaca
gagacgtatacctgcagggtcctatttgggccaaaattcctcacacggatggacactttcacccgtctcctctca
tgggcggctttggacttaagcacccgcctcctcagatcctcatcaaaaacacgcctgttcctgcgaatcctccgg
cagagttttcggctacaaagtttgcttcattcatcacccagtattccacaggacaagtgagcgtggagattgaa
tgggagctgcagaaagaaaacagcaaacgctggaatcccgaagtgcagtatacatctaactatgcaaaatct
gccaacgttgatttcactgtggacaacaatggactttatactgagcctcgccccattggcacccgttacctcacc
cgtcccctgtaa

Figure 7

AAV6 capsid/265del/K531E atggctgccgatggttatcttccagattggctcgaggacaacctctctgagggcattcgcgagtggtgggactt
gaaacctggagccccgaaacccaaagccaaccagcaaaagcaggacgacggccggggtctggtgcttcctg
gctacaagtacctcggacccttcaacggactcgacaagggggagcccgtcaacgcggcggatgcagcggccc
tcgagcacgacaaggcctacgaccagcagctcaaagcgggtgacaatccgtacctgcggtataaccacgccg
acgccgagtttcaggagcgtctgcaagaagatacgtcttttgggggcaacctcgggcgagcagtcttccaggc
caagaagagggttctcgaaccttttggtctggttgaggaaggtgctaagacggctcctggaaagaaacgtccg
gtagagcagtcgccacaagagccagactcctcctcgggcattggcaagacaggccagcagcccgctaaaaa
gagactcaattttggtcagactggcgactcagagtcagtccccgacccacaacctctcggagaacctccagca
acccccgctgctgtgggacctactacaatggcttcaggcggtggcgcaccaatggcagacaataacgaaggc
gccgacggagtgggtaatgcctcaggaaattggcattgcgattccacatggctgggcgacagagtcatcacca
ccagcacccgaacatgggccttgcccacctataacaaccacctctacaagcaaatctccagtgcttcaggggc
cagcaacgacaaccactacttcggctacagcacccccctgggggtattttgatttcaacagattccactgccattt
ctcaccacgtgactggcagcgactcatcaacaacaattggggattccggcccaagagactcaacttcaagctc
ttcaacatccaagtcaaggaggtcacgacgaatgatggcgtcacgaccatcgctaataaccttaccagcacgg
ttcaagtcttctcggactcggagtaccagttgccgtacgtcctcggctctgcgcaccagggctgcctccctccgtt
cccggcggacgtgttcatgattccgcagtacggctacctaacgctcaacaatggcagccaggcagtgggacgg
tcatccttttactgcctggaatatttcccatcgcagatgctgagaacgggcaataactttaccttcagctacacc
ttcgaggacgtgcctttccacagcagctacgcgcacagccagagcctggaccggctgatgaatcctctcatcga
ccagtacctgtattacctgaacagaactcagaatcagtccggaagtgcccaaaacaaggacttgctgtttagc
cgggggtctccagctggcatgtctgttcagcccaaaaactggctacctggaccctgttaccggcagcagcgcgt
ttctaaaacaaaaacagacaacaacaacagcaactttacctggactggtgcttcaaaatataaccttaatgg
gcgtgaatctataatcaaccctggcactgctatggcctcacacaaagacgacgaagacaagttctttcccatg
agcggtgtcatgatttttggaaaggagagcgccggagcttcaaacactgcattggacaatgtcatgatcacag
acgaagaggaaatcaaagccactaaccccgtggccaccgaaagatttgggactgtggcagtcaatctccaga
gcagcagcacagaccctgcgaccggagatgtgcatgttatgggagccttacctggaatggtgtggcaagaca
gagacgtatacctgcagggtcctatttgggccaaaattcctcacacggatggacactttcacccgtctcctctca
tgggcggctttggacttaagcacccgcctcctcagatcctcatcaaaaacacgcctgttcctgcgaatcctccgg
cagagttttcggctacaaagtttgcttcattcatcacccagtattccacaggacaagtgagcgtggagattgaa
tgggagctgcagaaagaaaacagcaaacgctggaatcccgaagtgcagtatacatctaactatgcaaaatct
gccaacgttgatttcactgtggacaacaatggactttatactgagcctcgccccattggcacccgttacctcacc
cgtcccctgtaa

Figure 8

```
aav1c-738              Ctgggccttgcccacctacaataaccacctctacaagcaaatctccagtgcttcaacggg
aav6c-738              Atgggccttgcccacctataacaaccacctctacaagcaaatctccagtgcttcaacggg
aav1/265d-738          Ctgggccttgcccacctacaataaccacctctacaagcaaatctccagtgcttca---gg
aav6/265d-738          Atgggccttgcccacctataacaaccacctctacaagcaaatctccagtgcttca---gg
aav6/265d/k531E738     Atgggccttgcccacctataacaaccacctctacaagcaaatctccagtgcttca---gg
consensus738           Atgggccttgcccacctataacaaccacctctacaagcaaatctccagtgcttca---gg

aav1c                  ggccagcaacgacaaccactacttcggctacagca 832
aav6c                  ggccagcaacgacaaccactacttcggctacagca 832
aav1c/265d             ggccagcaacgacaaccactacttcggctacagca 832
aav6c/265d             ggccagcaacgacaaccactacttcggctacagca 832
aav6c/265d/k531E       ggccagcaacgacaaccactacttcggctacagca 832
consensus              ggccagcaacgacaaccactacttcggctacagca 832

aav1c-1540             cgtgaatccatcatcaaccctggcactgctatggcctcacacaaagacgacgaagacaag
aav6c-1540             cgtgaatctataatcaaccctggcactgctatggcctcacacaaagacgacaaagacaag
aav1c/265d-1537        cgtgaatccatcatcaaccctggcactgctatggcctcacacaaagacgacgaagacaag
aav6c/265d-1537        cgtgaatctataatcaaccctggcactgctatggcctcacacaaagacgacaaagacaag
aav6c/265d/k531E-1537  cgtgaatctataatcaaccctggcactgctatggcctcacacaaagacgacgaagacaag
consensus-1540         cgtgaatctataatcaaccctggcactgctatggcctcacacaaagacgacgaagacaag

aav1c                  ttctttcccatgagcggtgtcatgatttttggaaa 1634
aav6c                  ttctttcccatgagcggtgtcatgatttttggaaa 1634
aav1c/265d             ttctttcccatgagcggtgtcatgatttttggaaa 1634
aav6c/265d             ttctttcccatgagcggtgtcatgatttttggaaa 1634
aav6c/265d/k531E       ttctttcccatgagcggtgtcatgatttttggaaa 1634
consensus              ttctttcccatgagcggtgtcatgatttttggaaa 1634
```

Figure 9

| Number | Name | Luciferace (RLU) | ELISA (pg/ml) | ELISA/Luc | Increase in Expression |
|---|---|---|---|---|---|
| SEQ ID 1 | unoptimized | 1.49E+06 | 3.25E+04 | 2.18E-02 | 1.00 |
| SEQ ID 2 | Gene Design | 1.31E+06 | 1.00E+05 | 7.64E-02 | 3.50 |
| SEQ ID 3 | Genewiz | 1.38E+06 | 5.12E+04 | 3.72E-02 | 1.71 |
| SEQ ID 4 | DNA2.0 | 1.03E+03 | 4.79E+03 | 4.65E+00 | 212.83 |
| SEQ ID 5 | GeneArt | 1.30E+06 | 8.53E+04 | 6.58E-02 | 3.01 |
| SEQ ID 6 | IDT | 1.41E+06 | 6.34E+04 | 4.49E-02 | 2.06 |
| SEQ ID 7 | BlueHeron | 1.69E+06 | 7.56E+04 | 4.49E-02 | 2.05 |
| SEQ ID 8 | GeneScript | 8.50E+05 | 1.29E+05 | 1.52E-01 | 6.96 |

Figure 10

| name | Luciferace (mean, RLU) | ELISA (mean, pg/ml) | ELISA/Luc (mean, pg/ml/RLU) | Folds |
|---|---|---|---|---|
| 1unoptimized | 1.89E+04 | 1.53E+04 | 8.77E-01 | 1.00 |
| 2Gene Design | 1.84E+04 | 8.76E+04 | 4.96E+00 | 5.66 |
| 4DNA2.0 | 9.68E+03 | 2.67E+04 | 2.85E+00 | 3.25 |
| 8GeneScript | 1.13E+04 | 8.49E+04 | 7.90E+00 | 9.01 |

| name | ELISA (pg/ml) |
|---|---|
| 1 unoptimized-David-AAV2 | 4.12E+01 |
| 2 Gene Design-AAV2 | 4.64E+04 |
| 8 GeneScript-AAV2 | 2.48E+04 |

Control

AAV2-OPT-2

MODIFIED SOLUBLE VEGF RECEPTOR-1 GENES AND VECTORS FOR GENE THERAPY

CROSS REFERENCE TO RELATED APPLICATION

This application is filed under the provisions of 35 U.S.C. § 371 and claims the priority of International Patent Application No. PCT/US2014/024119 filed on Mar. 12, 2014 which in turn claims priority of U.S. Provisional Application No. 61/782,450 filed on Mar. 14, 2013, the contents of which are incorporated by reference herein for all purposes.

BACKGROUND OF THE INVENTION

Field of the Invention

The invention relates to modified soluble VEGF receptor-1 (also known as sFlt1) genes, nucleic acid vectors including the modified genes, optimized viral capsids including the modified genes, methods of using the modified genes in the treatment of diseases related to ocular neovascularization, such as macular degeneration.

Discussion of Related Art

Leading causes of severe vision loss and blindness are ocular-related disorders wherein the vasculature of the eye is damaged or insufficiently regulated. Ocular-related diseases comprising a neovascularization aspect are many and include, for example, exudative age-related macular degeneration, diabetic retinopathy, corneal neovascularization, choroidal neovascularization, neovascular glaucoma, cyclitis, Hippel-Lindau Disease, retinopathy of prematurity, pterygium, histoplasmosis, iris neovascularization, macular edema, glaucoma-associated neovascularization, and the like.

Damage of the retina, i.e., retinal detachment, retinal tears, or retinal degeneration, is directly connected to vision loss. A common cause of retinal detachment, retinal tears, and retinal degeneration is abnormal, that being, uncontrolled vascularization of various ocular tissues.

It has been found that vascular endothelial growth factor (VEGF) is a major stimulatory factor for retinal neovascularisation. It is unlikely to be the only stimulatory factor but it is nevertheless the key factor involved. VEGF is upregulated by hypoxia and its levels are increased in the retina and vitreous of patients or laboratory animals with ischaemic retinopathies. Also, increased expression of VEGF in retinal photoreceptors stimulates neovascularisation in the retina and VEGF antagonists inhibit retinal or iris neovascularisation in animal models.

For many ocular-related disorders, no efficient therapeutic options currently are available. Laser photocoagulation involves administering laser burns to various areas of the eye and is used in the treatment of many neovascularization-linked disorders. Laser treatment does not guarantee that vision loss will be attenuated. In fact, many patients afflicted with age-related macular degeneration eventually experience severe vision loss in spite of treatment. Other treatment options for ocular-related disorders include thermotherapy, radiation therapy, surgery, e.g., macular translocation, removal of excess ocular tissue, drug therapy, and the like. However, in most cases, all available treatment options have limited therapeutic effect, require repeated, costly procedures, and/or are associated with dangerous side-effects.

Given the prevalence of ocular-related disorders, there remains a need for an effective prophylactic and therapeutic treatment of ocular-related disorders. Accordingly, the invention provides materials and methods for achieving a beneficial effect in the eye, such as inhibiting or reducing angiogenesis or preventing photoreceptor cell loss. This and other advantages of the invention will become apparent from the detailed description provided herein.

SUMMARY OF THE INVENTION

The present invention provides a method for treating ocular neovascularization comprising delivering to target cells in the eye of a subject in need of treatment, a vector comprising a promoter sequence in operable linkage with a polynucleotide sequence encoding an anti-angiogenesis gene product, wherein the anti-angiogenesis gene product is expressed in the target cells, thereby treating ocular neovascularization in the subject.

The target cells are preferably retinal cells, more preferably retinal pigment epithelial cells, and the vector is preferably delivered to the target cells via direct sub-retinal injection The present invention provides for modified soluble vascular endothelial growth factor (VEGF) receptor-1 genes (sFlt1), nucleic acid vectors including the modified genes, optimized viral capsids including the modified genes, and methods of using the modified genes in the treatment of diseases caused ocular neovascularization, such as macular degeneration.

In one aspect, the present invention provides for optimized sFlt1 genes for treating ocular disorder causing neovascularization, such as macular degeneration in a human subject wherein the optimized genes have been modified to increase CG sequences and reduce cis motifs. Preferably the optimized genes comprise sequences SEQ ID NO: 2 or 8.

In yet another aspect, the present invention provides for a method of treating ocular disorder causing neovascularization in a subject, the method comprising:

a. providing at least one recombinant virus vector comprising a nucleotide sequences for comprising a modified sFlt1 gene; and b. administering the recombinant virus vector to the subject under conditions such that said sFlt1 nucleotide sequences are expressed at a level which produces a therapeutically effective amount of sFlt1 (SEQ ID NO: 26) in the subject, wherein a therapeutically effective amount is an amount sufficient to bind with VEGF thereby reducing angiogenesis in retina tissue of the subject.

In a still further aspect, the present invention provides for a method of transducing an immune privilege retina cell with a modified sFlt1 gene, the method comprising contacting the immune privilege retina cell with a recombinant virus vector comprising an optimized sFlt1 gene comprising the sequence of SEQ ID NO: 2 or 8.

Another aspect of the present invention provides for therapies to treat ocular disorder causing neovascularization, such as macular degeneration including gene therapy based on administration of a nucleotide sequence encoding for optimized sFlt1 genes, as recited in SEQ ID NO: 2 or 8.

In an alternative aspect, the present invention provides an expression vector comprising a polynucleotide that encodes an optimized sFlt1 gene or fragment thereof. In one embodiment the expression vector is an AVV virus vector including the sequence of AAV1, AAV2 (SEQ ID NO: 22), AAV3, AAV4, AAV5, AAV6, AAV7, AAV8, AAV 9, AAV10, AAV11, AAV12 or chimeric variants thereof such as variant AAV2 Capsid 2.5 (SEQ ID NO. 10). Other modified sequences nucleotide sequence of modified AAV 1.1 capsid wherein amino acid residue 265 is deleted (SEQ ID NO: 12), nucleotide sequence of modified AAV 6.1 capsid wherein amino acid residue 265 is deleted (SEQ ID NO: 14), nucleotide sequence of modified AAV 6.3.1 capsid wherein amino acid residue 265 is deleted and amino acid residue 531 is changed from a Lys to a Glu (SEQ ID NO: 15). The nucleotide sequence of wildtype AAV 1 capsid is shown in (SEQ ID NO: 11) and the nucleotide sequence of wildtype AAV 6 capsid is set forth in (SEQ ID NO: 13).

In yet another aspect, the present invention provides a recombinant host cell transfected with a polynucleotide that encodes an optimized sFlt1 peptide of the present invention and selected from any one of SEQ ID NOs: 2 to 8.

In a still further aspect, the present invention contemplates a process of preparing a sFlt1 peptide or fragment thereof comprising;

a. transfecting a cell with polynucleotide that encodes the sFlt1 peptide or fragment thereof to produce a transformed host cell; and b. maintaining the transformed host cell under biological conditions sufficient for expression of the peptide.

In another aspect, the present invention relates to the use of an optimized sFlt1 gene of the present invention in the use of a medicament for the treatment of ocular degeneration.

The present invention also provides for a pharmaceutical composition comprising optimized sFlt1 genes for treating ocular disorders causing neovascularization in a human subject wherein the optimized genes have been modified to increase CG sequences and reduce cis motifs and in combination with a pharmaceutically acceptable carrier. The optimized genes comprise a sequence selected from SEQ ID NO: 2 or SEQ ID NO: 8.

Other features and advantages of the invention will be apparent from the following detailed description, drawings and claims.

BRIEF DESCRIPTION OF THE FIGURES

FIG. 1 shows the sequences of eight optimized sFlt1 sequences, that being, SEQ ID NO: 1 (sFLT-orf unoptimized), SEQ ID NO: 2 (sFLT-OPT-2 GeneDesign); SEQ ID NO: 3 (sFLT-OPT-3 Genewiz); SEQ ID NO: 4 (sFLT-OPT-4 DNA2.0); SEQ ID NO: 5 (sFLT-OPT-5 Geneart); SEQ ID NO: 6 (sFLT-OPT-6 IDT); SEQ ID NO: 7 (sFLT-OPT-7 BlueHeron); SEQ ID NO: 8 (sFLT-OPT8 Genescript); SEQ ID NO: 9 (consensus)

FIG. 2 shows the increase of GC of the optimized s FlT1sequences relative to the unoptimized.

FIG. 3 shows the nucleotide sequence of chimeric AAV 2.5 vector (SEQ ID NO: 10).

FIG. 4 shows the nucleotide sequence of wildtype AAV 1 capsid (SEQ ID NO: 11).

FIG. 5 shows the nucleotide sequence of modified AAV 1.1 capsid wherein amino acid residue 265 is deleted (SEQ ID NO: 12).

FIG. 6 shows the nucleotide sequence of wildtype AAV 6 capsid (SEQ ID NO: 13).

FIG. 7 shows the nucleotide sequence of modified AAV 6.1 capsid wherein amino acid residue 265 is deleted (SEQ ID NO: 14).

FIG. 8 shows the nucleotide sequence of modified AAV 6.3.1 capsid wherein amino acid residue 265 is deleted and amino acid residue 531 is changed from a Lys to a Glu (SEQ ID NO: 15).

FIG. 9 shows the sequences of vectors, that being, nucleotides 738 to 1634 of sequenced defined in FIGS. 4 to 8, respectively, SEQ ID NO: 16 (AAV1c wildtype), SEQ ID NO: 17 (AAV1/265del ); SEQ ID NO: 18 (AAV6c wildtype); SEQ ID NO: 19 (AAV6/265del ); and SEQ ID NO: 20 (AAV6/265del /K531E) and consensus sequence (SEQ ID NO: 21). (SEQ ID NO: 21).

FIG. 10 shows the expression results for sFlt1 for one non-optimized and seven (7) optimized genes by different optimization algorithms and compared to an unoptimized gene sequence (SEQ ID NO: 1 to 8).

DETAILED DESCRIPTION OF THE INVENTION

Definitions

Figure 11:
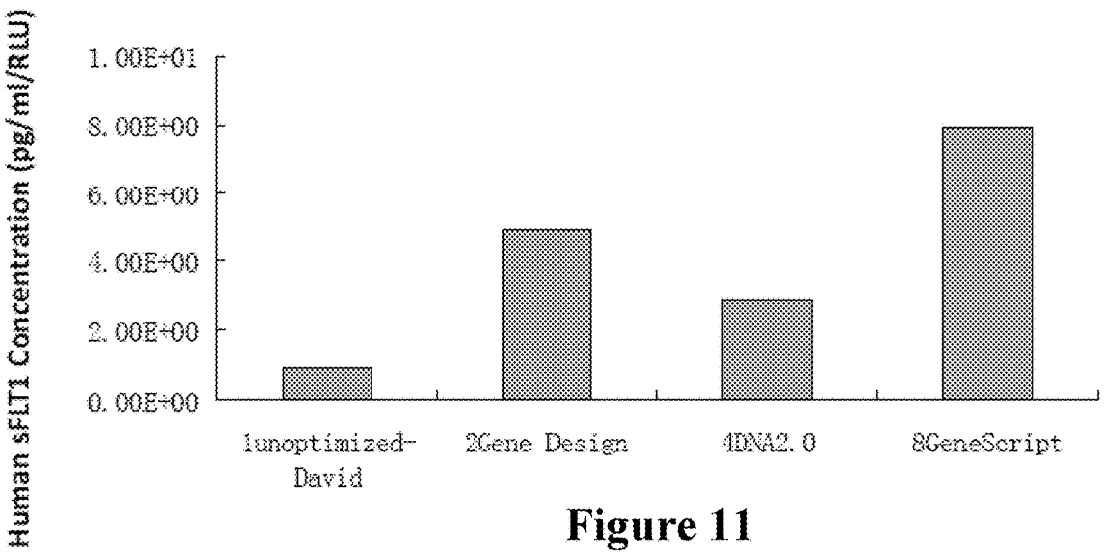
FIG. 11 shows the expression results for sFlt1 in a serum medium for three of the optimized genes and a graph showing the concentration of the expressed proteins compared to an unoptimized gene sequence.

Unless otherwise defined, all technical and scientific terms used herein have the meaning commonly understood by one of ordinary skill in the art to which this invention belongs. The terminology used herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. The following terms have the meanings given:

"AAV Cap" means AAV Cap proteins, VP1, VP2 and VP3 and analogs thereof.

"AAV Rep" means AAV Rep proteins and analogs thereof

"AAV TR" means a palindromic sequence, comprising mostly complementary, symmetrically arranged sequences, and includes analogs of native AAV TRs and analogs thereof.

"Biologically-effective" with respect to an amount of a viral vector is an amount that is sufficient to result in infection (or transduction) and expression of the transgene in a target cell.

"Cis-motifs" includes conserved sequences such as found at or close to the termini of the genomic sequence and recognized for initiation of replication; cryptic promoters or sequences at internal positions likely used for transcription initiation or termination.

"Chimeric" means, with respect to a viral capsid or particle, that the capsid or particle includes sequences from different parvoviruses, preferably different AAV serotypes, as described in Rabinowitz et al., U.S. Pat. No. 6,491,907, entitled "Recombinant parvovirus vectors and method of making," granted on Dec. 10, 2002, the disclosure of which is incorporated in its entirety herein by reference. A particularly preferred chimeric viral capsid is the AAV2.5 capsid, which has the sequence of the AAV2 capsid with the following mutations: 263 Q→A; 265 insertion T; 705 N→A; 708 V→A; and 716 T→N. wherein the nucleotide sequence expressing such capsid is defined as SEQ ID NO: 8.

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., TRs), indicates that one element is located 5' to the sequence and the other is located 3' to the sequence; however, there may be intervening sequences therebetween.

Polynucleotide" means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

"Transduction" of a cell by a virus means that there is transfer of DNA or RNA from the virus particle to the cell.

"Transfection" of a cell means that genetic material is introduced into a cell for the purpose of genetically modifying the cell. Transfection can be accomplished by a variety of means known in the art, such as transduction or electroporation.

"Polypeptide" encompasses both peptides and proteins, unless indicated otherwise.

"Transgene" is used in a broad sense to mean any heterologous nucleotide sequence incorporated in a viral vector for expression in a target cell and associated expression control sequences, such as promoters. It is appreciated by those of skill in the art that expression control sequences will be selected based on ability to promote expression of the transgene in the target cell. An example of a transgene is a nucleic acid encoding a therapeutic polypeptide.

"Vector," means a recombinant plasmid or virus that comprises a polynucleotide to be delivered into a host cell, either in vitro or in vivo.

"Recombinant" means a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

"Recombinant viral vector" means a recombinant polynucleotide vector comprising one or more heterologous sequences (i.e., polynucleotide sequence not of viral origin). In the case of recombinant parvovirus vectors, the recombinant polynucleotide is flanked by at least one, preferably two, inverted terminal repeat sequences (ITRs) that have been known to provide high-level persistent nucleic acid expression.

"Serotype" with respect to vector or virus capsid is defined by a distinct immunological profile based on the capsid protein sequences and capsid structure.

"Peptide", "polypeptide" and "protein" are used interchangeably to denote a sequence polymer of at least two amino acids covalently linked by an amide bond.

"Homologous" used in reference to peptides, refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 50% identical, and preferably at least 75% and more preferably 95% homology to the reference peptide. Additional peptide sequence modification are included, such as minor variations, deletions, substitutions or derivitizations of the amino acid sequence of the sequences disclosed herein, so long as the peptide has substantially the same activity or function as the unmodified peptides. Derivatives of an amino acid may include but not limited to trifluoroleucine, hexafluoroleucine, 5,5,5-trifluoroisoleucine, 4,4,4-trifluorovaline, p-fluorophenylaline, o-fluorotyrosine, m-fluorotyrosine, 2,3-difluorotyrosine, 4-fluorohistidine, 2-fluorohistidine, 2,4-difluorohistidine, fluoroproline, difluoroproline, 4-hydroxyproline, selenomethionine, telluromethionine, selenocysteine, selenatryptophans, 4-aminotryptophan, 5-aminotryptophan, 5-hydroxytryptophan, 7-azatryptophan, 4-fluorotryptophan, 5-fluorotryptophan, 6-fluorotryptophan, homoallylglycine, homopropargylglycine, 2-butynylglycine, cis-crotylglycine, allylglycine, dehydroleucine, dehydroproline, 2-amino-3-methyl-4-pentenoic acid, azidohomoalanine, asidoalanine, azidonorleucine, p-ethynylphenylalanine, p-azidophenylalanine, p-bromophenylalanine, p-acetylphenylalanine and benzofuranylalanine Notably, a modified peptide will retain activity or function associated with the unmodified peptide, the modified peptide will generally have an amino acid sequence "substantially homologous" with the amino acid sequence of the unmodified sequence.

The invention provides modified nucleic acids encoding sFlt1. The invention also provides nucleic acid constructs which include as part of their sequence the modified nucleic acid encoding sFlt1. For example, the invention includes plasmids and/or other vectors that include the modified sFlt1 sequence along with other elements, such as regulatory elements. Further, the invention provides packaged gene delivery vehicle, such as a viral capsid, including the modified sFlt1 sequence. The invention also includes methods of expressing sFlt1 by delivering the modified sequence into a cell along with elements required to promote expression in the cell. The invention also provides gene therapy methods in which the modified sFlt1 sequence is administered to a subject, e.g., as a component of a vector and/or packaged as a component of a viral gene delivery vehicle. Treatment may, for example, be effected to reduce angiogenesis in retina tissue. Each of these aspects of the invention is discussed further in the ensuing sections.

Modified Nucleic Acid for Expression of sFlt1

The invention provides a modified sequence encoding sFlt1. The modified sequence includes the native sFlt1 sequence including one or more optimizing modifications. Examples of optimizing modifications include elimination of one or more cis-acting motifs and introduction of one or more Kozak sequences. In one embodiment, one or more cis-acting motifs are eliminated and one or more Kozak sequences are introduced.

Examples of cis acting motifs that may be eliminated include internal TATA-boxes; chi-sites; ribosomal entry sites; AT-rich and/or GC-rich sequence stretches; ARE, INS, and/or CRS sequence elements; repeat sequences and/or RNA secondary structures; (cryptic) splice donor and/or acceptor sites, branch points; and SalI. Preferably, GC content is enhanced relative to wild-type sFlt1 and one or more cis-acting motifs are removed. The GC content is preferably at least 20 to 90% greater than the wild type gene. Additionally, the codon adaptation index is preferably >75, >80, >85, >90, or >95.

The modified sFlt1 sequence may also include flanking restriction sites to facilitate subcloning into expression vector.

The invention includes a nucleic acid vector including the modified sFlt1 sequence and various regulatory elements. The precise nature of regulatory elements useful for gene expression will vary from organism to organism. In general, they include a promoter which directs the initiation of RNA transcription in the cell of interest. The promoter may be constitutive or regulated. Constitutive promoters are those which cause an operably linked gene to be expressed essentially at all times. Regulated promoters are those which can be activated or deactivated. Regulated promoters include inducible promoters, which are usually "off" but which may be induced to turn "on," and "repressible" promoters, which are usually "on" but may be turned "off." Many different regulators are known, including temperature, hormones, cytokines, heavy metals and regulatory proteins. The distinctions are not absolute; a constitutive promoter may often be regulated to some degree. In some cases an endogenous pathway may be utilized to provide regulation of the transgene expression, e.g., using a promoter that is naturally downregulated when the pathological condition improves.

Examples of suitable promoters include adenoviral promoters, such as the adenoviral major late promoter; heterologous promoters, such as the cytomegalovirus (CMV) promoter; the respiratory syncytial virus promoter; the Rous Sarcoma Virus (RSV) promoter; the albumin promoter; inducible promoters, such as the Mouse Mammary Tumor Virus (MMTV) promoter; the metallothionein promoter; heat shock promoters; the α-1-antitrypsin promoter; the hepatitis B surface antigen promoter; the transferrin promoter; the apolipoprotein A-1 promoter; and human sFlt1 promoters. The promoter may be a tissue-specific promoter, such as the mouse albumin promoter, which is active in liver cells as well as the transthyretin promoter (TTR).

Packaged Modified sFlt1Sequence

The modified sFlt1 sequence may also be provided as a component of a packaged viral vector. In general, packaged viral vectors include a viral vector packaged in a capsid. Viral vectors and viral capsids are discussed in the ensuing sections.

Viral Vector

The viral vector component of the packaged viral vectors produced according to the methods of the invention includes at least one modified sFlt1 sequence and associated expression control sequences for controlling expression of the modified sFlt1 sequence. The viral vector may include cis-acting functions sufficient to enable persistence as episomal forms or by mechanisms including integration of the modified sFlt1 sequence into the genome of a target cell.

In a preferred embodiment, the viral vector includes a portion of a parvovirus genome, such as an AAV genome with rep and cap deleted and replaced by the modified sFlt1 sequence and its associated expression control sequences. The modified sFlt1 sequence is typically inserted adjacent to one or two (i.e., flanked by) AAV TRs or TR elements adequate for viral replication; Xiao et al., J Virol 71; 2: 941-948 (1997), in place of the viral rep and cap ORFs. Other regulatory sequences suitable for use in facilitating tissue-specific expression of the modified sFlt1 sequence in the target cell may also be included.

The viral vector may be any suitable nucleic acid construct, such as a DNA or RNA construct and may be single stranded, double stranded, or duplexed.

Viral Capsid

The viral capsid component of the packaged viral vectors may be a parvovirus capsid. AAV Cap and chimeric capsids are preferred. Examples of suitable parvovirus viral capsid components are capsid components from the family Parvoviridae, such as an autonomous parvovirus or a Dependovirus. For example, the viral capsid may be an AAV capsid (e.g., AAV1, AAV2, AAV3, AAV4, AAV5, AAV6, AAV7, AAV8 AAV 9, AAV10, AAV 11 or AAV12 capsid; one skilled in the art would know there are likely other variants not yet identified that perform the same or similar function), or may include components from two or more AAV capsids.

A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences AAV Caps from two or more viruses, preferably two or more AAVs, as described in Rabinowitz et al., U.S. Pat. No. 6,491,907, entitled "Recombinant parvovirus vectors and method of making," granted on Dec. 10, 2002, the entire disclosure of which is incorporated herein by reference. For example, the chimeric virus capsid can include an AAV1 Cap protein or subunit and at least one AAV2 Cap or subunit. The chimeric capsid can, for example, include an AAV capsid with one or more B19 Cap subunits of human parvovirus, e.g., an AAV Cap protein or subunit can be replaced by a B19 Cap protein or subunit. For example, in a preferred embodiment, the Vp3 subunit of the AAV capsid can be replaced by the Vp2 subunit of B19.

Production of Packaged Viral Vector

The invention includes packaging cells which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Viral Vector Functions

The packaging cells of the invention include viral vector functions, along with packaging and vector functions. The viral vector functions typically include a portion of a parvovirus genome, such as an AAV genome, with rep and cap deleted and replaced by the modified sFlt1 sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide. The viral vector may be any suitable nucleic acid construct, such as a DNA or RNA construct and may be single stranded, double stranded, or duplexed.

The viral vector functions may suitably be provided as duplexed vector templates, as described in U.S. Patent Publication No. 2004/0029106 to Samulski et al. (the entire disclosure of which is incorporated herein by reference for its teaching regarding duplexed vectors). Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded genome normally encapsidated by the virus.

The TR(s) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1-AAV12 and other novel capsids as yet unidentified or from non human primate sources. Capsid components may include components from two or more AAV capsids, providing a chimeric AAV.

In a more preferred embodiment, one or more of the VP capsid proteins is a chimeric protein, comprising amino acid sequences from two or more viruses, preferably two or more AAVs, as described in Rabinowitz et al., U.S. Pat. No. 6,491,907, entitled "Recombinant parvovirus vectors and method of making," granted on Dec. 10, 2002, the entire disclosure of which is incorporated in its entirety herein by reference.

For example, the chimeric virus capsid can include a capsid region from an adeno-associated virus (AAV) and at least one capsid region from a B19 virus. The chimeric capsid can, for example, include an AAV capsid with one or more B19 capsid subunits, e.g., an AAV capsid subunit can be replaced by a B19 capsid subunit. For example, in a preferred embodiment, the VP1, VP2 or VP3 subunit of the AAV capsid can be replaced by the VP1, VP2 or VP3 subunit of B19. As another example, the chimeric capsid may include an AAV type 2 capsid in which the type 2 VP1 subunit has been replaced by the VP1 subunit from an AAV type 1, 3, 4, 5, or 6 capsid, preferably a type 3, 4, or 5 capsid. Alternatively, the chimeric parvovirus has an AAV type 2 capsid in which the type 2 VP2 subunit has been replaced by the VP2 subunit from an AAV type 1, 3, 4, 5, or 6 capsid, preferably a type 3, 4, or 5 capsid. Likewise, chimeric parvoviruses in which the VP3 subunit from an AAV type 1, 3, 4, 5 or 6 (more preferably, type 3, 4 or 5) is substituted for the VP3 subunit of an AAV type 2 capsid are preferred. As a further alternative, chimeric parvoviruses in which two of the AAV type 2 subunits are replaced by the subunits from an AAV of a different serotype (e.g., AAV type 1, 3, 4, 5 or 6) are preferred. In exemplary chimeric parvoviruses according to this embodiment, the VP1 and VP2, or VP1 and VP3, or VP2 and VP3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

The packaged viral vector generally includes the modified sFlt1 sequence and expression control sequences flanked by TR elements sufficient to result in packaging of the vector DNA and subsequent expression of the modified sFlt1 sequence in the transduced cell. The viral vector functions may, for example, be supplied to the cell as a component of a plasmid or an amplicon. The viral vector functions may exist extrachromosomally within the cell line and/or may be integrated into the cells' chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

Packaging Functions

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon. The packaging functions may exist extrachromosomally within the packaging cell, but are preferably integrated into the cell's chromosomal DNA. Examples include genes encoding AAV Rep and Cap proteins.

Helper Functions

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. The packaging functions may exist extrachromosomally within the packaging cell, but are preferably integrated into the cell's chromosomal DNA.

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Packaging Cell

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, 293 cells, B-50 or any other HeLa cells, HepG2, Saos-2, HuH7, and HT1080 cell lines.

Preferred cell lines for use as packaging cells are insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, NJ (1995); O'Reilly et al., Baculovirus Expression Vectors: A Laboratory Manual, Oxford Univ. Press (1994); Samulski et al., J. Vir. 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.* 219:37-44 (1996); Zhao et al., *Vir.* 272:382-93 (2000); and Samulski et al., U.S. Pat. No. 6,204,059.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA.

Treatment Methods

The modified sFlt1 gene may be used for gene therapy of ocular neovascularization diseases, such as macular degeneration. An individual may be in need of gene therapy for clinical management of angiogenesis in the retina. Further the present invention may include treatment for visual loss caused by macular edema and evident in subjects with diabetes, uveitis and after cataract surgery.

In particular embodiments, the present invention provides a pharmaceutical composition comprising a vector of the present invention including a modified gene of sFlt1 in a pharmaceutically-acceptable carrier and/or other medicinal agents, pharmaceutical agents, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material.

A pharmaceutical composition may be used, for example, in transfection of a cell ex vivo or in administering a viral vector or cell directly to a subject.

Recombinant virus vectors comprising the modified gene of sFlt1 are preferably administered to the cell in a biologically-effective amount. If the virus vector is administered to a cell in vivo (e.g., the virus is administered to a subject as described below), a biologically-effective amount of the virus vector is an amount that is sufficient to result in transduction and expression of the transgene in a target cell and in an amount to reduce the activity of VEGF.

A further aspect of the invention is a method of treating subjects in vivo with the vector containing modified genes. Administration of the vector to a human subject or an animal in need thereof can be by any means known in the art for administering virus vectors.

Exemplary modes of administration include intravenous, subcutaneous, intradermal, intramuscular, and intraarticular administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

Dosages of the inventive virus vector with the modified sFlt1 gene will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

The modified sFlt1 gene may be administered as components of a DNA molecule having regulatory elements appropriate for expression in the target cells. The modified sFlt1 gene may be administered as components of viral plasmids, such as rAAV vectors. Viral particles may be administered as viral particles alone, whether as an in vivo direct delivery to the portal vasculature or as an ex vivo treatment comprising administering the vector viral particles in vitro to cells from the animal receiving treatment followed by introduction of the transduced cells back into the donor.

Examples

Expression of the Proteins

The novel and unique optimized gene sequences of SEQ ID NOs: 2 to 8 were created by seven different and distinct methods of optimization and were then subsequently expressed. As shown in FIG. 10, the different sequences provided for very different results in three separate assays used to determine the level of protein expression. Using the unoptimized gene sequence as the control for the ELISA/Luc assay, then each optimized gene sequence expressed different amounts of the specific sFlt1 protein. Thus, the optimized sequences are each novel and the clearly it is not known as to which will provide for the optimal amount of the expressed sFlt1 protein.

FIG. 11 provides further indication of the diversity of different optimized gene sequences and the expression thereof wherein SEQ ID NO: 8 (GeneScript) provided the highest concentration of expression. Further, it should be noted that the medium used for expression of the proteins is different from that used in FIG. 10.

Figure 12:
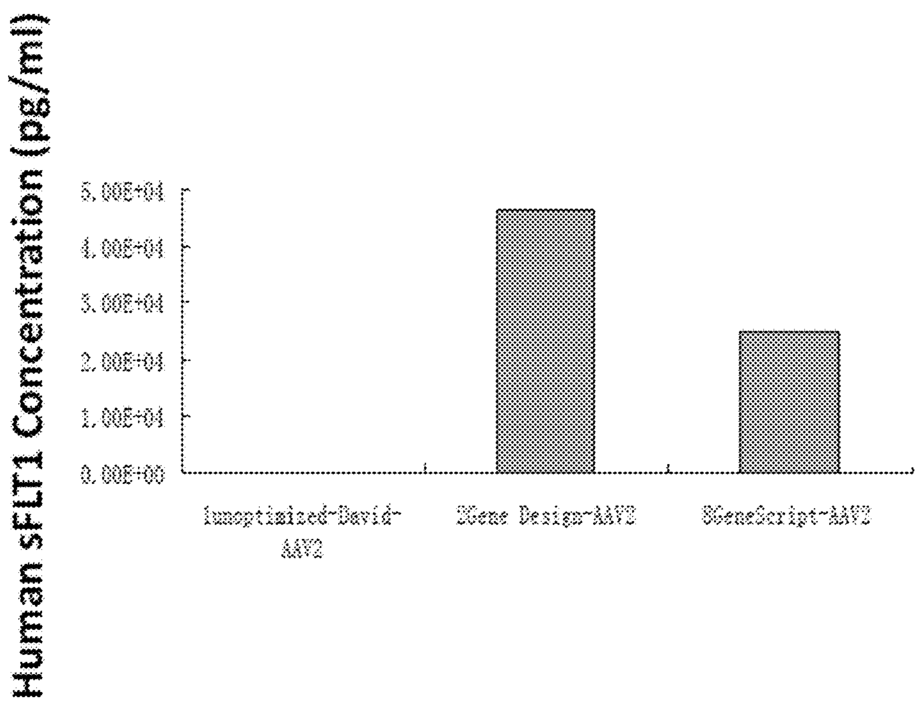
FIG. 12 shows the expression results for sFlt1 for two of the optimized genes and a graph showing the concentration of the expressed proteins compared to an unoptimized gene sequence.

Using AAV2 carrying optimized genes vs. wild type sFlt1 coding sequence, side-by-side expression analysis was carried out in vitro (FIG. 12) and ELISA was used to determine the total amount of sFlt1 protein. Based on these studies it is clear that the optimized sFlt1 genes, that being SEQ ID NO: 2 and SEQ ID NO: 8, expressed significantly more sFlt1 protein product when compared to the unoptimized coding sequence when delivered at the same dose.

In Vivo Testing

Notably the mouse retina can be used as a tool to investigate conditions in which normal vascular development becomes unbalanced, leading to sight-threatening diseases, as occurs in human retinopathy of prematurity (ROP). Thus, successful modeling of human ROP in this animal model can replicate the phases of ROP including neovascularization (NV)—along with some of the more frequent complications like vascular leakage. Oxygen-induced retinopathy (OIR) was induced in the testing mice by exposure to increased levels of oxygen for about four days postnatal and then returned to normal oxygen content of about 20%. On P4, three specific vectors were injected into the eyes of the testing mice in an amount of about 0.5 microliters using a sharp needle. Also a control group was included wherein no injection was administered. The vectors included AAV2-sFlt1 unoptimized (SEQ ID NO: 1), AAV2-OPT-2 (SEQ ID NO: 2, GeneDesign) and AAV2-OPT-8 (SEQ ID NO: 8, GeneScript) and a control wherein no sFlt1 was introduced. On P17 the different levels of concentration of expressed sFlt1 were measured by removing the eyes wherein the retina was dissected and cut radially into four quadrants and mounted for examination by fluorescence. The total neovascular area was determined relative to the total retina and then compared to the control.

Figure 13:
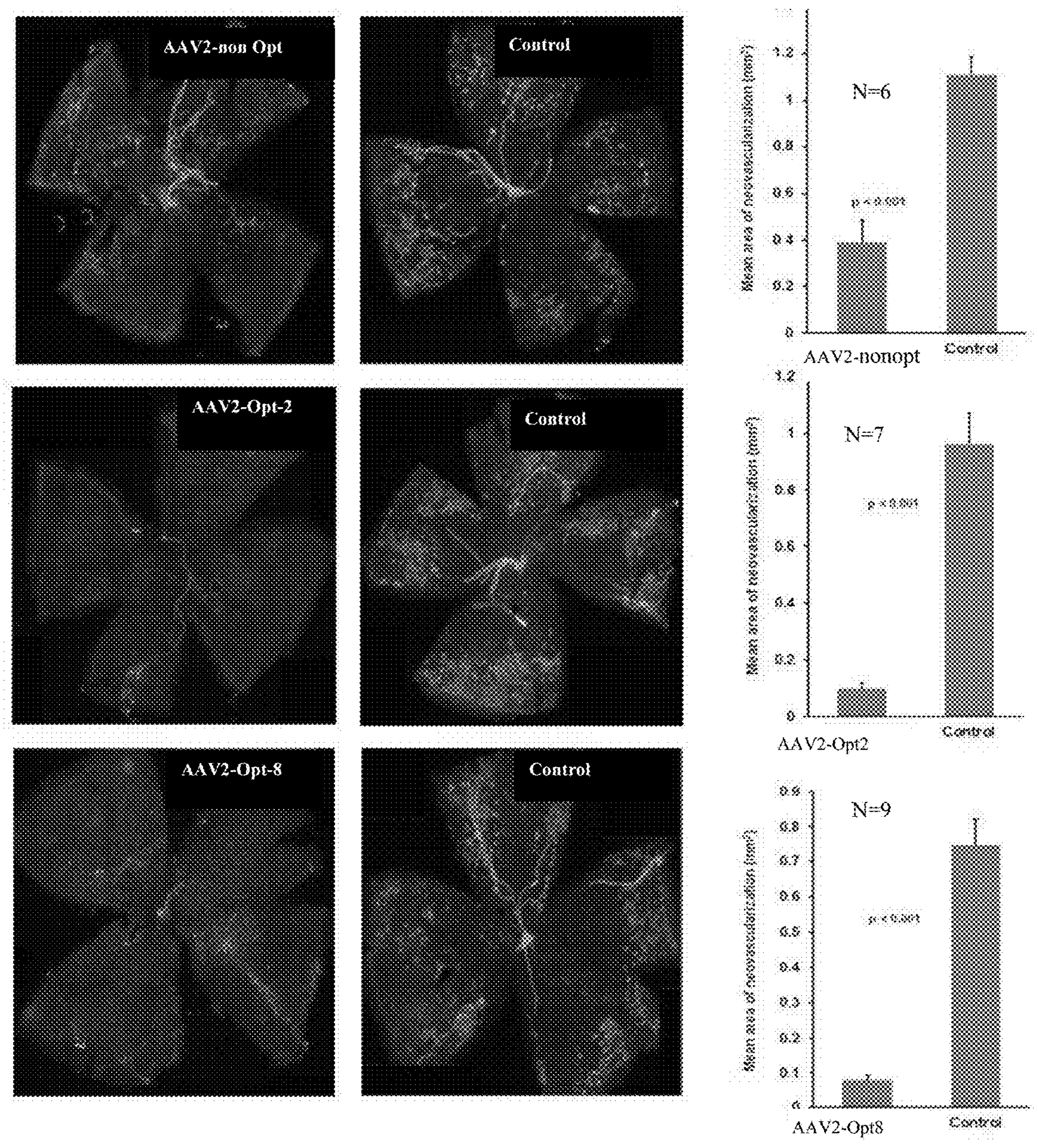
FIG. 13 shows photographs of neovascularization of retina tissue when administering the non-optimized gene sequence (SEQ ID NO: 1) and two of the optimized sequences (SEQ ID NO: 2 and 8) included in AAV2 (SEQ ID NO: 22) The control included no sequences for sFlt1 (SEQ ID NO: 23). The graph provides values for the mean area of neovascularization taken from the grouping of testing animals.

FIG. 13 shows that using the AAV2-nonoptimized sFlt1 gene (Seq ID NO: 1) showed a mean area of neovascularization of about 0.4 $mm^2$ while the control (no sFLT1) was about 1.1 $mm^2$. Using the AAV2-Opt-2 vector (SEQ ID NO: 2) it was found that the optimized gene expressed more sFlt1 and this is evident because the mean area of neovascularization was reduced to out 0.1 $mm^2$ while the control showed a mean area of neovascularization of about 1.00 $mm^2$. Using the vector AAV2-Opt-8 (SEQ ID NO: 8) provided for increased expression of sFlt1 and a mean area of neovascularization of approximately 0.09 $mm^2$ with a control of about 0.85 $mm^2$. Clearly the optimized genes expressing sFlt1 provided for increased levels of expression causing a surprising and unexpected reduction in the area of neovascularization of retina tissue and intensity of fluorescence.

Figure 14:
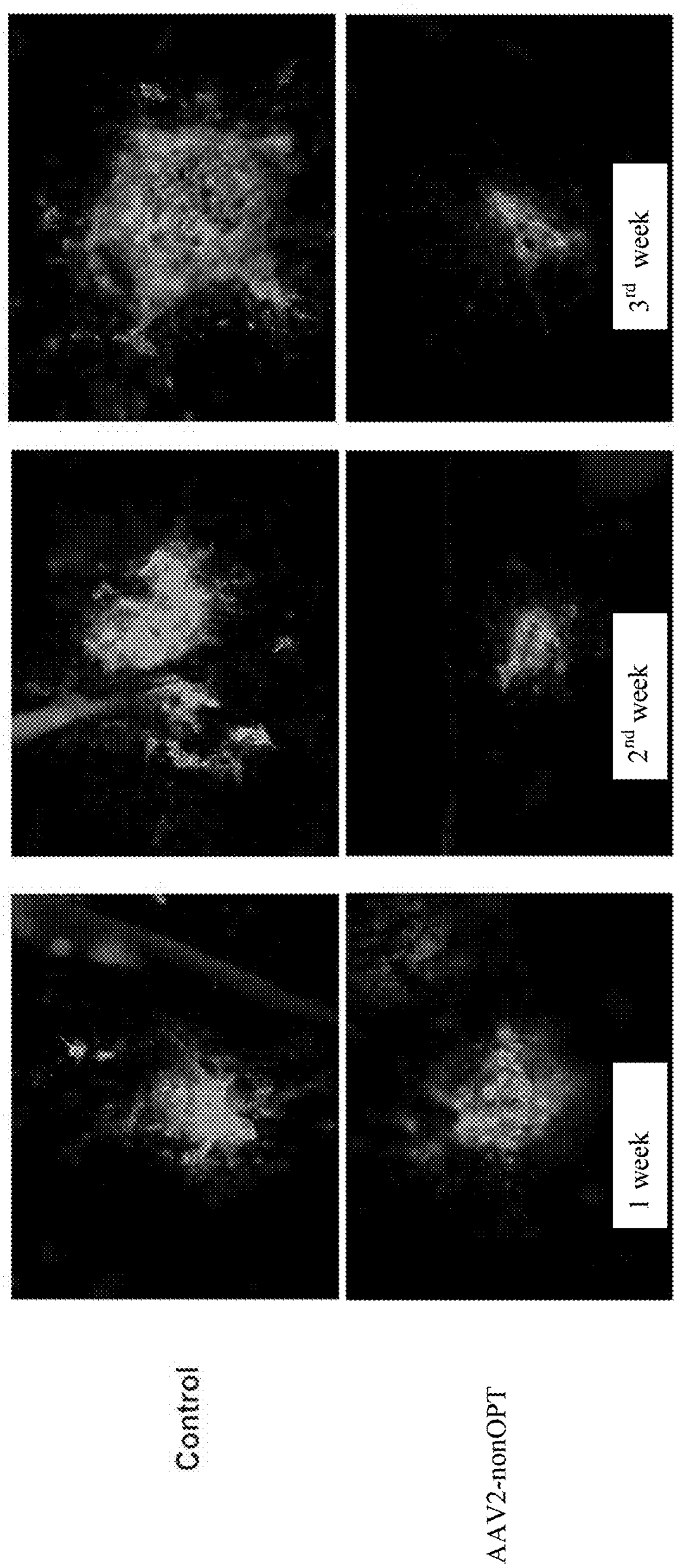
FIG. 14 shows photographs and the leakage caused by laser photocoagulation and the increase in leakage in the control (SEQ ID NO: 23) and reduction when included non-optimized sFlt1 (SEQ ID NO: 1) over the testing period.
Figure 15:
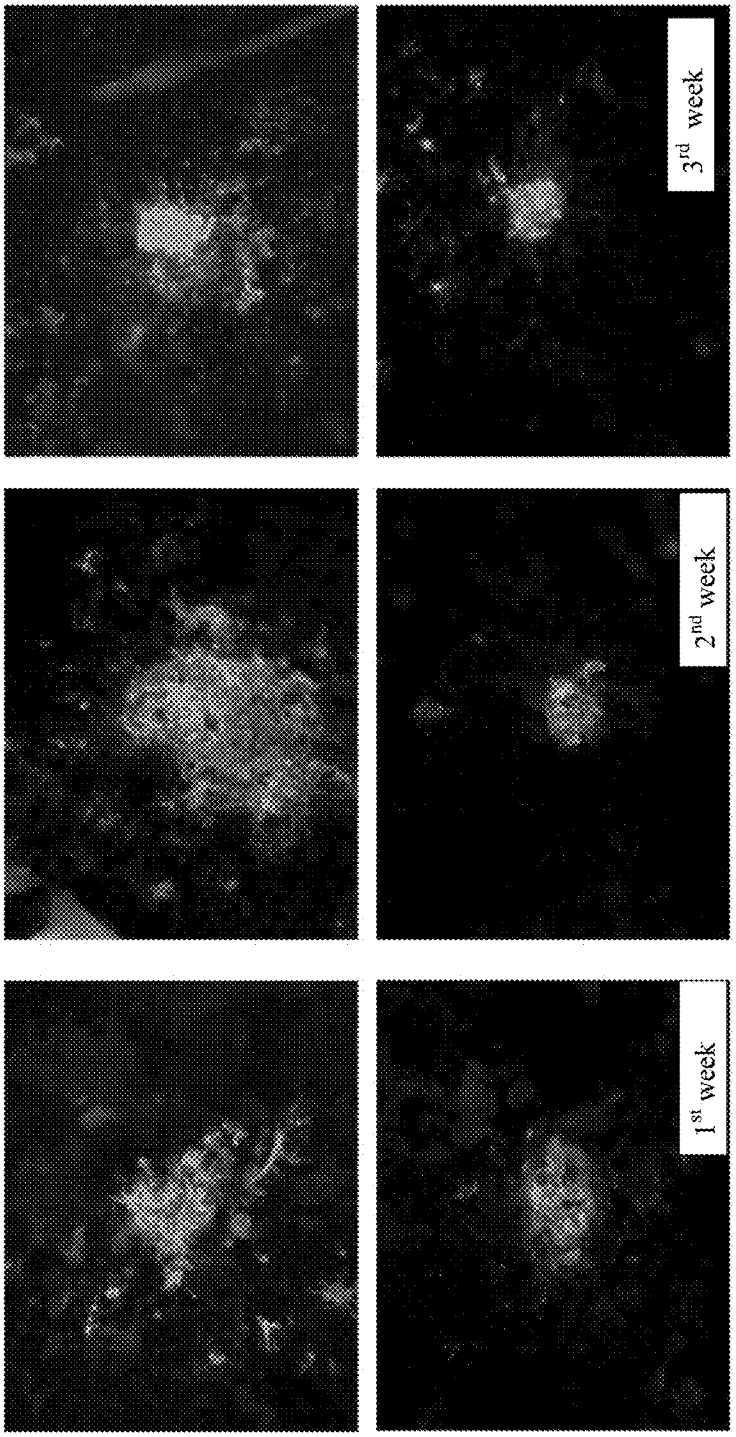
FIG. 15 shows photographs and the leakage caused by laser photocoagulation and the increase in leakage in the control (SEQ ID NO: 23) and reduction when the vector included optimized sFlt1 (Opt-2) (SEQ ID NO: 24, TR: 20 bp-164 bp, 3518 bp-3662 bp; CBh promoter: 385 bp-1199 bp; sFLT-opt2: 1208 bp-2864 bp; SV40 PolyA: 3281 bp-3431 bp)) over the testing period. Notably when the sFlt1 gene was optimized the reduction in damage or leakage is visible when compared to the results of FIG. 14 using a non-optimized gene.
Figure 16:
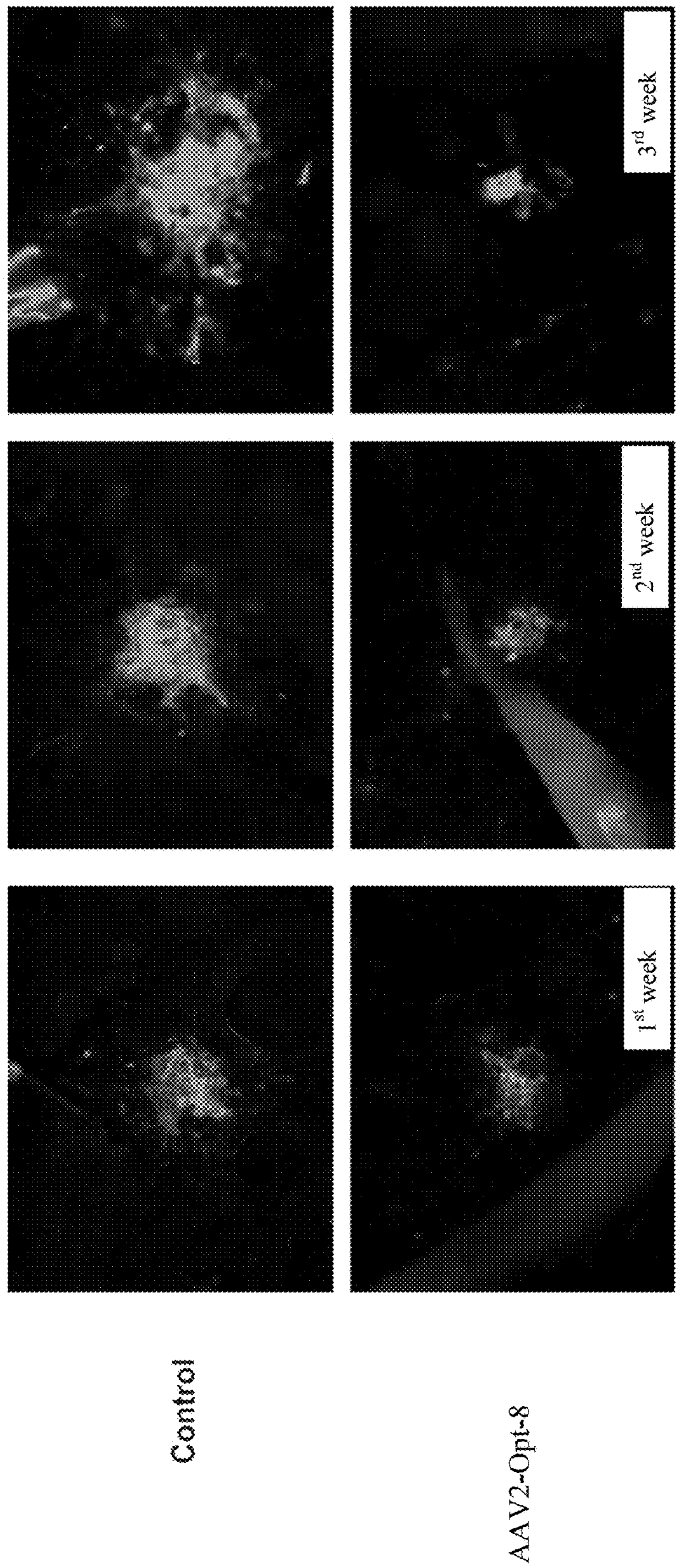
FIG. 16 shows photographs and the leakage caused by laser photocoagulation and the increase in leakage in the control (SEQ ID NO: 23, (TR: 20 bp-164 bp, 3118 bp-3262 bp; CBh promoter: 385 bp-1199 bp; Luciferase cDNA: 1212 bp-2864 bp; SV40 PolyA: 2881 bp-3031 bp)) and reduction when the vector included optimized sFlt1 (Opt-8) (SEQ ID NO: 25) TR: 20 bp-164 bp, 3518 bp-3662 bp, CBh promoter: 385 bp-1199 bp; sFLT-opt 8: 1208 bp-2864 bp; SV40 PolyA: 3281 bp-3431 bp)) over the testing period. Notably when the sFlt1 gene was optimized the reduction in damage or leakage is visible when compared to the results of FIG. 14 using a non-optimized gene.

It was also found that the AAV mediated optimized sFlt1 gene therapy of the present invention reduced and/or prevented laser induced choroidal neovascularization (CNV) in mice. The above described AAV2 vectors, that being AAV2-sFlt1 unoptimized (SEQ ID NO: 1), AVV2-OPT-2 (SEQ ID NO: 2, GeneDesign) and AAV2-OPT-8 (SEQ ID NO: 8, GeneScript) and a control wherein no sFlt1 were introduced by subretinal delivery in an amount of about 0.5 microliters. Two weeks later laser photocoagulation was performed on the mice eyes to create a model for CNV. Seven days after the laser treatment the mice were anesthetized and their pupils were removed. Photographs were taken after the intraperitoneal administration of FITC-GSA-Lectin as a stain. FIGS. 14, 15 and 16 showed that the laser photocoagulation caused leakage in both the controls and the AVV2 vector treated eyes, however leakages was reduced in the AAV2-optimized sFlt1 injected eyes. Importantly in the controls it is evident that the leakage increased while the two optimized treated eyes (FIGS. 15 and 16) showed a reduction of leakage over the period of viewing. AAV-2-Opt-8 showed the greatest reduction in leakage over the period of viewing ($1^{st}$ week, $2^{nd}$ week and $3^{rd}$ week), as shown in FIG. 16.

Figure 17:
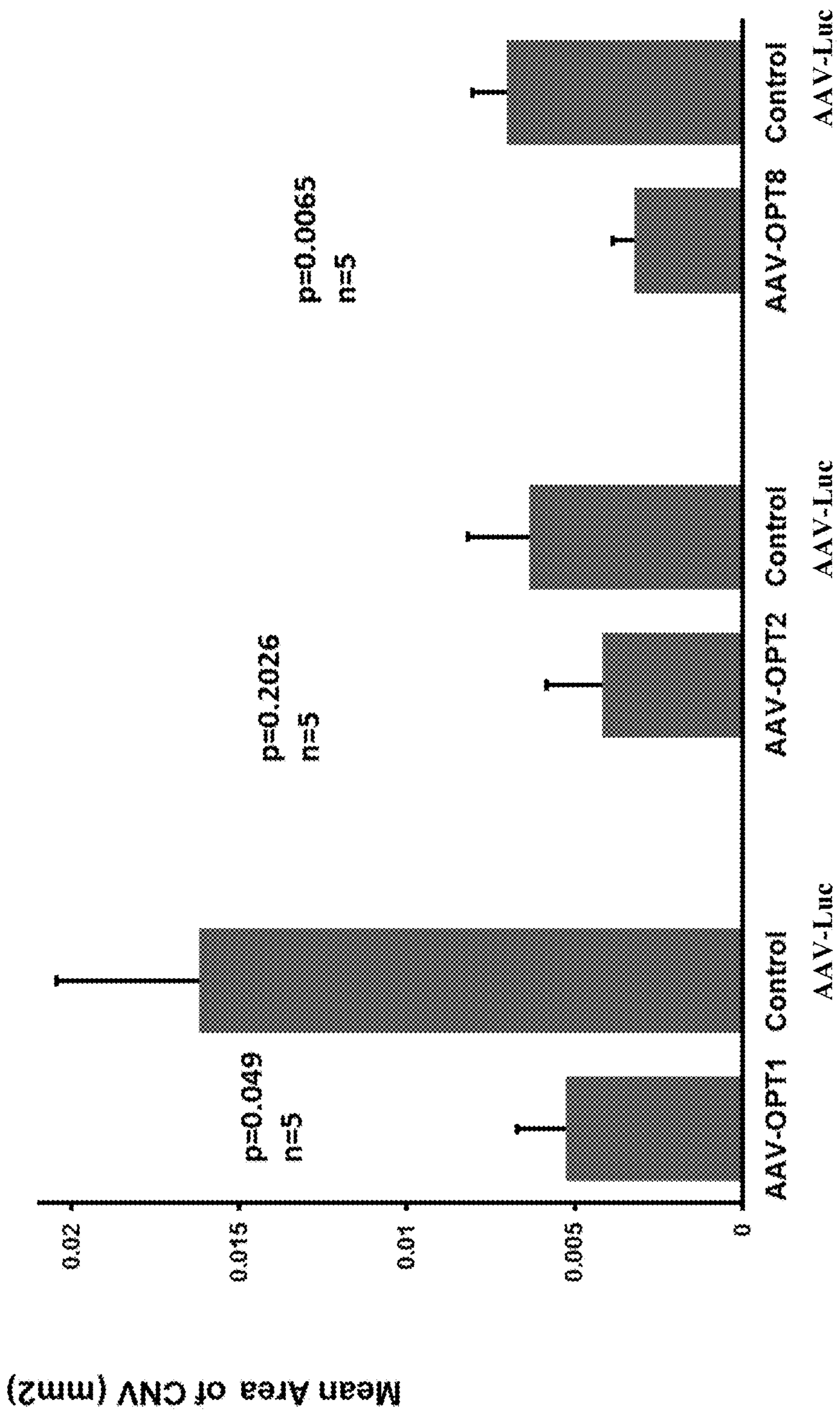
FIG. 17 shows the results compiled from FIGS. 14-16 and measured the mean area of CNV when comparing a control (no sFlt1 gene SEQ ID NO: 23) when compared to the non-optimized gene (SEQ ID NO: 1) and Opt-2 (SEQ ID NO: 24) and Opt-8 (SEQ ID NO: 25) optimized genes.
Figure 19:
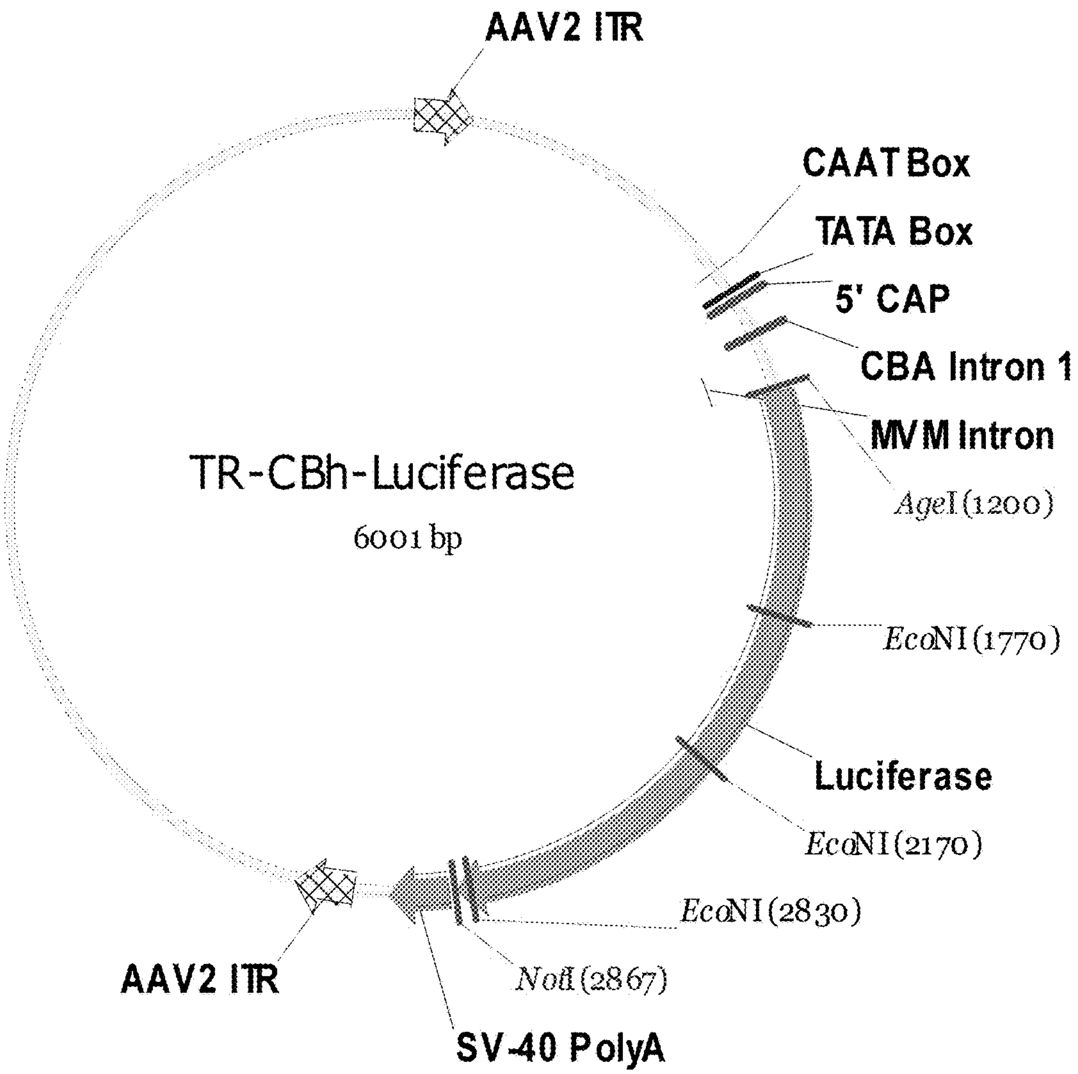
FIG. 19 shows the virus vector construct for the expression of the control Luciferase as shown in SEQ ID NO: 23.
Figure 20:
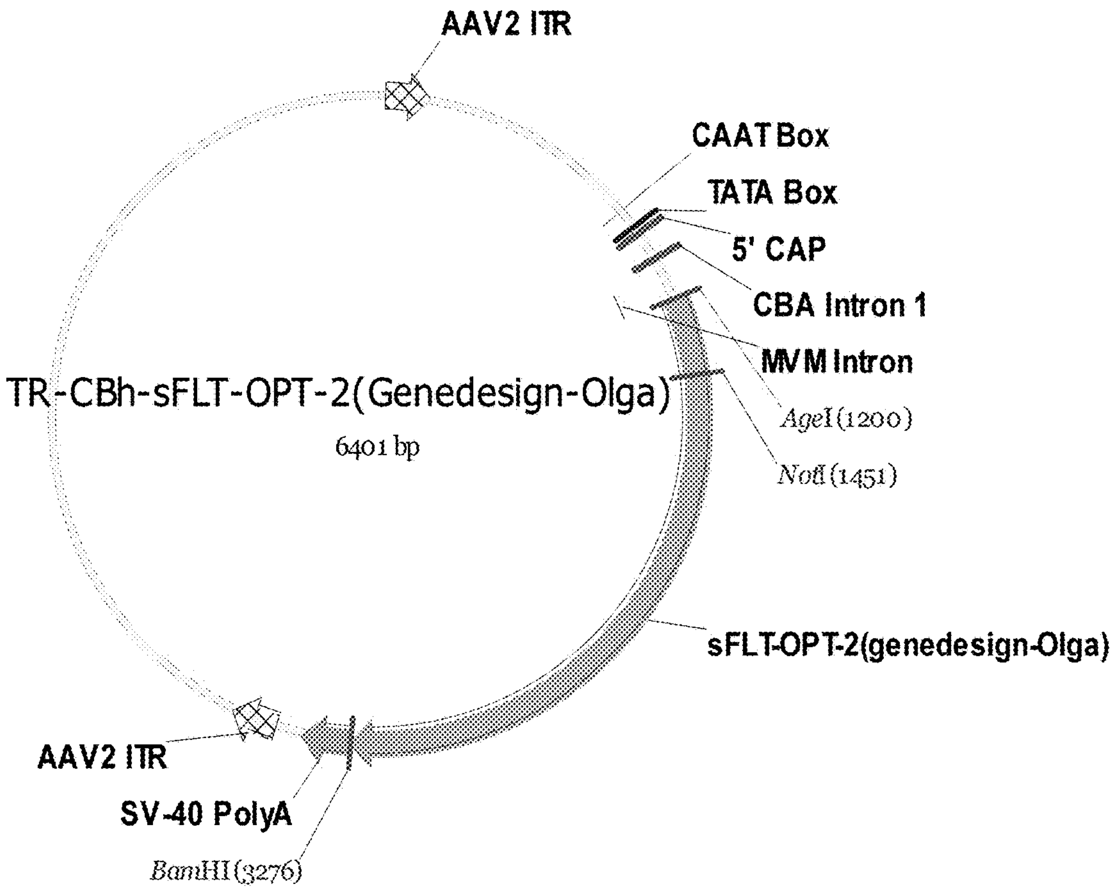
FIG. 20 shows the virus vector construct including the optimized sequence for OPT-2, as shown in SEQ ID NO: 24
Figure 21:
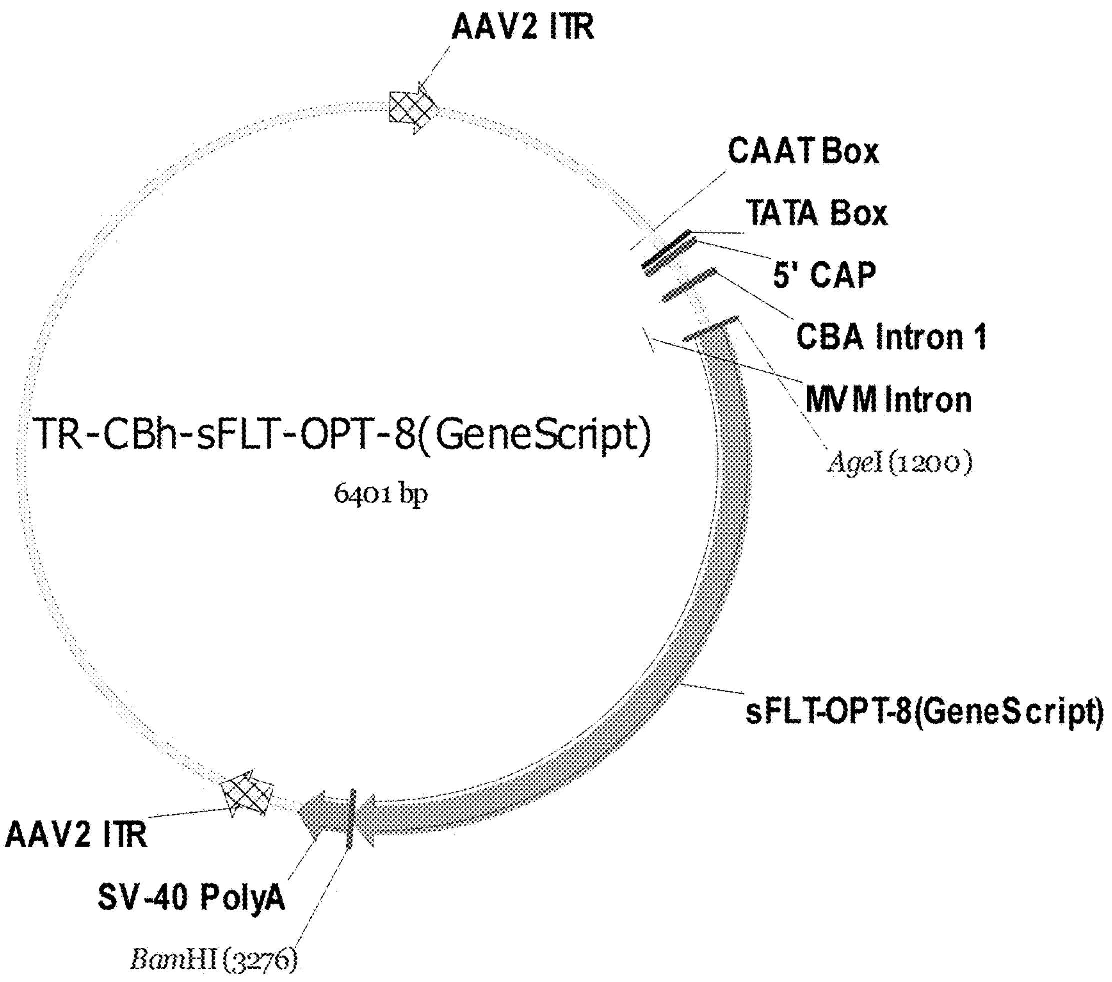
FIG. 21 shows the virus vector construct including the optimized sequence for OPT-8, as shown in SEQ ID NO: 25.

FIG. 17 shows the mean area of CNV for the different groupings of AAV2 vectors (viral vector constructs of FIGS. 20 and 21) compared to the control (viral vector construct of FIG. 19) wherein the testing group includes five mice for each result. Clearly, expression by the AAV2-Opt2 and AAV2-Opt8 genes showed the greatest reduction in area affected by CNV because of a reduced amount of leakage.

Figure 18:
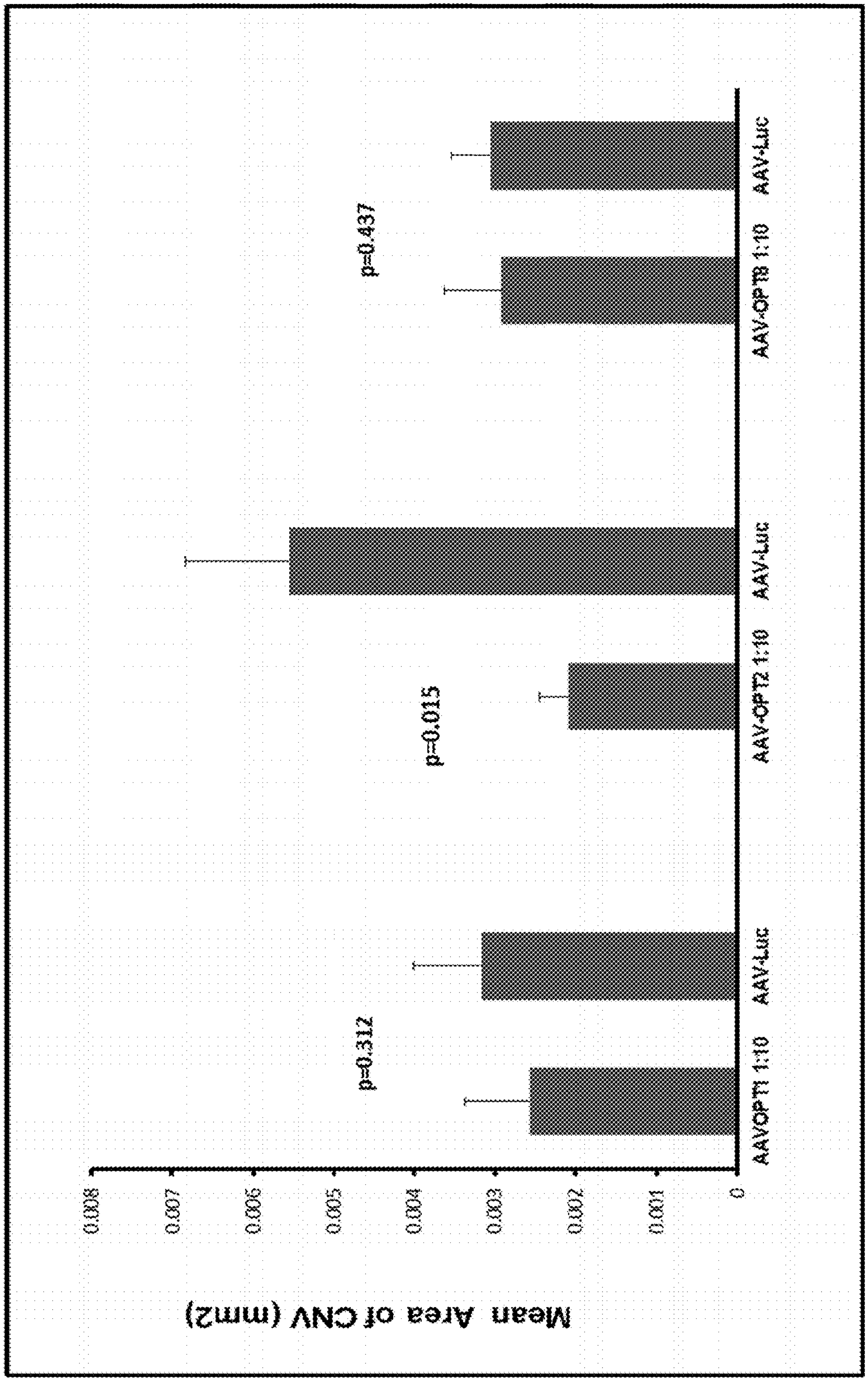
FIG. 18 shows the results when the Opt1 (nonoptimized SEQ ID NO: 1), Opt-2 (SEQ ID NO: 24) and Opt-8 (SEQ ID NO; 25) were diluted 1:10 and administered to the testing animal. The mean area of CNV shows that Opt-2 maintained its effective in reducing CNV when compared to Opt-8 optimized genes and Opt-1 (nonoptimized).

The above test was conducted again wherein the solutions, including the AAV2 vectors, were diluted 10 times and testing results regarding leakage and mean area of CNV is shown in FIG. 18. All three vectors showed some inhibition of CNV, however, AAV2-Opt2 still exhibited substantial inhibition effects.

That which is claimed is:

1. An optimized, modified coding sequence for soluble fms-like tyrosine kinase-1 (sFlt1) for treating an ocular disorder associated with neovascularization in retinal cells in a human subject wherein the optimized, modified coding sequence has increased GC content and reduced cis motifs relative to a wild type sFlt1 coding sequence, wherein the optimized, modified coding sequence has the nucleotide sequence SEQ ID NO: 2, SEQ ID NO: 8, or compliment thereof.

2. A viral vector comprising the optimized, modified coding sequence of claim 1.

3. The viral vector of claim 2, wherein the viral vector is an Adeno-Associated Virus (AAV) vector with a capsid of an AAV selected from the group consisting of AAV1, AAV2, AAV3, AAV4, AAV5, AAV6, AAV7AAV8, AAV9, AAV10, AAV11, AAV12, and combinations thereof.

4. The optimized, modified coding sequence of claim 1, wherein the optimized, modified coding sequence is SEQ ID NO: 8.

5. A pharmaceutical composition comprising an admixture of: an isolated or a purified nucleic acid comprising one of the nucleotide sequences of SEQ ID NO: 2, SEQ ID NO: 8, or a complement thereof; and a pharmaceutically acceptable carrier.

6. A gene therapy treatment for a subject with an ocular disorder causing neovascularization, said treatment comprising directly administering to an eye of the subject a recombinant adeno-associated viral (rAAV) vector comprising an optimized, modified coding sequence for sFlt1 operably linked to a promoter sequence to thereby deliver the vector to retinal cells of the subject, wherein the optimized, modified coding sequence has increased GC content and reduced cis motifs relative to a wild type sFlt1 coding sequence, wherein the optimized, modified coding sequence has the nucleotide sequence of SEQ ID NO: 2, SEQ ID NO: 8, or complements thereof, and wherein the optimized, modified coding sequence is expressed at a level which produces a therapeutically effective amount of sFlt1 in the retinal cells to thereby treat the subject.

7. The gene therapy treatment of claim 6, wherein the rAAV vector has a capsid of an AAV selected from the group consisting of AAV1, AAV2, AAV3, AAV4, AAV5, AAV6, AAV7AAV8, AAV9, AAV10, AAV11, AAV12, and combinations thereof.

8. The gene therapy treatment of claim 6, wherein the optimized, modified sFlt1 coding sequence is flanked by AAV terminal repeats.

9. The gene therapy treatment of claim 6, wherein the optimized, modified coding sequence has the nucleotide sequence of SEQ ID NO: 2 or SEQ ID NO: 8.

10. A process for expressing an optimized, modified sFlt1 peptide in a retinal cell, the process comprising;

directly introducing the optimized, modified coding sequence for sFlt1operably linked to a promoter sequence into the retinal cell under conditions appropriate for expression of the sFlt1, wherein the optimized, modified coding sequence has increased GC content and reduced cis motifs relative to a wild type sFlt1 coding sequence.

11. The process of claim 10, wherein the optimized, modified coding sequence has the nucleotide sequence of SEQ ID NO: 2, SEQ ID NO: 8, or complement thereof.

12. The process of claim 10, wherein the retinal cell is a retinal pigment epithelial cell.

13. The process of claim 10, wherein the reduced cis motifs are due to an elimination of sequences selected from the group consisting of internal TATA-boxes; chi-sites; ribosomal entry sites; AT-rich sequence stretches; INS sequence elements; CRS sequence elements; repeat sequences; RNA secondary structures; (cryptic) splice donor sites; (cryptic) splice acceptor sites; branch points; and Sa1I.

* * * * *

SEQUENCE LISTING

```
<160> NUMBER OF SEQ ID NOS: 26

<210> SEQ ID NO 1
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 1

atggtcagct actgggacac cggggtcctg ctgtgcgcgc tgctcagctg tctgcttctc      60

acaggatcta gttcaggttc aaaattaaaa gatcctgaac tgagtttaaa aggcacccag     120

cacatcatgc aagcaggcca gacactgcat ctccaatgca ggggggaagc agcccataaa     180

tggtctttgc ctgaaatggt gagtaaggaa agcgaaaggc tgagcataac taaatctgcc     240

tgtggaagaa atggcaaaca attctgcagt actttaacct tgaacacagc tcaagcaaac     300

cacactggct tctacagctg caaatatcta gctgtaccta cttcaaagaa gaaggaaaca     360

gaatctgcaa tctatatatt tattagtgat acaggtagac ctttcgtaga gatgtacagt     420

gaaatccccg aaattataca catgactgaa ggaagggagc tcgtcattcc ctgccgggtt     480

acgtcaccta acatcactgt tactttaaaa aagtttccac ttgacacttt gatccctgat     540

ggaaaacgca taatctggga cagtagaaag ggcttcatca tatcaaatgc aacgtacaaa     600

gaaatagggc ttctgacctg tgaagcaaca gtcaatgggc atttgtataa gacaaactat     660

ctcacacatc gacaaaccaa tacaatcata gatgtccaaa taagcacacc acgcccagtc     720

aaattactta gaggccatac tcttgtcctc aattgtactg ctaccactcc cttgaacacg     780

agagttcaaa tgacctggag ttaccctgat gaaaaaaata agagagcttc cgtaaggcga     840

cgaattgacc aaagcaattc ccatgccaac atattctaca gtgttcttac tattgacaaa     900

atgcagaaca aagacaaagg actttatact tgtcgtgtaa ggagtggacc atcattcaaa     960

tctgttaaca cctcagtgca tatatatgat aaagcattca tcactgtgaa acatcgaaaa    1020

cagcaggtgc ttgaaaccgt agctggcaag cggtcttacc ggctctctat gaaagtgaag    1080

gcatttccct cgccggaagt tgtatggtta aaagatgggt tacctgcgac tgagaaatct    1140

gctcgctatt tgactcgtgg ctactcgtta attatcaagg acgtaactga agaggatgca    1200

gggaattata caatcttgct gagcataaaa cagtcaaatg tgtttaaaaa cctcactgcc    1260

actctaattg tcaatgtgaa accccagatt tacgaaaagg ccgtgtcatc gtttccagac    1320

ccggctctct acccactggg cagcagacaa atcctgactt gtaccgcata tggtatccct    1380

caacctacaa tcaagtggtt ctggcacccc tgtaaccata atcattccga agcaaggtgt    1440

gacttttgtt ccaataatga agagtccttt atcctggatg ctgacagcaa catgggaaac    1500

agaattgaga gcatcactca gcgcatggca ataatagaag gaaagaataa gatggctagc    1560
```

```
accttggttg tggctgactc tagaatttct ggaatctaca tttgcatagc ttccaataaa   1620

gttgggactg tgggaagaaa cataagcttt tatatcacag atgtgccaaa tgggtttcat   1680

gttaacttgg aaaaaatgcc gacggaagga gaggacctga aactgtcttg cacagttaac   1740

aagttcttat acagagacgt tacttggatt ttactgcgga cagttaataa cagaacaatg   1800

cactacagta ttagcaagca aaaaatggcc atcactaagg agcactccat cactcttaat   1860

cttaccatca tgaatgtttc cctgcaagat tcaggcacct atgcctgcag agccaggaat   1920

gtatacacag ggaagaaat cctccagaag aaagaaatta caatcagagg tgagcactgc   1980

aacaaaaagg ctgttttctc tcggatctcc aaatttaaaa gcacaaggaa tgattgtacc   2040

acacaaagta atgtaaaaca ttagtaa                                       2067
```

<210> SEQ ID NO 2
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 2

```
atggtgagct actgggacac cggcgtgctg ctgtgcgccc tgctgagctg cctgctgctg     60

accggcagca gcagcggcag caagctgaag gaccccgagc tgagcctgaa gggcacccag    120

cacatcatgc aggccggcca gaccctgcac ctgcagtgcc gcggcgaggc cgcccacaag    180

tggagcctgc ccgagatggt gagcaaggag agcgagcgcc tgagcatcac caagagcgcc    240

tgcggccgca acggcaagca gttctgcagc accctgaccc tgaacaccgc ccaggccaac    300

cacaccggct tctacagctg caagtacctg gccgtgccca ccagcaagaa gaaggagacc    360

gagagcgcca tctacatctt catcagcgac accggccgcc ccttcgtgga gatgtacagc    420

gagatccccg agatcatcca catgaccgag ggccgcgagc tggtgatccc ctgccgcgtg    480

accagcccca acatcaccgt gaccctgaag aagttccccc tggacaccct gatccccgac    540

ggcaagcgca tcatctggga cagccgcaag ggcttcatca tcagcaacgc cacctacaag    600

gagatcggcc tgctgacctg cgaggccacc gtgaacggcc acctgtacaa gaccaactac    660

ctgacccacc gccagaccaa caccatcatc gacgtgcaga tcagcacccc ccgccccgtg    720

aagctgctgc gcggccacac cctggtgctg aactgcaccg ccaccacccc cctgaacacc    780

cgcgtgcaga tgacctggag ctaccccgac gagaagaaca agcgcgccag cgtgcgccgc    840

cgcatcgacc agagcaacag ccacgccaac atcttctaca gcgtgctgac catcgacaag    900

atgcagaaca aggacaaggg cctgtacacc tgccgcgtgc gcagcggccc cagcttcaag    960

agcgtgaaca ccagcgtgca catctacgac aaggccttca tcaccgtgaa gcaccgcaag   1020

cagcaggtgc tggagaccgt ggccggcaag cgcagctacc gcctgagcat gaaggtgaag   1080

gccttcccca gccccgaggt ggtgtggctg aaggacggcc tgcccgccac cgagaagagc   1140

gcccgctacc tgacccgcgg ctacagcctg atcatcaagg acgtgaccga ggaggacgcc   1200

ggcaactaca ccatcctgct gagcatcaag cagagcaacg tgttcaagaa cctgaccgcc   1260

accctgatcg tgaacgtgaa gccccagatc tacgagaagg ccgtgagcag cttccccgac   1320

cccgccctgt acccccctggg cagccgccag atcctgacct gcaccgccta cggcatcccc   1380

cagcccacca tcaagtggtt ctggcacccc tgcaaccaca accacagcga ggcccgctgc   1440

gacttctgca gcaacaacga ggagagcttc atcctggacg ccgacagcaa catgggcaac   1500
```

```
cgcatcgaga gcatcaccca gcgcatggcc atcatcgagg gcaagaacaa gatggccagc   1560

accctggtgg tggccgacag ccgcatcagc ggcatctaca tctgcatcgc cagcaacaag   1620

gtgggcaccg tgggccgcaa catcagcttc tacatcaccg acgtgcccaa cggcttccac   1680

gtgaacctgg agaagatgcc caccgagggc gaggacctga agctgagctg caccgtgaac   1740

aagttcctgt accgcgacgt gacctggatt ctgctgcgca ccgtgaacaa ccgcaccatg   1800

cactacagca tcagcaagca gaagatggcc atcaccaagg agcacagcat caccctgaac   1860

ctgaccatca tgaacgtgag cctgcaggac agcggcacct acgcctgccg cgcccgcaac   1920

gtgtacaccg gcgaggagat cctgcagaag aaggagatca ccatccgcgg cgagcactgc   1980

aacaagaagg ccgtgttcag ccgcatcagc aagttcaaga gcacccgcaa cgactgcacc   2040

acccagagca acgtgaagca ttagtaa                                      2067


<210> SEQ ID NO 3
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 3

atggtcagct actgggatac cggagtcctg ctctgcgccc tgctctcctg tctgctcctg     60

acaggctcca gcagcggcag caagctgaaa gaccctgaac tcagcctcaa gggcacacaa    120

cacatcatgc aggctggaca gaccctccat ctccagtgca gaggcgaggc cgctcacaag    180

tggtccctcc ctgagatggt gtccaaagaa agcgagaggc tgagcatcac caagagcgct    240

tgcggcagga atggcaaaca gttctgctcc acactcaccc tgaacacagc tcaagccaat    300

cacacaggct tctactcctg caaatatctc gccgtcccca caagcaagaa gaaagaaaca    360

gagtccgcca tttacatttt catctccgat accggcaggc ccttcgtcga aatgtacagc    420

gagatccccg agatcatcca tatgaccgaa ggcagagagc tcgtcattcc ctgcagggtc    480

accagcccca atattaccgt gaccctgaaa aagttccccc tcgatacact cattcccgac    540

ggcaagagga tcatctggga ttccagaaag ggcttcatta ttagcaatgc cacctataag    600

gagattggac tgctgacctg tgaggccacc gtgaacggcc acctctacaa gaccaactac    660

ctcacacaca ggcagaccaa caccatcatt gacgtccaga tcagcacccc caggcctgtg    720

aaactgctca gaggccatac actggtcctc aactgcacag ccacaacacc cctgaacaca    780

agggtgcaga tgacctggag ctaccctgac gagaaaaaca agagggccag cgtgagaagg    840

agaattgacc agtccaacag ccacgctaac atcttctatt ccgtcctgac aattgacaag    900

atgcagaaca aggataaggg cctctatacc tgcagagtca gatccggacc cagctttaaa    960

tccgtgaata ccagcgtcca catctacgac aaggccttca tcacagtgaa acacaggaag   1020

cagcaggtgc tcgagaccgt ggccggcaag aggtcctaca ggctgtccat gaaggtcaaa   1080

gctttccctt cccccgaggt cgtgtggctc aaagacggcc tccccgccac cgagaaaagc   1140

gctagatacc tcaccagagg ctacagcctg atcatcaagg acgtgacaga agaggatgct   1200

ggcaactaca ccattctcct gtccatcaag caatccaacg tcttcaagaa cctgaccgcc   1260

acactcatcg tgaatgtcaa gccccagatc tacgagaagg ccgtgagcag cttccccgat   1320

cctgccctgt atcccctcgg ctccagacaa attctcacct gcaccgccta cggaattccc   1380

cagcccacca tcaagtggtt ttggcacccc tgcaaccaca accattccga ggccagatgc   1440

gatttctgct ccaataacga ggagtccttc atcctcgatg ctgacagcaa catgggaaac   1500
```

```
aggatcgaat ccatcaccca gaggatggcc atcatcgagg gcaaaaataa aatggccagc   1560
accctggtcg tcgccgacag caggattagc ggcatctaca tttgcatcgc ctccaacaaa   1620
gtgggcaccg tgggaaggaa tatcagcttc tatatcaccg acgtgcccaa cggatttcac   1680
gtgaatctgg agaagatgcc taccgaggga gaagatctca agctcagctg caccgtcaac   1740
aagtttctgt acagggacgt cacatggatt ctgctcagga ccgtcaacaa caggaccatg   1800
cattactcca tttccaagca gaagatggcc atcaccaagg agcacagcat cacactcaac   1860
ctgaccatca tgaatgtgtc cctccaggac agcggaacat acgcctgcag ggccagaaac   1920
gtctacacag gcgaagagat cctgcagaaa aaggagatca ccatcagagg cgagcactgc   1980
aacaagaagg ccgtcttctc caggatcagc aagttcaaat ccaccaggaa cgactgcaca   2040
acccaatcca atgtcaagca ttagtaa                                       2067
```

<210> SEQ ID NO 4
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 4

```
atggtatcgt actgggatac gggcgtgttg ttgtgcgccc tgctgtcatg tttgcttttg     60
acagggtcct catcggggtc aaaactgaaa gaccctgagt tgagcctcaa gggaactcag    120
cacatcatgc aagctggtca gacgctccat ctgcagtgtc ggggagaagc tgcccacaag    180
tggagcctgc ccgagatggt gagcaaagag tcggagagac tttcgatcac gaaatccgca    240
tgcggaagaa atgggaaaca gttctgctcc accctgacat tgaataccgc gcaggccaac    300
cacactggat tctattcgtg taagtacttg gcggtgccca cgagcaaaaa gaaagagact    360
gagtcggcga tctacatctt tatctcagac acggggaggc cgttcgtgga aatgtattcg    420
gagattcccg agatcatcca catgacagaa gggcgagagc tcgtcatccc gtgtcgcgta    480
acttcaccca acatcaccgt gacactcaag aagtttccac tggacacact gattcccgac    540
ggaaagcgga tcatctggga ttcacgaaag ggtttatca tttccaacgc gacttacaaa      600
gagatcggac tgctgacgtg cgaggccacc gtcaacggac acctctataa gacgaattat    660
ctcacgcaca gacagaccaa caccatcatc gacgtacaga tctcaacccc acggccggta    720
aaactgctca gggggcacac gctcgtactg aattgcacag cgacgacgcc cctgaatacg    780
agggtccaga tgacctggtc gtacccggac gaaaagaata agcgggcgtc ggtgcggaga    840
aggatcgacc agtcgaattc acatgctaat atcttctact cggtactcac gatcgataag    900
atgcagaaca aagataaggg gttgtacact tgtagggtca ggagcgggcc ttcgttcaaa    960
agcgtaaaca ccagcgtcca catctacgac aaggccttta tcacggtcaa gcataggaag   1020
cagcaagtac tggaaactgt agcaggaaag agatcatata ggttgtccat gaaagtcaag   1080
gcgttcccat ccccggaggt cgtatggctt aaggacggac tccccgccac ggaaaagtcg   1140
gcacgctatt tgacgcgggg ttattcgctg atcattaagg atgtcacaga agaggatgcg   1200
gggaactata caattcttct ttccatcaag cagtccaatg tgttcaagaa tttgacagca   1260
accctcatcg taaacgtaaa gcctcaaatc tacgaaaagg cagtgagctc attccctgac   1320
ccagcgttgt accctctggg ctcgagacag atccttacgt gtactgcgta cgggattccc   1380
cagcctacca ttaagtggtt ttggcatccc tgcaaccaca accactcgga ggcgaggtgc   1440
```

gacttttgca gcaacaacga agaatcgttc atccttgatg cagactcaaa catgggtaat 1500
cggatcgaat cgatcaccca acgcatggct atcattgagg ggaagaataa gatggcatcg 1560
actttggtcg tggccgactc gcggatctca ggcatctaca tttgcatcgc aagcaacaaa 1620
gtgggaacgg tcggacggaa catttcgttc tatatcactg atgtacccaa tgggtttcac 1680
gtaaacctcg agaaaatgcc tacggaagga gaggatttga agctttcgtg caccgtgaac 1740
aagtttctct accgcgatgt gacgtggatc ttgcttagaa cggtgaacaa caggacaatg 1800
cactactcca tctcgaagca gaaaatggca atcactaaag aacatagcat tacgctcaac 1860
ttgactatta tgaatgtatc gcttcaagat tcggggacct atgcatgtag agctcgcaac 1920
gtctatacag gcgaagaaat tcttcaaaag aaggagatta ctatccgggg tgagcactgc 1980
aacaaaaagg cggtctttag ccgaatctca aagttcaaat cgactagaaa cgactgtaca 2040
acgcagtcaa acgtcaagca ttagtaa 2067

<210> SEQ ID NO 5
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 5
atggtgtcct actgggatac cggcgtgctg ctgtgtgccc tgctgagctg tctgctgctg 60
accggctcta gcagcggcag caagctgaag gaccctgagc tgagcctgaa gggcacccag 120
cacatcatgc aggccggcca gacactgcat ctgcagtgcc ggggagaagc cgcccacaaa 180
tggtccctgc ctgagatggt gtccaaagag agcgagcggc tgagcatcac caagagcgcc 240
tgcggcagaa acggcaagca gttctgcagc accctgaccc tgaataccgc ccaggccaac 300
cacaccggct tctacagctg caagtacctg gccgtgccca ccagcaagaa gaaagaaacc 360
gagagcgcca tctacatctt catcagcgac accggcagac ccttcgtgga aatgtacagc 420
gagatccccg agatcatcca catgaccgag ggccgcgagc tcgtgatccc ttgcagagtg 480
accagcccca acatcaccgt gacactgaag aagttccccc tggacaccct gatccccgac 540
ggcaagagaa tcatctggga cagccggaag ggcttcatca tcagcaacgc cacctacaaa 600
gagatcggcc tgctgacctg cgaggccacc gtgaatggcc acctgtacaa gaccaactac 660
ctgacccaca gacagaccaa caccatcatc gacgtgcaga tcagcacccc cagacccgtg 720
aagctgctga gaggccacac cctggtgctg aattgcaccg ccaccacccc cctgaacacc 780
agagtgcaga tgacctggtc ctaccccgac gagaagaaca agagggccag cgtgcggcgg 840
agaatcgacc agagcaacag ccacgccaac atcttctact ccgtgctgac catcgacaag 900
atgcagaaca aggacaaggg cctgtacacc tgtagagtgc ggagcggccc cagcttcaag 960
agcgtgaaca cctccgtgca catctacgac aaggccttca tcacagtgaa gcaccggaag 1020
cagcaggtgc tggaaaccgt ggccggcaag cggagctaca gactgagcat gaaagtgaaa 1080
gccttcccca gccccgaggt cgtgtggctg aaagatggac tgcccgccac cgagaagtcc 1140
gccagatacc tgaccagagg ctacagcctg atcatcaagg acgtgaccga agaggacgcc 1200
ggcaactaca ccatcctgct gtccatcaag cagagcaacg tgttcaagaa cctgaccgcc 1260
acactgatcg tgaacgtgaa gccccagatc tatgagaagg ccgtgtccag cttccccgac 1320
cccgctctgt atcctctggg cagcaggcag atcctgacct gcacagccta cggcatcccc 1380
cagcccacca tcaagtggtt ctggcacccc tgcaaccaca accacagcga ggccagatgc 1440

```
gacttctgct ccaacaacga ggaaagcttc atcctggacg ccgacagcaa catgggcaac   1500

cggatcgagt ccatcaccca gagaatggcc atcattgagg gcaagaacaa aatggcctct   1560

accctggtgg tggccgactc cagaatcagc ggcatctata tctgtatcgc cagcaacaaa   1620

gtgggcaccg tgggccggaa catcagcttc tacatcaccg atgtgcccaa cggcttccac   1680

gtgaacctgg aaaagatgcc caccgagggc gaggacctga agctgtcctg taccgtgaac   1740

aagtttctgt accgcgacgt gacctggatt ctgctgcgga cagtgaacaa ccggaccatg   1800

cactacagca tcagcaagca gaagatggct atcaccaaag agcacagcat caccctgaat   1860

ctgaccatca tgaacgtgtc actgcaggac agcggcacct acgcctgcag agccagaaac   1920

gtgtacaccg gcgaggaaat cctgcagaaa aaagagatca ccatccgggg cgagcactgc   1980

aacaagaaag ccgtgttcag ccggatcagc aagttcaaga gcacccggaa cgactgcacc   2040

acccagtcca atgtgaagca ctgatga                                       2067
```

```
<210> SEQ ID NO 6
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 6
```

```
atggtgagct attgggatac aggagttctc ctctgtgcac tgctttcctg tctgttgctt     60

actggatcaa gctcaggttc taagcttaag gacccegagt tgtccctgaa agggactcag    120

cacataatgc aagccggtca gactttgcat ctgcagtgca ggggggaggc cgctcataaa    180

tggagccttc ccgagatggt gtccaaggag tccgagagac tgtcaatcac taaatcagct    240

tgtggcagga acggcaagca gttctgtagc acactgactt tgaacaccgc acaggccaat    300

cacactggct tctactcatg taaatatctg gcggttccca catctaaaaa aaaggaaacc    360

gaatcagcca tctatatatt tatttcagac accggccgcc ctttcgttga aatgtactcc    420

gagattcctg aaattattca tatgacagaa gggagggagc tggtgatacc gtgtagggta    480

accagcccca acatcactgt gactctcaaa aaattccccc tggacacgct gatccccgat    540

ggaaagcgga ttatttggga ttcacggaaa gggtttatta tttccaacgc cacctacaag    600

gagatcggac tgctgacgtg tgaggcgact gtcaacggac acctgtacaa aaccaactat    660

ctgacacatc gccagaccaa taccatcata gatgtgcaaa tctcaacacc aaggcccgtg    720

aaactgctgc gcggtcacac tctggtgctc aattgcactg caacgacgcc tctgaatacg    780

cgagtgcaga tgacttggtc ctatcccgat gagaaaaaca agcgcgcctc agtaagaaga    840

aggattgacc aaagcaacag ccatgccaac atcttctatt cagtcctgac aatcgacaaa    900

atgcaaaaca aagataaggg cctttatact tgtcgcgtga ggagcggtcc atctttcaaa    960

agtgtaaata caagtgttca tatttatgat aaagctttca ttacagtgaa acaccgaaaa   1020

cagcaggtgc tggaaacagt ggctggcaag cgctcctacc gacttagcat gaaggtaaaa   1080

gcgttccctt ctcctgaagt cgtgtggctg aaggacggcc tgccagctac agaaaagagc   1140

gctcggtatt tgaccagagg ctacagcctg attatcaagg atgtgactga agaggacgcc   1200

ggcaattaca caattctgct ttccatcaag cagtcaaacg ttttcaaaaa tctgacagct   1260

acgttgatcg tgaacgtcaa acctcaaatc tacgagaaag ccgttagcag ctttccagac   1320

cctgctctct accccctcgg atctcggcaa atcctgacct gtactgcgta tggaatcccc   1380
```

-continued caaccaacca tcaagtggtt ttggcaccca tgtaatcaca atcattctga agcccgctgt 1440
gatttctgct caaacaatga ggagtccttc atcctggacg cagacagcaa tatgggcaat 1500
cggattgagt caatcacaca gaggatggca attatagagg gaaaaaacaa aatggcgagc 1560
accctggtcg tggctgactc cagaatcagt ggcatctaca tctgtatcgc ctcaaacaag 1620
gtcgggacag tcggtcgcaa tatcagcttc tatattacag acgtgcctaa cggttttcat 1680
gtgaacctcg agaagatgcc tacagaggga gaggatctga aactgtcatg cactgtaaac 1740
aaattcttgt accgcgacgt cacttggatc ttgctgagaa cagtcaataa caggaccatg 1800
cactactcaa ttagcaagca gaagatggct atcaccaaag agcactccat cacactgaac 1860
ctgactatca tgaatgtctc cttgcaggac tctggcactt atgcttgtcg ggcgaggaat 1920
gtgtatacag gcgaggaaat cctccagaag aaggagatta caattagggg agaacattgt 1980
aataagaaag cagtatttag tagaatcagt aaatttaagt ccaccaggaa cgactgtact 2040
actcagtcca acgtaaaaca ttagtaa 2067

<210> SEQ ID NO 7
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 7
atggtgtcct actgggacac cggagtgctg ctttgtgctc tgctttcttg cctgctgctt 60
actggcagct cctcaggaag taagttgaaa gaccccgagc ttagtctgaa gggaacacag 120
cacatcatgc aagccggaca gacactgcat ctccagtgcc gaggcgaggc agctcacaag 180
tggtccctgc ccgagatggt gtccaaagaa tctgagaggc tctcaatcac aaagagcgct 240
tgtgggagga acggcaagca gttctgttcc acactgactc tgaatactgc acaagctaat 300
cataccggat tttattcctg taaatatctg gccgtgccta ccagtaagaa aaaggaaacc 360
gagagtgcca tatatatctt cattagcgac acaggtcgcc ctttcgtgga gatgtactca 420
gaaatccccg agatcatcca catgactgaa ggccgagaac tcgtgatacc ttgtcgggtg 480
actagtccta atatcactgt cacactgaaa aagttccccc tcgatacact catccccgat 540
ggaaaacgca ttatctggga cagtcgcaaa ggatttatta tttccaacgc tacatataag 600
gaaatcgggt tgctcacctg cgaagctacc gtgaacgggc atctctataa gactaattat 660
ctgacccaca ggcagactaa cacaattata gacgtacaga ttagcacacc cagacctgtc 720
aagctgcttc gaggccatac tctggttctc aattgcaccg ctaccactcc cctgaatacc 780
cgggtccaaa tgacatggtc atatccggat gagaagaaca aacgagctag cgtgcgccga 840
cgcattgacc agtccaatag ccacgcgaac atttttttatt ctgttcttac catcgacaag 900
atgcagaata aagataaggg gttgtatacg tgtcgagtca gaagcgggcc tagcttcaag 960
agtgtcaaca catccgtcca catatacgat aaagccttta tcactgtgaa gcaccgcaaa 1020
caacaagtcc tggagacagt ggctggcaag cgatcctata ggctgagcat gaaggtaaag 1080
gccttcccca gcccggaggt ggtgtggctt aaggatggcc tgcctgcgac agagaaatca 1140
gcaagatatc tgaccagggg gtactctctt ataatcaaag acgtaacgga agaggatgcc 1200
ggtaactaca ccatactgct cagcatcaaa cagagtaacg tttttaagaa tttgaccgca 1260
accctgatag tcaatgtgaa acctcagatc tacgagaaag ccgtgtcttc attccccgac 1320
cccgccctgt accccctggg ttctcgccag atccttactt gcactgccta cggaattcct 1380

-continued

```
cagcctacga ttaagtggtt ttggcatcct tgtaaccata accatagcga ggcacggtgc   1440
gacttctgta gcaataacga ggagtctttc attctggatg cagactctaa tatgggtaac   1500
cgcattgagt ccatcacgca gaggatggcc attatcgaag ggaaaaataa gatggcctct   1560
actctggtgg tggctgatag ccgcatctca ggcatttata tctgcatagc ttctaataaa   1620
gttgggacag tggggaggaa tatctccttc tacattaccg atgtcccaaa cggattccat   1680
gtgaaccttg aaaaaatgcc gactgagggc gaggatctta agctgtcatg cactgtcaat   1740
aagtttctgt atcgagacgt gacttggata ctcctgcgga ctgtgaataa ccggactatg   1800
cattacagca tatctaagca gaaaatggcc atcactaagg aacactccat taccctgaac   1860
ctcaccataa tgaacgtcag cctccaagat tctggaacct acgcttgcag ggcccgaaat   1920
gtctacacag gggaggagat actccagaag aaggaaatca ccattcgggg ggaacactgc   1980
aataagaaag ctgtgttcag caggatttcc aagttcaaaa gcactcgaaa cgactgcacc   2040
actcagtcaa acgtgaaaca ctagtaa                                       2067
```

<210> SEQ ID NO 8
<211> LENGTH: 2067
<212> TYPE: DNA
<213> ORGANISM: Artificial Sequence
<220> FEATURE:
<223> OTHER INFORMATION: Synthetic Construct

<400> SEQUENCE: 8

```
atggtctcat actgggatac tggggtcctg ctgtgcgccc tgctgagttg tctgctgctg     60
actgggagtt ctagcgggtc caagctgaaa gacccagagc tgagcctgaa ggggactcag    120
cacattatgc aggctggaca gaccctgcac ctccagtgcc gaggagaggc agctcacaaa    180
tggtccctgc ccgaaatggt gtccaaggag tctgaaagac tgagtatcac caaatcagca    240
tgcggcagga acgggaagca gttctgttcc actctgaccc tgaacacagc acaggccaat    300
cataccggct tctactcttg caagtatctg gccgtgccca ccagtaagaa aaaggagaca    360
gaatcagcta tctatatttt catcagcgat accggacggc cctttgtgga gatgtacagt    420
gagatccctg aaatcattca catgactgag ggcagggagc tggtcatccc atgtcgcgtc    480
acctcaccca atatcacagt gactctgaaa aagttccctc tggacaccct gattccagat    540
ggaaaacgca tcatttggga ctcccgaaag ggctttatca tctctaacgc aacatacaag    600
gagatcgggc tgctgacctg cgaagccaca gtgaacggac atctgtacaa gactaattat    660
ctgacccaca gacagaccaa tacaatcatt gatgtgcaga tcagcacccc acggcctgtc    720
aagctgctga gaggacatac tctggtcctg aactgtaccg ccaccacacc tctgaatacc    780
agagtgcaga tgacatggtc ttacccagac gagaaaaaca agagggctag tgtccggaga    840
aggatcgacc agtctaacag tcacgcaaat attttctata gcgtgctgac aatcgacaag    900
atgcagaaca aagataaggg cctgtacact tgtcgcgtgc gaagtgggcc ttcattcaaa    960
agcgtgaata cttccgtcca tatctatgac aaagccttca tcaccgtgaa acaccggaag   1020
cagcaggtgc tggagacagt cgccgggaaa aggagctacc gcctgtccat gaaagtgaag   1080
gcttttccat cccccgaggt ggtctggctg aaagatggcc tgccagccac agaaaagagc   1140
gcccgatacc tgactcgggg gtattccctg atcattaagg acgtgaccga ggaagatgca   1200
ggaaactaca caatcctgct gagcatcaag cagagtaacg tgttcaagaa tctgactgcc   1260
accctgattg tgaatgtcaa accccagatc tacgagaagg ccgtgagcag cttccctgac   1320
```

-continued

```
ccagcactgt atcctctggg cagccggcag atcctgacat gcactgccta cggcatcccc   1380
cagcctacca ttaagtggtt ctggcatcct tgtaaccaca atcatagtga agcaaggtgc   1440
gatttctgtt ccaacaatga ggaatctttt atcctggacg ccgatagtaa catgggcaat   1500
cgaatcgagt caattaccca gcggatggct atcattgaag ggaaaaacaa gatggcatct   1560
acactggtgg tcgccgactc ccgcatctct ggcatctaca tctgcattgc ctcaaacaaa   1620
gtgggaacag tcggccggaa tatcagcttc tacattactg atgtgccaaa cggatttcac   1680
gtcaatctgg agaagatgcc caccgagggc gaagacctga aactgtcttg tacagtgaat   1740
aagttcctgt atagggatgt cacttggatt ctgctgagaa ctgtgaacaa taggaccatg   1800
cattactcaa tcagcaaaca gaagatggct atcaccaagg aacacagcat tacactgaac   1860
ctgactatca tgaacgtgag cctccaggac agcgggacct acgcttgccg ggcaagaaac   1920
gtgtatacag gagaggaaat cctccagaag aaggagatca caattcgcgg cgaacactgt   1980
aacaagaagg ccgtgtttag ccgaatctcc aagttcaagt caaccaggaa tgattgtact   2040
acccagtcaa atgtcaagca ctagtaa                                       2067
```

<210> SEQ ID NO 9
<211> LENGTH: 2012
<212> TYPE: DNA
<213> ORGANISM: Artificial Sequence
<220> FEATURE:
<223> OTHER INFORMATION: Synthetic Construct

<400> SEQUENCE: 9

```
atggtgtgct actgggatac cgggtgctgc tgtgcgccct gctgtgctgt ctgctgctga     60
cggctccagc tgcggtgcaa gctgaaagac cctgagctga gcctgaaggg caccagcaca    120
tcatgcaggc cggcagacct gcatctgcag tgccggggga ggccgctcac aagtggtccc    180
tgcccgagat ggtgtccaag gagtgcgaga ggctgagcat caccaagtgc gctgcggcag    240
gaacggcaag cagttctgct gcacctgacc ctgaacaccg ccaggccaat cacaccggct    300
tctactcctg caagtatctg gccgtgccca ccagcaagaa gaaggaaacc gagtcgccat    360
ctatatcttc atcagcgaca ccggccgccc ttcgtggaga tgtacagcga gatccccgag    420
atcatccaca tgacgaaggc cggagctcgt gatccctgtc gggtaccagc cccaacatca    480
ccgtgacctg aaaaagttcc ccctggacac ctgatccccg atggaaagcg catcatctgg    540
gactgccgaa agggctttat catttccaac gccacctaca aggagatcgg ctgctgacct    600
gcgaggccac cgtgaacggc acctgtacaa gaccaactat ctgacccaca gacagaccaa    660
caccatcatg acgtgcagat cagcaccccc cggccgtgaa gctgctgaga ggccatactc    720
tggtctgaat tgcaccgcca ccacccccctg aataccagag tgcagatgac ctggtcctac    780
ccgacgagaa gaacaagcgg gccagcgtgc ggcgaagatt gaccagtgca acagccacgc    840
caacatcttc tattccgtct gacatcgaca agatgcagaa caaagataag ggcctgtata    900
cttgtcggtg aggagcggcc tgcttcaaaa gcgtgaacac ctgcgtccac atctacgaca    960
aggccttcat cacgtgaagc accggaagca gcaggtgctg gagaccgtgg ccggcaagcg   1020
gtcctaccgg ctgtgcatga aggtgaaggc ttcccctccc ccgaggtcgt gtggctgaag   1080
gatggcctgc ccgccacgag aagtgcgccg atatctgacc cgggctactg cctgatcatc   1140
aaggacgtga cgaagaggat gccggcaact acaccatcct gctgtgcatc aagcagtgca   1200
acgtgttcaa gaatctgacc gccaccctga tcgtgaatgt gaagccccag atctacgaga   1260
aggccgtgag cagcttcccc gacccgcctg taccccctgg gctgccgcag atcctgacct   1320
```

-continued gcactgccta cggatccccc agcctaccat caagtggttt tggcacccct gtaaccacaa 1380
ccattgcgag gccaggtgcg acttctgctc caacaacgag gagtccttca tcctggatgc 1440
gacagcaaca tgggcaaccg gatcgagtcc atcacccagc ggatggccat catgagggaa 1500
gaataagatg gcctgcaccc tggtggtggc cgactcccga tctgggcatc tacatctgca 1560
tcgcctccaa caaagtggga cgtgggcgga atatcagctt ctatatcacc gatgtgccca 1620
acggtttcac gtgaacctgg agaagatgcc accgagggcg aggatctgaa gctgtctgca 1680
ccgtgaacaa gtttctgtac cgcgacgtga cttggattct gctgcggacg tgaacaacag 1740
gaccatgcac tactgcatca gcaagcagaa gatggccatc accaaggagc acagcatcac 1800
ctgaacctga ccatcatgaa tgtgtccctg caggactgcg gcacctacgc ctgcagggcc 1860
agaaacgtgt acacaggcga ggaaatcctc cagaagaagg agatcaccat ccggggcgag 1920
cactgcaaca agaaggccgt gttcagccgg atctgcaagt tcaagtgcac caggaacgac 1980
tgtaccaccc agtccaatgt aagcattagt aa 2012

<210> SEQ ID NO 10
<211> LENGTH: 2211
<212> TYPE: DNA
<213> ORGANISM: Artificial Sequence
<220> FEATURE:
<223> OTHER INFORMATION: Synthetic Construct

<400> SEQUENCE: 10
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttaaagaaga tacgtctttt gggggcaacc tcggacgagc agtcttccag 360
gcgaaaaaga gggttcttga acctctgggc ctggttgagg aacctgttaa gacggctccg 420
ggaaaaaaga ggccggtaga gcactctcct gtggagccag actcctcctc gggaaccgga 480
aaggcgggcc agcagcctgc aagaaaaaga ttgaattttg gtcagactgg agacgcagac 540
tcagtacctg acccccagcc tctcggacag ccaccagcag ccccctctgg tctgggaact 600
aatacgatgg ctacaggcag tggcgcacca atggcagaca ataacgaggg cgccgacgga 660
gtgggtaatt cctcgggaaa ttggcattgc gattccacat ggatgggcga cagagtcatc 720
accaccagca cccgaacctg ggccctgccc acctacaaca accacctcta caaacaaatt 780
tccagcgctt caacgggagc ctcgaacgac aatcactact ttggctacag caccccttgg 840
gggtattttg acttcaacag attccactgc cacttttcac cacgtgactg gcaaagactc 900
atcaacaaca actggggatt ccgacccaag agactcaact tcaagctctt taacattcaa 960
gtcaaagagg tcacgcagaa tgacggtacg acgacgattg ccaataacct taccagcacg 1020
gttcaggtgt ttactgactc ggagtaccag ctcccgtacg tcctcggctc ggcgcatcaa 1080
ggatgcctcc cgccgttccc agcagacgtc ttcatggtgc cacagtatgg atacctcacc 1140
ctgaacaacg ggagtcaggc agtaggacgc tcttcatttt actgcctgga gtactttcct 1200
tctcagatgc tgcgtaccgg aaacaacttt accttcagct acacttttga ggacgttcct 1260
ttccacagca gctacgctca cagccagagt ctggaccgtc tcatgaatcc tctcatcgac 1320
cagtacctgt attacttgag cagaacaaac actccaagtg gaaccaccac gcagtcaagg 1380
cttcagtttt ctcaggccgg agcgagtgac attcgggacc agtctaggaa ctggcttcct 1440
ggaccctgtt accgccagca gcgagtatca aagacatctg cggataacaa caacagtgaa 1500
tactcgtgga ctggagctac caagtaccac ctcaatggca gagactctct ggtgaatccg 1560
ggcccggcca tggcaagcca caaggacgat gaagaaaagt tttttcctca gagcggggtt 1620
ctcatctttg ggaagcaagg ctcagagaaa acaaatgtgg acattgaaaa ggtcatgatt 1680
acagacgaag aggaaatcag gacaaccaat cccgtggcta cggagcagta tggttctgta 1740
tctaccaacc tccagagagg caacagacaa gcagctaccg cagatgtcaa cacacaaggc 1800
gttcttccag gcatggtctg gcaggacaga gatgtgtacc ttcaggggcc catctgggca 1860
aagattccac acacggacgg acattttcac ccctctcccc tcatgggtgg attcggactt 1920
aaacaccctc ctccacagat tctcatcaag aacaccccgg tacctgcgaa tccttcgacc 1980
accttcagtg cggcaaagtt tgcttccttc atcacacagt actccacggg acaggtcagc 2040
gtggagatcg agtgggagct gcagaaggaa aacagcaaac gctggaatcc cgaaattcag 2100
tacacttcca actacgccaa gtctgtcaat gtggacttta ctgtggacaa taatggcgtg 2160
tattcagagc ctcgccccat tggcaccaga tacctgactc gtaatctgta a 2211

<210> SEQ ID NO 11
<211> LENGTH: 2211
<212> TYPE: DNA
<213> ORGANISM: Artificial Sequence
<220> FEATURE:
<223> OTHER INFORMATION: Synthetic Construct

<400> SEQUENCE: 11
atggctgccg atggttatct tccagattgg ctcgaggaca acctctctga gggcattcgc 60
gagtggtggg acttgaaacc tggagccccg aagcccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaac gtccggtaga gcagtcgcca caagagccag actcctcctc gggcatcggc 480
aagacaggcc agcagcccgc taaaaagaga ctcaattttg gtcagactgg cgactcagag 540
tcagtccccg atccacaacc tctcggagaa cctccagcaa cccccgctgc tgtgggacct 600
actacaatgg cttcaggcgg tggcgcacca atggcagaca ataacgaagg cgccgacgga 660
gtgggtaatg cctcaggaaa ttggcattgc gattccacat ggctgggcga cagagtcatc 720
accaccagca cccgcacctg ggccttgccc acctacaata accacctcta caagcaaatc 780
tccagtgctt caacgggggc cagcaacgac aaccactact tcggctacag cacccccctgg 840 gggtattttg atttcaacag attccactgc cacttttcac cacgtgactg gcagcgactc 900
atcaacaaca attggggatt ccggcccaag agactcaact tcaaactctt caacatccaa 960
gtcaaggagg tcacgacgaa tgatggcgtc acaaccatcg ctaataacct taccagcacg 1020
gttcaagtct tctcggactc ggagtaccag cttccgtacg tcctcggctc tgcgcaccag 1080
ggctgcctcc ctccgttccc ggcggacgtg ttcatgattc cgcaatacgg ctacctgacg 1140
ctcaacaatg gcagccaagc cgtgggacgt tcatcctttt actgcctgga atatttccct 1200

```
tctcagatgc tgagaacggg caacaacttt accttcagct acacctttga ggaagtgcct   1260
ttccacagca gctacgcgca cagccagagc ctggaccggc tgatgaatcc tctcatcgac   1320
caatacctgt attacctgaa cagaactcaa aatcagtccg gaagtgccca aaacaaggac   1380
ttgctgttta gccgtgggtc tccagctggc atgtctgttc agcccaaaaa ctggctacct   1440
ggaccctgtt atcggcagca gcgcgtttct aaaacaaaaa cagacaacaa caacagcaat   1500
tttacctgga ctggtgcttc aaaatataac ctcaatgggc gtgaatccat catcaaccct   1560
ggcactgcta tggcctcaca caaagacgac gaagacaagt tctttcccat gagcggtgtc   1620
atgatttttg gaaaagagag cgccggagct tcaaacactg cattggacaa tgtcatgatt   1680
acagacgaag aggaaattaa agccactaac cctgtggcca ccgaaagatt tgggaccgtg   1740
gcagtcaatt tccagagcag cagcacagac cctgcgaccg gagatgtgca tgctatggga   1800
gcattacctg gcatggtgtg gcaagataga gacgtgtacc tgcagggtcc catttgggcc   1860
aaaattcctc acacagatgg acactttcac ccgtctcctc ttatgggcgg ctttggactc   1920
aagaacccgc ctcctcagat cctcatcaaa aacacgcctg ttcctgcgaa tcctccggcg   1980
gagttttcag ctacaaagtt tgcttcattc atcacccaat actccacagg acaagtgagt   2040
gtggaaattg aatgggagct gcagaaagaa aacagcaagc gctggaatcc cgaagtgcag   2100
tacacatcca attatgcaaa atctgccaac gttgatttta ctgtggacaa caatggactt   2160
tatactgagc ctcgccccat tggcacccgt taccttaccc gtcccctgta a            2211
```

```
<210> SEQ ID NO 12
<211> LENGTH: 2208
<212> TYPE: DNA
<213> ORGANISM: Artificial Sequence
<220> FEATURE:
<223> OTHER INFORMATION: Synthetic Construct

<400> SEQUENCE: 12
```

```
atggctgccg atggttatct tccagattgg ctcgaggaca acctctctga gggcattcgc     60
gagtggtggg acttgaaacc tggagccccg aagcccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaac gtccggtaga gcagtcgcca caagagccag actcctcctc gggcatcggc    480
aagacaggcc agcagcccgc taaaaagaga ctcaattttg gtcagactgg cgactcagag    540
tcagtccccg atccacaacc tctcggagaa cctccagcaa cccccgctgc tgtgggacct    600
actacaatgg cttcaggcgg tggcgcacca atggcagaca ataacgaagg cgccgacgga    660
gtgggtaatg cctcaggaaa ttggcattgc gattccacat ggctgggcga cagagtcatc    720
accaccagca cccgcacctg ggccttgccc acctacaata accacctcta caagcaaatc    780
tccagtgctt caggggccag caacgacaac cactacttcg gctacagcac cccctggggg    840
tattttgatt tcaacagatt ccactgccac ttttcaccac gtgactggca gcgactcatc    900
aacaacaatt ggggattccg gcccaagaga ctcaacttca aactcttcaa catccaagtc    960
aaggaggtca cgacgaatga tggcgtcaca accatcgcta ataaccttac cagcacggtt   1020
```

-continued

```
caagtcttct cggactcgga gtaccagctt ccgtacgtcc tcggctctgc gcaccagggc   1080

tgcctccctc cgttcccggc ggacgtgttc atgattccgc aatacggcta cctgacgctc   1140

aacaatggca gccaagccgt gggacgttca tccttttact gcctggaata tttcccttct   1200

cagatgctga gaacgggcaa caactttacc ttcagctaca cctttgagga agtgcctttc   1260

cacagcagct acgcgcacag ccagagcctg gaccggctga tgaatcctct catcgaccaa   1320

tacctgtatt acctgaacag aactcaaaat cagtccggaa gtgcccaaaa caaggacttg   1380

ctgtttagcc gtgggtctcc agctggcatg tctgttcagc ccaaaaactg gctacctgga   1440

ccctgttatc ggcagcagcg cgtttctaaa acaaaaacag acaacaacaa cagcaatttt   1500

acctggactg gtgcttcaaa atataacctc aatgggcgtg aatccatcat caaccctggc   1560

actgctatgg cctcacacaa agacgacgaa gacaagttct ttcccatgag cggtgtcatg   1620

atttttggaa aagagagcgc cggagcttca aacactgcat tggacaatgt catgattaca   1680

gacgaagagg aaattaaagc cactaaccct gtggccaccg aaagatttgg gaccgtggca   1740

gtcaatttcc agagcagcag cacagaccct gcgaccggag atgtgcatgc tatgggagca   1800

ttacctggca tggtgtggca agatagagac gtgtacctgc agggtcccat ttgggccaaa   1860

attcctcaca cagatggaca ctttcacccg tctcctctta tgggcggctt tggactcaag   1920

aacccgcctc ctcagatcct catcaaaaac acgcctgttc ctgcgaatcc tccggcggag   1980

ttttcagcta caaagtttgc ttcattcatc acccaatact ccacaggaca agtgagtgtg   2040

gaaattgaat gggagctgca gaaagaaaac agcaagcgct ggaatcccga agtgcagtac   2100

acatccaatt atgcaaaatc tgccaacgtt gattttactg tggacaacaa tggactttat   2160

actgagcctc gccccattgg cacccgttac cttacccgtc ccctgtaa                2208
```

<210> SEQ ID NO 13
<211> LENGTH: 2211
<212> TYPE: DNA
<213> ORGANISM: Artificial Sequence
<220> FEATURE:
<223> OTHER INFORMATION: Synthetic Construct

<400> SEQUENCE: 13

```
atggctgccg atggttatct tccagattgg ctcgaggaca acctctctga gggcattcgc     60

gagtggtggg acttgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggatgca gcggccctcg agcacgacaa ggcctacgac    240

cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaaga gggttctcga accttttggt ctggttgagg aaggtgctaa gacggctcct    420

ggaaagaaac gtccggtaga gcagtcgcca caagagccag actcctcctc gggcattggc    480

aagacaggcc agcagcccgc taaaaagaga ctcaattttg gtcagactgg cgactcagag    540

tcagtccccg acccacaacc tctcggagaa cctccagcaa cccccgctgc tgtgggacct    600

actacaatgg cttcaggcgg tggcgcacca atggcagaca ataacgaagg cgccgacgga    660

gtgggtaatg cctcaggaaa ttggcattgc gattccacat ggctgggcga cagagtcatc    720

accaccagca cccgaacatg ggccttgccc acctataaca accacctcta caagcaaatc    780

tccagtgctt caacgggggc cagcaacgac aaccactact tcggctacag caccccctgg    840

gggtattttg atttcaacag attccactgc catttctcac cacgtgactg gcagcgactc    900
```

-continued

```
atcaacaaca attggggatt ccggcccaag agactcaact tcaagctctt caacatccaa    960
gtcaaggagg tcacgacgaa tgatggcgtc acgaccatcg ctaataacct taccagcacg   1020
gttcaagtct tctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atatttccca   1200
tcgcagatgc tgagaacggg caataacttt accttcagct acaccttcga ggacgtgcct   1260
ttccacagca gctacgcgca cagccagagc ctggaccggc tgatgaatcc tctcatcgac   1320
cagtacctgt attacctgaa cagaactcag aatcagtccg gaagtgccca aaacaaggac   1380
ttgctgttta gccgggggtc tccagctggc atgtctgttc agcccaaaaa ctggctacct   1440
ggaccctgtt accggcagca gcgcgtttct aaaacaaaaa cagacaacaa caacagcaac   1500
tttacctgga ctggtgcttc aaaatataac cttaatgggc gtgaatctat aatcaaccct   1560
ggcactgcta tggcctcaca caaagacgac aaagacaagt tctttcccat gagcggtgtc   1620
atgatttttg gaaaggagag cgccggagct tcaaacactg cattggacaa tgtcatgatc   1680
acagacgaag aggaaatcaa agccactaac cccgtggcca ccgaaagatt tgggactgtg   1740
gcagtcaatc tccagagcag cagcacagac cctgcgaccg gagatgtgca tgttatggga   1800
gccttacctg gaatggtgtg gcaagacaga gacgtatacc tgcagggtcc tatttgggcc   1860
aaaattcctc acacggatgg acactttcac ccgtctcctc tcatgggcgg ctttggactt   1920
aagcacccgc ctcctcagat cctcatcaaa aacacgcctg ttcctgcgaa tcctccggca   1980
gagttttcgg ctacaaagtt tgcttcattc atcacccagt attccacagg acaagtgagc   2040
gtggagattg aatgggagct gcagaaagaa aacagcaaac gctggaatcc cgaagtgcag   2100
tatacatcta actatgcaaa atctgccaac gttgatttca ctgtggacaa caatggactt   2160
tatactgagc ctcgccccat tggcacccgt tacctcaccc gtcccctgta a            2211
```

<210> SEQ ID NO 14
<211> LENGTH: 2208
<212> TYPE: DNA
<213> ORGANISM: Artificial Sequence
<220> FEATURE:
<223> OTHER INFORMATION: Synthetic Construct

<400> SEQUENCE: 14

```
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg gacccttcaa cggactcgac    180
aagggggagc ccgtcaacgc ggcggatgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaaga gggttctcga acctttttggt ctggttgagg aaggtgctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag    540
tcagtccccg acccacaacc tctcggagaa cctccagcaa cccccgctgc tgtgggacct    600
actacaatgg cttcaggcgg tggcgcacca atggcagaca ataacgaagg cgccgacgga    660
gtgggtaatg cctcaggaaa ttggcattgc gattccacat ggctgggcga cagagtcatc    720
```

-continued

```
accaccagca cccgaacatg ggccttgccc acctataaca accacctcta caagcaaatc    780
tccagtgctt caggggccag caacgacaac cactacttcg gctacagcac cccctggggg    840
tattttgatt tcaacagatt ccactgccat ttctcaccac gtgactggca gcgactcatc    900
aacaacaatt ggggattccg gcccaagaga ctcaacttca agctcttcaa catccaagtc    960
aaggaggtca cgacgaatga tggcgtcacg accatcgcta ataaccttac cagcacggtt   1020
caagtcttct cggactcgga gtaccagttg ccgtacgtcc tcggctctgc gcaccagggc   1080
tgcctccctc cgttcccggc ggacgtgttc atgattccgc agtacggcta cctaacgctc   1140
aacaatggca gccaggcagt gggacggtca tccttttact gcctggaata tttcccatcg   1200
cagatgctga gaacgggcaa taactttacc ttcagctaca ccttcgagga cgtgcctttc   1260
cacagcagct acgcgcacag ccagagcctg gaccggctga tgaatcctct catcgaccag   1320
tacctgtatt acctgaacag aactcagaat cagtccggaa gtgcccaaaa caaggacttg   1380
ctgtttagcc gggggtctcc agctggcatg tctgttcagc ccaaaaactg gctacctgga   1440
ccctgttacc ggcagcagcg cgtttctaaa acaaaaacag acaacaacaa cagcaacttt   1500
acctggactg gtgcttcaaa atataacctt aatgggcgtg aatctataat caaccctggc   1560
actgctatgg cctcacacaa agacgacaaa gacaagttct ttcccatgag cggtgtcatg   1620
atttttggaa aggagagcgc cggagcttca aacactgcat tggacaatgt catgatcaca   1680
gacgaagagg aaatcaaagc cactaacccc gtggccaccg aaagatttgg gactgtggca   1740
gtcaatctcc agagcagcag cacagaccct gcgaccggag atgtgcatgt tatgggagcc   1800
ttacctggaa tggtgtggca agacagagac gtatacctgc agggtcctat ttgggccaaa   1860
attcctcaca cggatggaca ctttcacccg tctcctctca tgggcggctt tggacttaag   1920
cacccgcctc ctcagatcct catcaaaaac acgcctgttc ctgcgaatcc tccggcagag   1980
ttttcggcta caaagtttgc ttcattcatc acccagtatt ccacaggaca agtgagcgtg   2040
gagattgaat gggagctgca gaaagaaaac agcaaacgct ggaatcccga agtgcagtat   2100
acatctaact atgcaaaatc tgccaacgtt gatttcactg tggacaacaa tggactttat   2160
actgagcctc gccccattgg cacccgttac ctcacccgtc ccctgtaa                2208
```

<210> SEQ ID NO 15
<211> LENGTH: 2208
<212> TYPE: DNA
<213> ORGANISM: Artificial Sequence
<220> FEATURE:
<223> OTHER INFORMATION: Syntheitc Constuct

<400> SEQUENCE: 15

```
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg gacccttcaa cggactcgac    180
aagggggagc ccgtcaacgc ggcggatgca gcggccctcg agcacgacaa ggcctacgac    240
cagcagctca aagcgggtga caatccgtac ctgcggtata accacgccga cgccgagttt    300
caggagcgtc tgcaagaaga tacgtctttt gggggcaacc tcgggcgagc agtcttccag    360
gccaagaaga gggttctcga accttttggt ctggttgagg aaggtgctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag    540
tcagtccccg acccacaacc tctcggagaa cctccagcaa cccccgctgc tgtgggacct    600
```

-continued

```
actacaatgg cttcaggcgg tggcgcacca atggcagaca ataacgaagg cgccgacgga     660

gtgggtaatg cctcaggaaa ttggcattgc gattccacat ggctgggcga cagagtcatc     720

accaccagca cccgaacatg ggccttgccc acctataaca accacctcta caagcaaatc     780

tccagtgctt caggggccag caacgacaac cactacttcg gctacagcac cccctggggg     840

tattttgatt tcaacagatt ccactgccat ttctcaccac gtgactggca gcgactcatc     900

aacaacaatt ggggattccg gcccaagaga ctcaacttca agctcttcaa catccaagtc     960

aaggaggtca cgacgaatga tggcgtcacg accatcgcta ataaccttac cagcacggtt    1020

caagtcttct cggactcgga gtaccagttg ccgtacgtcc tcggctctgc gcaccagggc    1080

tgcctccctc cgttcccggc ggacgtgttc atgattccgc agtacggcta cctaacgctc    1140

aacaatggca gccaggcagt gggacggtca tccttttact gcctggaata tttcccatcg    1200

cagatgctga gaacgggcaa taactttacc ttcagctaca ccttcgagga cgtgcctttc    1260

cacagcagct acgcgcacag ccagagcctg gaccggctga tgaatcctct catcgaccag    1320

tacctgtatt acctgaacag aactcagaat cagtccggaa gtgcccaaaa caaggacttg    1380

ctgtttagcc gggggtctcc agctggcatg tctgttcagc ccaaaaactg gctacctgga    1440

ccctgttacc ggcagcagcg cgtttctaaa acaaaaacag acaacaacaa cagcaacttt    1500

acctggactg gtgcttcaaa atataacctt aatgggcgtg aatctataat caaccctggc    1560

actgctatgg cctcacacaa agacgacgaa gacaagttct ttcccatgag cggtgtcatg    1620

atttttggaa aggagagcgc cggagcttca aacactgcat tggacaatgt catgatcaca    1680

gacgaagagg aaatcaaagc cactaacccc gtggccaccg aaagatttgg gactgtggca    1740

gtcaatctcc agagcagcag cacagaccct gcgaccggag atgtgcatgt tatgggagcc    1800

ttacctggaa tggtgtggca agacagagac gtatacctgc agggtcctat ttgggccaaa    1860

attcctcaca cggatggaca ctttcacccg tctcctctca tgggcggctt tggacttaag    1920

cacccgcctc ctcagatcct catcaaaaac acgcctgttc ctgcgaatcc tccggcagag    1980

ttttcggcta caaagtttgc ttcattcatc acccagtatt ccacaggaca agtgagcgtg    2040

gagattgaat gggagctgca gaaagaaaac agcaaacgct ggaatcccga agtgcagtat    2100

acatctaact atgcaaaatc tgccaacgtt gatttcactg tggacaacaa tggactttat    2160

actgagcctc gccccattgg cacccgttac ctcacccgtc ccctgtaa                 2208
```

<210> SEQ ID NO 16
<211> LENGTH: 897
<212> TYPE: DNA
<213> ORGANISM: Artificial Sequence
<220> FEATURE:
<223> OTHER INFORMATION: Synthetic Construct

<400> SEQUENCE: 16

```
ctgggccttg cccacctaca ataaccacct ctacaagcaa atctccagtg cttcaacggg      60

ggccagcaac gacaaccact acttcggcta cagcaccccc tgggggtatt ttgatttcaa     120

cagattccac tgccactttt caccacgtga ctggcagcga ctcatcaaca acaattgggg     180

attccggccc aagagactca acttcaaact cttcaacatc caagtcaagg aggtcacgac     240

gaatgatggc gtcacaacca tcgctaataa ccttaccagc acggttcaag tcttctcgga     300

ctcggagtac cagcttccgt acgtcctcgg ctctgcgcac cagggctgcc tccctccgtt     360

cccggcggac gtgttcatga ttccgcaata cggctacctg acgctcaaca atggcagcca     420
```

-continued agccgtggga cgttcatcct tttactgcct ggaatatttc ccttctcaga tgctgagaac 480
gggcaacaac tttaccttca gctacacctt tgaggaagtg cctttccaca gcagctacgc 540
gcacagccag agcctggacc ggctgatgaa tcctctcatc gaccaatacc tgtattacct 600
gaacagaact caaaatcagt ccggaagtgc ccaaaacaag gacttgctgt ttagccgtgg 660
gtctccagct ggcatgtctg ttcagcccaa aaactggcta cctggaccct gttatcggca 720
gcagcgcgtt tctaaaacaa aaacagacaa caacaacagc aattttacct ggactggtgc 780
ttcaaaatat aacctcaatg ggcgtgaatc catcatcaac cctggcactg ctatggcctc 840
acacaaagac gacgaagaca agttctttcc catgagcggt gtcatgattt ttggaaa 897

<210> SEQ ID NO 17
<211> LENGTH: 894
<212> TYPE: DNA
<213> ORGANISM: Artificial Sequence
<220> FEATURE:
<223> OTHER INFORMATION: Synthetic Construct

<400> SEQUENCE: 17
ctgggccttg cccacctaca ataaccacct ctacaagcaa atctccagtg cttcaggggc 60
cagcaacgac aaccactact tcggctacag cacccccctgg gggtattttg atttcaacag 120
attccactgc cacttttcac cacgtgactg gcagcgactc atcaacaaca attggggatt 180
ccggcccaag agactcaact tcaaactctt caacatccaa gtcaaggagg tcacgacgaa 240
tgatggcgtc acaaccatcg ctaataacct taccagcacg gttcaagtct tctcggactc 300
ggagtaccag cttccgtacg tcctcggctc tgcgcaccag ggctgcctcc ctccgttccc 360
ggcggacgtg ttcatgattc cgcaatacgg ctacctgacg ctcaacaatg gcagccaagc 420
cgtgggacgt tcatcctttt actgcctgga atatttccct tctcagatgc tgagaacggg 480
caacaacttt accttcagct acacctttga ggaagtgcct ttccacagca gctacgcgca 540
cagccagagc ctggaccggc tgatgaatcc tctcatcgac caatacctgt attacctgaa 600
cagaactcaa aatcagtccg gaagtgccca aaacaaggac ttgctgttta gccgtgggtc 660
tccagctggc atgtctgttc agcccaaaaa ctggctacct ggaccctgtt atcggcagca 720
gcgcgtttct aaaacaaaaa cagacaacaa caacagcaat tttacctgga ctggtgcttc 780
aaaatataac ctcaatgggc gtgaatccat catcaaccct ggcactgcta tggcctcaca 840
caaagacgac gaagacaagt tctttcccat gagcggtgtc atgatttttg gaaa 894

<210> SEQ ID NO 18
<211> LENGTH: 897
<212> TYPE: DNA
<213> ORGANISM: Artificial Sequence
<220> FEATURE:
<223> OTHER INFORMATION: Synthetic construct

<400> SEQUENCE: 18
atgggccttg cccacctata acaaccacct ctacaagcaa atctccagtg cttcaacggg 60
ggccagcaac gacaaccact acttcggcta cagcaccccc tgggggtatt ttgatttcaa 120
cagattccac tgccatttct caccacgtga ctggcagcga ctcatcaaca acaattgggg 180
attccggccc aagagactca acttcaagct cttcaacatc caagtcaagg aggtcacgac 240
gaatgatggc gtcacgacca tcgctaataa ccttaccagc acggttcaag tcttctcgga 300
ctcggagtac cagttgccgt acgtcctcgg ctctgcgcac cagggctgcc tccctccgtt 360
cccggcggac gtgttcatga ttccgcagta cggctaccta acgctcaaca atggcagcca 420

```
ggcagtggga cggtcatcct tttactgcct ggaatatttc ccatcgcaga tgctgagaac    480

gggcaataac tttaccttca gctacacctt cgaggacgtg cctttccaca gcagctacgc    540

gcacagccag agcctggacc ggctgatgaa tcctctcatc gaccagtacc tgtattacct    600

gaacagaact cagaatcagt ccggaagtgc ccaaaacaag gacttgctgt ttagccgggg    660

gtctccagct ggcatgtctg ttcagcccaa aaactggcta cctggaccct gttaccggca    720

gcagcgcgtt tctaaaacaa aaacagacaa caacaacagc aactttacct ggactggtgc    780

ttcaaaatat aaccttaatg ggcgtgaatc tataatcaac cctggcactg ctatggcctc    840

acacaaagac gacaaagaca agttctttcc catgagcggt gtcatgattt ttggaaa       897
```

```
<210> SEQ ID NO 19
<211> LENGTH: 894
<212> TYPE: DNA
<213> ORGANISM: Artificial Sequence
<220> FEATURE:
<223> OTHER INFORMATION: Synthetic Construct

<400> SEQUENCE: 19

atgggccttg cccacctata acaaccacct ctacaagcaa atctccagtg cttcaggggc     60

cagcaacgac aaccactact tcggctacag cacccccctgg gggtattttg atttcaacag   120

attccactgc catttctcac cacgtgactg gcagcgactc atcaacaaca attggggatt    180

ccggcccaag agactcaact tcaagctctt caacatccaa gtcaaggagg tcacgacgaa    240

tgatggcgtc acgaccatcg ctaataacct taccagcacg gttcaagtct tctcggactc    300

ggagtaccag ttgccgtacg tcctcggctc tgcgcaccag ggctgcctcc ctccgttccc    360

ggcggacgtg ttcatgattc cgcagtacgg ctacctaacg ctcaacaatg gcagccaggc    420

agtgggacgg tcatcctttt actgcctgga atatttccca tcgcagatgc tgagaacggg    480

caataacttt accttcagct acaccttcga ggacgtgcct ttccacagca gctacgcgca    540

cagccagagc ctggaccggc tgatgaatcc tctcatcgac cagtacctgt attacctgaa    600

cagaactcag aatcagtccg gaagtgccca aaacaaggac ttgctgttta gccgggggtc    660

tccagctggc atgtctgttc agcccaaaaa ctggctacct ggaccctgtt accggcagca    720

gcgcgtttct aaaacaaaaa cagacaacaa caacagcaac tttacctgga ctggtgcttc    780

aaaatataac cttaatgggc gtgaatctat aatcaaccct ggcactgcta tggcctcaca    840

caaagacgac aaagacaagt tctttcccat gagcggtgtc atgatttttg gaaa          894
```

```
<210> SEQ ID NO 20
<211> LENGTH: 894
<212> TYPE: DNA
<213> ORGANISM: Artificial Sequence
<220> FEATURE:
<223> OTHER INFORMATION: Synthetic Construct

<400> SEQUENCE: 20

atgggccttg cccacctata acaaccacct ctacaagcaa atctccagtg cttcaggggc     60

cagcaacgac aaccactact tcggctacag cacccccctgg gggtattttg atttcaacag   120

attccactgc catttctcac cacgtgactg gcagcgactc atcaacaaca attggggatt    180

ccggcccaag agactcaact tcaagctctt caacatccaa gtcaaggagg tcacgacgaa    240

tgatggcgtc acgaccatcg ctaataacct taccagcacg gttcaagtct tctcggactc    300

ggagtaccag ttgccgtacg tcctcggctc tgcgcaccag ggctgcctcc ctccgttccc    360
```

```
ggcggacgtg ttcatgattc cgcagtacgg ctacctaacg ctcaacaatg gcagccaggc    420

agtgggacgg tcatcctttt actgcctgga atatttccca tcgcagatgc tgagaacggg    480

caataacttt accttcagct acaccttcga ggacgtgcct ttccacagca gctacgcgca    540

cagccagagc ctggaccggc tgatgaatcc tctcatcgac cagtacctgt attacctgaa    600

cagaactcag aatcagtccg gaagtgccca aaacaaggac ttgctgttta gccgggggtc    660

tccagctggc atgtctgttc agcccaaaaa ctggctacct ggaccctgtt accggcagca    720

gcgcgtttct aaaacaaaaa cagacaacaa caacagcaac tttacctgga ctggtgcttc    780

aaaatataac cttaatgggc gtgaatctat aatcaaccct ggcactgcta tggcctcaca    840

caaagacgac gaagacaagt tctttcccat gagcggtgtc atgatttttg gaaa          894
```

```
<210> SEQ ID NO 21
<211> LENGTH: 187
<212> TYPE: DNA
<213> ORGANISM: Artificial Sequence
<220> FEATURE:
<223> OTHER INFORMATION: Synthetic Construct

<400> SEQUENCE: 21

atgggccttg cccacctata acaaccacct ctacaagcaa atctccagtg cttcaggggc     60

cagcaacgac aaccactact tcggctacag cacgtgaatc tataatcaac cctggcactg    120

ctatggcctc acacaaagac gacgaagaca agttctttcc catgagcggt gtcatgattt    180

ttggaaa                                                               187
```

```
<210> SEQ ID NO 22
<211> LENGTH: 2208
<212> TYPE: DNA
<213> ORGANISM: Artificial Sequence
<220> FEATURE:
<223> OTHER INFORMATION: Synthetic Construct

<400> SEQUENCE: 22

atggctgccg atggttatct tccagattgg ctcgaggaca ctctctctga aggaataaga     60

cagtggtgga agctcaaacc tggcccacca ccaccaaagc ccgcagagcg gcataaggac    120

gacagcaggg gtcttgtgct tcctgggtac aagtacctcg gacccttcaa cggactcgac    180

aagggagagc cggtcaacga ggcagacgcc gcggccctcg agcacgacaa agcctacgac    240

cggcagctcg acagcggaga caacccgtac ctcaagtaca accacgccga cgcggagttt    300

caggagcgcc ttaaagaaga tacgtctttt gggggcaacc tcggacgagc agtcttccag    360

gcgaaaaaga gggttcttga acctctgggc ctggttgagg aacctgttaa gacggctccg    420

ggaaaaaaga ggccggtaga gcactctcct gtggagccag actcctcctc gggaaccgga    480

aaggcgggcc agcagcctgc aagaaaaaga ttgaattttg gtcagactgg agacgcagac    540

tcagtacctg acccccagcc tctcggacag ccaccagcag ccccctctgg tctgggaact    600

aatacgatgg ctacaggcag tggcgcacca atggcagaca ataacgaggg cgccgacgga    660

gtgggtaatt cctcgggaaa ttggcattgc gattccacat ggatgggcga cagagtcatc    720

accaccagca cccgaacctg ggccctgccc acctacaaca accacctcta caaacaaatt    780

tccagccaat caggagcctc gaacgacaat cactactttg gctacagcac cccttggggg    840

tattttgact tcaacagatt ccactgccac ttttcaccac gtgactggca aagactcatc    900

aacaacaact ggggattccg acccaagaga ctcaacttca agctctttaa cattcaagtc    960

aaagaggtca cgcagaatga cggtacgacg acgattgcca ataaccttac cagcacggtt   1020
```

```
caggtgttta ctgactcgga gtaccagctc ccgtacgtcc tcggctcggc gcatcaagga   1080

tgcctcccgc cgttcccagc agacgtcttc atggtgccac agtatggata cctcaccctg   1140

aacaacggga gtcaggcagt aggacgctct tcattttact gcctggagta ctttccttct   1200

cagatgctgc gtaccggaaa caactttacc ttcagctaca cttttgagga cgttcctttc   1260

cacagcagct acgctcacag ccagagtctg gaccgtctca tgaatcctct catcgaccag   1320

tacctgtatt acttgagcag aacaaacact ccaagtggaa ccaccacgca gtcaaggctt   1380

cagttttctc aggccggagc gagtgacatt cgggaccagt ctaggaactg gcttcctgga   1440

ccctgttacc gccagcagcg agtatcaaag acatctgcgg ataacaacaa cagtgaatac   1500

tcgtggactg gagctaccaa gtaccacctc aatggcagag actctctggt gaatccgggc   1560

ccggccatgg caagccacaa ggacgatgaa gaaaagtttt ttcctcagag cggggttctc   1620

atctttggga agcaaggctc agagaaaaca aatgtggaca ttgaaaaggt catgattaca   1680

gacgaagagg aaatcaggac aaccaatccc gtggctacgg agcagtatgg ttctgtatct   1740

accaacctcc agagaggcaa cagacaagca gctaccgcag atgtcaacac acaaggcgtt   1800

cttccaggca tggtctggca ggacagagat gtgtaccttc aggggcccat ctgggcaaag   1860

attccacaca cggacggaca ttttcacccc tctcccctca tgggtggatt cggacttaaa   1920

caccctcctc cacagattct catcaagaac accccggtac ctgcgaatcc ttcgaccacc   1980

ttcagtgcgg caaagtttgc ttccttcatc acacagtact ccacgggaca ggtcagcgtg   2040

gagatcgagt gggagctgca gaaggaaaac agcaaacgct ggaatcccga aattcagtac   2100

acttccaact acaacaagtc tgttaatgtg gactttactg tggacactaa tggcgtgtat   2160

tcagagcctc gccccattgg caccagatac ctgactcgta atctgtaa                2208
```

<210> SEQ ID NO 23
<211> LENGTH: 6001
<212> TYPE: DNA
<213> ORGANISM: Artificial Sequence
<220> FEATURE:
<223> OTHER INFORMATION: Synthetic construct

<400> SEQUENCE: 23

```
gggggggggg ggggggg ttg gccactccct ctctgcgcgc tcgctcgctc actgaggccg     60

ggcgaccaaa ggtcgcccga cgcccgggct ttgcccgggc ggcctcagtg agcgagcgag    120

cgcgcagaga gggagtggcc aactccatca ctaggggttc ctagatcttc aatattggcc    180

attagccata ttattcattg gttatatagc ataaatcaat attggatatt ggccattgca    240

tacgttgtat ctatatcata atatgtacat ttatattggc tcatgtccaa tatgaccgcc    300

atgttggcat tgattattga ctagttatta atagtaatca attacggggt cattagttca    360

tagcccatat atggagttcc gcgttacata acttacggta aatggcccgc ctggctgacc    420

gcccaacgac ccccgcccat tgacgtcaat aatgacgtat gttcccatag taacgccaat    480

agggactttc cattgacgtc aatgggtgga gtatttacgg taaactgccc acttggcagt    540

acatcaagtg tatcatatgc caagtccgcc ccctattgac gtcaatgacg gtaaatggcc    600

cgcctggcat tatgcccagt acatgacctt acgggacttt cctacttggc agtacatcta    660

cgtattagtc atcgctatta ccatggtcga ggtgagcccc acgttctgct tcactctccc    720

catctccccc ccctccccac ccccaatttt gtatttattt atttttttaat tattttgtgc    780

agcgatgggg gcgggggggg ggggggggcg cgcgccaggc ggggcggggc ggggcgaggg    840
```

-continued gcggggcggg gcgaggcgga gaggtgcggc ggcagccaat cagagcggcg cgctccgaaa 900
gtttcctttt atggcgaggc ggcggcggcg gcggccctat aaaaagcgaa gcgcgcggcg 960
ggcgggagtc gctgcgacgc tgccttcgcc ccgtgccccg ctccgccgcc gcctcgcgcc 1020
gcccgccccg gctctgactg accgcgttac tcccacaggt gagcgggcgg gacggccctt 1080
ctcctccggg ctgtaattag ctgagcaaga ggtaagggtt taagggatgg ttggttggtg 1140
gggtattaat gtttaattac ctggagcacc tgcctgaaat cacttttttt caggttggac 1200
cggtcgccac catggaagac gccaaaaaca taaagaaagg cccggcgcca ttctatccgc 1260
tggaagatgg aaccgctgga gagcaactgc ataaggctat gaagagatac gccctggttc 1320
ctggaacaat tgcttttaca gatgcacata tcgaggtgga catcacttac gctgagtact 1380
tcgaaatgtc cgttcggttg gcagaagcta tgaaacgata tgggctgaat acaaatcaca 1440
gaatcgtcgt atgcagtgaa aactctcttc aattctttat gccggtgttg ggcgcgttat 1500
ttatcggagt tgcagttgcg cccgcgaacg acatttataa tgaacgtgaa ttgctcaaca 1560
gtatgggcat ttcgcagcct accgtggtgt tcgtttccaa aaaggggttg caaaaaattt 1620
tgaacgtgca aaaaaagctc ccaatcatcc aaaaaattat tatcatggat tctaaaacgg 1680
attaccaggg atttcagtcg atgtacacgt tcgtcacatc tcatctacct cccggtttta 1740
atgaatacga ttttgtgcca gagtccttcg atagggacaa gacaattgca ctgatcatga 1800
actcctctgg atctactggt ctgcctaaag gtgtcgctct gcctcataga actgcctgcg 1860
tgagattctc gcatgccaga gatcctattt ttggcaatca aatcattccg gatactgcga 1920
ttttaagtgt tgttccattc catcacggtt ttggaatgtt tactacactc ggatatttga 1980
tatgtggatt tcgagtcgtc ttaatgtata gatttgaaga agagctgttt ctgaggagcc 2040
ttcaggatta caagattcaa agtgcgctgc tggtgccaac cctattctcc ttcttcgcca 2100
aaagcactct gattgacaaa tacgatttat ctaatttaca cgaaattgct tctggtggcg 2160
ctcccctctc taaggaagtc ggggaagcgg ttgccaagag gttccatctg ccaggtatca 2220
ggcaaggata tgggctcact gagactacat cagctattct gattacaccc gagggggatg 2280
ataaaccggg cgcggtcggt aaagttgttc cattttttga agcgaaggtt gtggatctgg 2340
ataccgggaa aacgctgggc gttaatcaaa gaggcgaact gtgtgtgaga ggtcctatga 2400
ttatgtccgg ttatgtaaac aatccggaag cgaccaacgc cttgattgac aaggatggat 2460
ggctacattc tggagacata gcttactggg acgaagacga acacttcttc atcgttgacc 2520
gcctgaagtc tctgattaag tacaaaggct atcaggtggc tcccgctgaa ttggaatcca 2580
tcttgctcca acaccccaac atcttcgacg caggtgtcgc aggtcttccc gacgatgacg 2640
ccggtgaact tcccgccgcc gttgttgttt tggagcacgg aaagacgatg acggaaaaag 2700
agatcgtgga ttacgtcgcc agtcaagtaa caaccgcgaa aaagttgcgc ggaggagttg 2760
tgtttgtgga cgaagtaccg aaaggtctta ccggaaaact cgacgcaaga aaaatcagag 2820
agatcctcat aaaggccaag aagggcggaa agatcgccgt gtaagcggcc gcggggatcc 2880
agacatgata agatacattg atgagtttgg acaaaccaca actagaatgc agtgaaaaaa 2940
atgctttatt tgtgaaattt gtgatgctat tgctttattt gtaaccatta taagctgcaa 3000
taaacaagtt aacaacaaca attgcattca ttttatgttt caggttcagg gggagatgtg 3060
ggaggttttt taaagcaagt aaaacctcta caaatgtggt aaaatcgata aggatctagg 3120
aacccctagt gatggagttg gccactccct ctctgcgcgc tcgctcgctc actgaggccg 3180
cccgggcaaa gcccgggcgt cgggcgacct ttggtcgccc ggcctcagtg agcgagcgag 3240

-continued cgcgcagaga gggagtggcc aacccccccc cccccccccc tgcagcctgg cgtaatagcg 3300
aagaggcccg caccgatcgc ccttcccaac agttgcgtag cctgaatggc gaatggcgcg 3360
acgcgccctg tagcggcgca ttaagcgcgg cgggtgtggt ggttacgcgc agcgtgaccg 3420
ctacacttgc cagcgcccta gcgcccgctc ctttcgcttt cttcccttcc tttctcgcca 3480
cgttcgccgg ctttccccgt caagctctaa atcgggggct ccctttaggg ttccgattta 3540
gtgctttacg gcacctcgac cccaaaaaac ttgattaggg tgatggttca cgtagtgggc 3600
catcgccctg atagacggtt tttcgccctt tgacgttgga gtccacgttc tttaatagtg 3660
gactcttgtt ccaaactgga acaacactca accctatctc ggtctattct tttgatttat 3720
aagggatttt gccgatttcg gcctattggt taaaaaatga gctgatttaa caaaaattta 3780
acgcgaattt taacaaaata ttaacgttta caatttcctg atgcgctatt ttctccttac 3840
gcatctgtgc ggtatttcac accgcatatg gtgcactctc agtacaatct gctctgatgc 3900
cgcatagtta agccagcccc gacacccgcc aacacccgct gacgcgccct gacgggcttg 3960
tctgctcccg gcatccgctt acagacaagc tgtgaccgtc tccgggagct gcatgtgtca 4020
gaggttttca ccgtcatcac cgaaacgcgc gagacgaaag ggcctcgtga tacgcctatt 4080
tttataggtt aatgtcatga taataatggt ttcttagacg tcaggtggca cttttcgggg 4140
aaatgtgcgc ggaaccccta tttgtttatt tttctaaata ctttcaaata tgtatccgct 4200
catgagacaa taaccctgat aaatgcttca ataatattga aaaaggaaga gtatgagtat 4260
tcaacatttc cgtgtcgccc ttattccctt ttttgcggca ttttgccttc ctgtttttgc 4320
tcacccagaa acgctggtga aagtaaaaga tgctgaagat cagttgggtg cacgagtggg 4380
ttacatcgaa ctggatctca acagcggtaa gatccttgag agttttcgcc ccgaagaacg 4440
ttttccaatg atgagcactt ttaaagttct gctatgtggc gcggtattat cccgtattga 4500
cgccgggcaa gagcaactcg gtcgccgcat acactattct cagaatgact tggttgagta 4560
ctcaccagtc acagaaaagc atcttacgga tggcatgaca gtaagagaat tatgcagtgc 4620
tgccataacc atgagtgata acactgcggc caacttactt ctgacaacga tcggaggacc 4680
gaaggagcta accgcttttt tgcacaacat gggggatcat gtaactcgcc ttgatcgttg 4740
ggaaccggag ctgaatgaag ccataccaaa cgacgagcgt gacaccacga tgcctgtagc 4800
aatggcaaca acgttgcgca aactattaac tggcgaacta cttactctag cttcccggca 4860
acaattaata gactggatgg aggcggataa agttgcagga ccacttctgc gctcggccct 4920
tccggctggc tggtttattg cggataaatc tggagccggt gagcgtgggt ctcgcggtat 4980
cattgcagca ctggggccag atggtaagcc ctcccgtatc gtagttatct acacgacggg 5040
gagtcaggca actatggatg aacgaaatag acagatcgct gagataggtg cctcactgat 5100
taagcattgg taactgtcag accaagttta ctcatatata ctttagattg atttaaaact 5160
tcatttttaa tttaaaagga tctaggtgaa gatccttttt gataatctca tgaccaaaat 5220
cccttaacgt gagttttcgt tccactgagc gtcagacccc gtagaaaaga tcaaaggatc 5280
ttcttgagat cctttttttc tgcgcgtaat ctgctgcttg caaacaaaaa aaccaccgct 5340
accagcggtg gtttgtttgc cggatcaaga gctaccaact ctttttccga aggtaactgg 5400
cttcagcaga gcgcagatac caaatactgt ccttctagtg tagccgtagt taggccacca 5460
cttcaagaac tctgtagcac cgcctacata cctcgctctg ctaatcctgt taccagtggc 5520
tgctgccagt ggcgataagt cgtgtcttac cgggttggac tcaagacgat agttaccgga 5580

-continued

```
taaggcgcag cggtcgggct gaacgggggg ttcgtgcaca cagcccagct tggagcgaac   5640

gacctacacc gaactgagat acctacagcg tgagcattga gaaagcgcca cgcttcccga   5700

agggagaaag gcggacaggt atccggtaag cggcagggtc ggaacaggag agcgcacgag   5760

ggagcttcca gggggaaacg cctggtatct ttatagtcct gtcgggtttc gccacctctg   5820

acttgagcgt cgatttttgt gatgctcgtc aggggggcgg agcctatgga aaaacgccag   5880

caacgcggcc tttttacggt tcctggcctt ttgctggcct tttgctcaca tgttctttcc   5940

tgcgttatcc cctgattctg tggataaccg tattaccgcc tttgagtgag ctgataccgc   6000

t                                                                   6001


<210> SEQ ID NO 24
<211> LENGTH: 6401
<212> TYPE: DNA
<213> ORGANISM: Artificial Sequence
<220> FEATURE:
<223> OTHER INFORMATION: Synthetic construct

<400> SEQUENCE: 24

gggggggggg ggggggttg gccactccct ctctgcgcgc tcgctcgctc actgaggccg     60

ggcgaccaaa ggtcgcccga cgcccgggct ttgcccgggc ggcctcagtg agcgagcgag    120

cgcgcagaga gggagtggcc aactccatca ctaggggttc ctagatcttc aatattggcc    180

attagccata ttattcattg gttatatagc ataaatcaat attggatatt ggccattgca    240

tacgttgtat ctatatcata atatgtacat ttatattggc tcatgtccaa tatgaccgcc    300

atgttggcat tgattattga ctagttatta atagtaatca attacggggt cattagttca    360

tagcccatat atggagttcc gcgttacata acttacggta aatggcccgc ctggctgacc    420

gcccaacgac ccccgcccat tgacgtcaat aatgacgtat gttcccatag taacgccaat    480

agggactttc cattgacgtc aatgggtgga gtatttacgg taaactgccc acttggcagt    540

acatcaagtg tatcatatgc caagtccgcc ccctattgac gtcaatgacg gtaaatggcc    600

cgcctggcat tatgcccagt acatgacctt acgggacttt cctacttggc agtacatcta    660

cgtattagtc atcgctatta ccatggtcga ggtgagcccc acgttctgct tcactctccc    720

catctccccc ccctccccac ccccaatttt gtatttattt atttttaat tattttgtgc    780

agcgatgggg gcgggggggg gggggggcg cgcgccaggc ggggcggggc ggggcgaggg    840

gcggggcggg gcgaggcgga gaggtgcggc ggcagccaat cagagcggcg cgctccgaaa    900

gtttcctttt atggcgaggc ggcggcggcg gcggccctat aaaaagcgaa gcgcgcggcg    960

ggcgggagtc gctgcgacgc tgccttcgcc ccgtgccccg ctccgccgcc gcctcgcgcc   1020

gcccgccccg gctctgactg accgcgttac tcccacaggt gagcgggcgg gacggccctt   1080

ctcctccggg ctgtaattag ctgagcaaga ggtaagggtt taagggatgg ttggttggtg   1140

gggtattaat gtttaattac ctggagcacc tgcctgaaat cactttttt caggttggac   1200

cggtaccatg gtgagctact gggacaccgg cgtgctgctg tgcgccctgc tgagctgcct   1260

gctgctgacc ggcagcagca gcggcagcaa gctgaaggac cccgagctga gcctgaaggg   1320

cacccagcac atcatgcagg ccggccagac cctgcacctg cagtgccgcg gcgaggccgc   1380

ccacaagtgg agcctgcccg agatggtgag caaggagagc gagcgcctga gcatcaccaa   1440

gagcgcctgc ggccgcaacg gcaagcagtt ctgcagcacc ctgaccctga acaccgccca   1500

ggccaaccac accggcttct acagctgcaa gtacctggcc gtgcccacca gcaagaagaa   1560

ggagaccgag agcgccatct acatcttcat cagcgacacc ggccgcccct tcgtggagat   1620
```

-continued

```
gtacagcgag atccccgaga tcatccacat gaccgagggc cgcgagctgg tgatcccctg   1680
ccgcgtgacc agccccaaca tcaccgtgac cctgaagaag ttcccccctgg acaccctgat   1740
ccccgacggc aagcgcatca tctgggacag ccgcaagggc ttcatcatca gcaacgccac   1800
ctacaaggag atcggcctgc tgacctgcga ggccaccgtg aacggccacc tgtacaagac   1860
caactacctg acccaccgcc agaccaacac catcatcgac gtgcagatca gcaccccccg   1920
ccccgtgaag ctgctgcgcg gccacaccct ggtgctgaac tgcaccgcca ccaccccccct   1980
gaacacccgc gtgcagatga cctggagcta ccccgacgag aagaacaagc gcgccagcgt   2040
gcgccgccgc atcgaccaga gcaacagcca cgccaacatc ttctacagcg tgctgaccat   2100
cgacaagatg cagaacaagg acaagggcct gtacacctgc cgcgtgcgca gcggccccag   2160
cttcaagagc gtgaacacca gcgtgcacat ctacgacaag gccttcatca ccgtgaagca   2220
ccgcaagcag caggtgctgg agaccgtggc cggcaagcgc agctaccgcc tgagcatgaa   2280
ggtgaaggcc ttccccagcc ccgaggtggt gtggctgaag gacggcctgc ccgccaccga   2340
gaagagcgcc cgctacctga cccgcggcta cagcctgatc atcaaggacg tgaccgagga   2400
ggacgccggc aactacacca tcctgctgag catcaagcag agcaacgtgt tcaagaacct   2460
gaccgccacc ctgatcgtga acgtgaagcc ccagatctac gagaaggccg tgagcagctt   2520
ccccgacccc gccctgtacc ccctgggcag ccgccagatc ctgacctgca ccgcctacgg   2580
catcccccag cccaccatca agtggttctg gcacccctgc aaccacaacc acagcgaggc   2640
ccgctgcgac ttctgcagca acaacgagga gagcttcatc ctggacgccg acagcaacat   2700
gggcaaccgc atcgagagca tcacccagcg catggccatc atcgagggca agaacaagat   2760
ggccagcacc ctggtggtgg ccgacagccg catcagcggc atctacatct gcatcgccag   2820
caacaaggtg ggcaccgtgg gccgcaacat cagcttctac atcaccgacg tgcccaacgg   2880
cttccacgtg aacctggaga agatgcccac cgagggcgag gacctgaagc tgagctgcac   2940
cgtgaacaag ttcctgtacc gcgacgtgac ctggattctg ctgcgcaccg tgaacaaccg   3000
caccatgcac tacagcatca gcaagcagaa gatggccatc accaaggagc acagcatcac   3060
cctgaacctg accatcatga acgtgagcct gcaggacagc ggcacctacg cctgccgcgc   3120
ccgcaacgtg tacaccggcg aggagatcct gcagaagaag gagatcacca tccgcggcga   3180
gcactgcaac aagaaggccg tgttcagccg catcagcaag ttcaagagca cccgcaacga   3240
ctgcaccacc cagagcaacg tgaagcatta gtaaggatcc agacatgata agatacattg   3300
atgagtttgg acaaaccaca actagaatgc agtgaaaaaa atgctttatt tgtgaaattt   3360
gtgatgctat tgctttattt gtaaccatta taagctgcaa taaacaagtt aacaacaaca   3420
attgcattca ttttatgttt caggttcagg gggagatgtg ggaggttttt taaagcaagt   3480
aaaacctcta caaatgtggt aaaatcgata aggatctagg aacccctagt gatggagttg   3540
gccactccct ctctgcgcgc tcgctcgctc actgaggccg cccgggcaaa gcccgggcgt   3600
cgggcgacct ttggtcgccc ggcctcagtg agcgagcgag cgcgcagaga gggagtggcc   3660
aacccccccc cccccccccc tgcagcctgg cgtaatagcg aagaggcccg caccgatcgc   3720
ccttcccaac agttgcgtag cctgaatggc gaatggcgcg acgcgccctg tagcggcgca   3780
ttaagcgcgg cgggtgtggt ggttacgcgc agcgtgaccg ctacacttgc cagcgcccta   3840
gcgcccgctc ctttcgcttt cttcccttcc tttctcgcca cgttcgccgg ctttccccgt   3900
caagctctaa atcgggggct ccctttaggg ttccgattta gtgctttacg gcacctcgac   3960
```

-continued

```
cccaaaaaac ttgattaggg tgatggttca cgtagtgggc catcgccctg atagacggtt   4020
tttcgccctt tgacgttgga gtccacgttc tttaatagtg gactcttgtt ccaaactgga   4080
acaacactca accctatctc ggtctattct tttgatttat aagggatttt gccgatttcg   4140
gcctattggt taaaaaatga gctgatttaa caaaaattta acgcgaattt taacaaaata   4200
ttaacgttta caatttcctg atgcgctatt ttctccttac gcatctgtgc ggtatttcac   4260
accgcatatg gtgcactctc agtacaatct gctctgatgc cgcatagtta agccagcccc   4320
gacacccgcc aacacccgct gacgcgccct gacgggcttg tctgctcccg gcatccgctt   4380
acagacaagc tgtgaccgtc tccgggagct gcatgtgtca gaggttttca ccgtcatcac   4440
cgaaacgcgc gagacgaaag ggcctcgtga tacgcctatt tttataggtt aatgtcatga   4500
taataatggt ttcttagacg tcaggtggca cttttcgggg aaatgtgcgc ggaacccta   4560
tttgtttatt tttctaaata ctttcaaata tgtatccgct catgagacaa taaccctgat   4620
aaatgcttca ataatattga aaaaggaaga gtatgagtat tcaacatttc cgtgtcgccc   4680
ttattccctt ttttgcggca ttttgccttc ctgtttttgc tcacccagaa acgctggtga   4740
aagtaaaaga tgctgaagat cagttgggtg cacgagtggg ttacatcgaa ctggatctca   4800
acagcggtaa gatccttgag agttttcgcc ccgaagaacg ttttccaatg atgagcactt   4860
ttaaagttct gctatgtggc gcggtattat cccgtattga cgccgggcaa gagcaactcg   4920
gtcgccgcat acactattct cagaatgact tggttgagta ctcaccagtc acagaaaagc   4980
atcttacgga tggcatgaca gtaagagaat tatgcagtgc tgccataacc atgagtgata   5040
acactgcggc caacttactt ctgacaacga tcggaggacc gaaggagcta accgcttttt   5100
tgcacaacat gggggatcat gtaactcgcc ttgatcgttg ggaaccggag ctgaatgaag   5160
ccataccaaa cgacgagcgt gacaccacga tgcctgtagc aatggcaaca acgttgcgca   5220
aactattaac tggcgaacta cttactctag cttcccggca acaattaata gactggatgg   5280
aggcggataa agttgcagga ccacttctgc gctcggccct tccggctggc tggtttattg   5340
cggataaatc tggagccggt gagcgtgggt ctcgcggtat cattgcagca ctggggccag   5400
atggtaagcc ctcccgtatc gtagttatct acacgacggg gagtcaggca actatggatg   5460
aacgaaatag acagatcgct gagataggtg cctcactgat taagcattgg taactgtcag   5520
accaagttta ctcatatata ctttagattg atttaaaact tcatttttaa tttaaaagga   5580
tctaggtgaa gatccttttt gataatctca tgaccaaaat cccttaacgt gagttttcgt   5640
tccactgagc gtcagacccc gtagaaaaga tcaaaggatc ttcttgagat cctttttttc   5700
tgcgcgtaat ctgctgcttg caaacaaaaa aaccaccgct accagcggtg gtttgtttgc   5760
cggatcaaga gctaccaact ctttttccga aggtaactgg cttcagcaga gcgcagatac   5820
caaatactgt ccttctagtg tagccgtagt taggccacca cttcaagaac tctgtagcac   5880
cgcctacata cctcgctctg ctaatcctgt taccagtggc tgctgccagt ggcgataagt   5940
cgtgtcttac cgggttggac tcaagacgat agttaccgga taaggcgcag cggtcgggct   6000
gaacgggggg ttcgtgcaca cagcccagct tggagcgaac gacctacacc gaactgagat   6060
acctacagcg tgagcattga gaaagcgcca cgcttcccga agggagaaag gcggacaggt   6120
atccggtaag cggcagggtc ggaacaggag agcgcacgag ggagcttcca gggggaaacg   6180
cctggtatct ttatagtcct gtcgggtttc gccacctctg acttgagcgt cgatttttgt   6240
gatgctcgtc aggggggcgg agcctatgga aaaacgccag caacgcggcc tttttacggt   6300
tcctggcctt ttgctggcct tttgctcaca tgttctttcc tgcgttatcc cctgattctg   6360
```

tggataaccg tattaccgcc tttgagtgag ctgataccgc t 6401

<210> SEQ ID NO 25
<211> LENGTH: 6401
<212> TYPE: DNA
<213> ORGANISM: Artificial Sequence
<220> FEATURE:
<223> OTHER INFORMATION: Synthetic Construct

<400> SEQUENCE: 25
gggggggggg ggggggttg gccactccct ctctgcgcgc tcgctcgctc actgaggccg 60
ggcgaccaaa ggtcgcccga cgcccgggct ttgcccgggc ggcctcagtg agcgagcgag 120
cgcgcagaga gggagtggcc aactccatca ctaggggttc ctagatcttc aatattggcc 180
attagccata ttattcattg gttatatagc ataaatcaat attggatatt ggccattgca 240
tacgttgtat ctatatcata atatgtacat ttatattggc tcatgtccaa tatgaccgcc 300
atgttggcat tgattattga ctagttatta atagtaatca attacggggt cattagttca 360
tagcccatat atggagttcc gcgttacata acttacggta aatggcccgc ctggctgacc 420
gcccaacgac ccccgcccat tgacgtcaat aatgacgtat gttcccatag taacgccaat 480
agggactttc cattgacgtc aatgggtgga gtatttacgg taaactgccc acttggcagt 540
acatcaagtg tatcatatgc caagtccgcc ccctattgac gtcaatgacg gtaaatggcc 600
cgcctggcat tatgcccagt acatgacctt acgggacttt cctacttggc agtacatcta 660
cgtattagtc atcgctatta ccatggtcga ggtgagcccc acgttctgct tcactctccc 720
catctccccc ccctccccac ccccaatttt gtatttattt atttttttaat tattttgtgc 780 agcgatgggg gcgggggggg gggggggcg cgcgccaggc ggggcggggc ggggcgaggg 840
gcggggcggg gcgaggcgga gaggtgcggc ggcagccaat cagagcggcg cgctccgaaa 900
gtttcctttt atggcgaggc ggcggcggcg gcggccctat aaaaagcgaa gcgcgcggcg 960
ggcgggagtc gctgcgacgc tgccttcgcc ccgtgccccg ctccgccgcc gcctcgcgcc 1020
gcccgccccg gctctgactg accgcgttac tcccacaggt gagcgggcgg gacggccctt 1080
ctcctccggg ctgtaattag ctgagcaaga ggtaagggtt taagggatgg ttggttggtg 1140
gggtattaat gtttaattac ctggagcacc tgcctgaaat cacttttttt caggttggac 1200
cggtaccatg gtctcatact gggatactgg ggtcctgctg tgcgccctgc tgagttgtct 1260
gctgctgact gggagttcta gcgggtccaa gctgaaagac ccagagctga gcctgaaggg 1320
gactcagcac attatgcagg ctggacagac cctgcacctc cagtgccgag gagaggcagc 1380
tcacaaatgg tccctgcccg aaatggtgtc caaggagtct gaaagactga gtatcaccaa 1440
atcagcatgc ggcaggaacg ggaagcagtt ctgttccact ctgaccctga acacagcaca 1500
ggccaatcat accggcttct actcttgcaa gtatctggcc gtgcccacca gtaagaaaaa 1560
ggagacagaa tcagctatct atattttcat cagcgatacc ggacggccct ttgtggagat 1620
gtacagtgag atccctgaaa tcattcacat gactgagggc agggagctgg tcatcccatg 1680
tcgcgtcacc tcacccaata tcacagtgac tctgaaaaag ttccctctgg acaccctgat 1740
tccagatgga aaacgcatca tttgggactc ccgaaagggc tttatcatct ctaacgcaac 1800
atacaaggag atcgggctgc tgacctgcga agccacagtg aacggacatc tgtacaagac 1860
taattatctg acccacagac agaccaatac aatcattgat gtgcagatca gcaccccacg 1920
gcctgtcaag ctgctgagag gacatactct ggtcctgaac tgtaccgcca ccacacctct 1980

-continued

```
gaataccaga gtgcagatga catggtctta cccagacgag aaaaacaaga gggctagtgt   2040
ccggagaagg atcgaccagt ctaacagtca cgcaaatatt ttctatagcg tgctgacaat   2100
cgacaagatg cagaacaaag ataagggcct gtacacttgt cgcgtgcgaa gtgggccttc   2160
attcaaaagc gtgaatactt ccgtccatat ctatgacaaa gccttcatca ccgtgaaaca   2220
ccggaagcag caggtgctgg agacagtcgc cgggaaaagg agctaccgcc tgtccatgaa   2280
agtgaaggct tttccatccc ccgaggtggt ctggctgaaa gatggcctgc cagccacaga   2340
aaagagcgcc cgatacctga ctcgggggta ttccctgatc attaaggacg tgaccgagga   2400
agatgcagga aactacacaa tcctgctgag catcaagcag agtaacgtgt tcaagaatct   2460
gactgccacc ctgattgtga atgtcaaacc ccagatctac gagaaggccg tgagcagctt   2520
ccctgaccca gcactgtatc ctctgggcag ccggcagatc ctgacatgca ctgcctacgg   2580
catcccccag cctaccatta agtggttctg gcatccttgt aaccacaatc atagtgaagc   2640
aaggtgcgat ttctgttcca acaatgagga atcttttatc ctggacgccg atagtaacat   2700
gggcaatcga atcgagtcaa ttacccagcg gatggctatc attgaaggga aaaacaagat   2760
ggcatctaca ctggtggtcg ccgactcccg catctctggc atctacatct gcattgcctc   2820
aaacaaagtg ggaacagtcg gccggaatat cagcttctac attactgatg tgccaaacgg   2880
atttcacgtc aatctggaga agatgcccac cgagggcgaa gacctgaaac tgtcttgtac   2940
agtgaataag ttcctgtata gggatgtcac ttggattctg ctgagaactg tgaacaatag   3000
gaccatgcat tactcaatca gcaaacagaa gatggctatc accaaggaac acagcattac   3060
actgaacctg actatcatga acgtgagcct ccaggacagc gggacctacg cttgccgggc   3120
aagaaacgtg tatacaggag aggaaatcct ccagaagaag gagatcacaa ttcgcggcga   3180
acactgtaac aagaaggccg tgtttagccg aatctccaag ttcaagtcaa ccaggaatga   3240
ttgtactacc cagtcaaatg tcaagcacta gtaaggatcc agacatgata agatacattg   3300
atgagtttgg acaaaccaca actagaatgc agtgaaaaaa atgctttatt tgtgaaattt   3360
gtgatgctat tgctttattt gtaaccatta taagctgcaa taaacaagtt aacaacaaca   3420
attgcattca ttttatgttt caggttcagg gggagatgtg ggaggttttt taaagcaagt   3480
aaaacctcta caaatgtggt aaaatcgata aggatctagg aacccctagt gatggagttg   3540
gccactccct ctctgcgcgc tcgctcgctc actgaggccg cccgggcaaa gcccgggcgt   3600
cgggcgacct ttggtcgccc ggcctcagtg agcgagcgag cgcgcagaga gggagtggcc   3660
aacccccccc cccccccccc tgcagcctgg cgtaatagcg aagaggcccg caccgatcgc   3720
ccttcccaac agttgcgtag cctgaatggc gaatggcgcg acgcgccctg tagcggcgca   3780
ttaagcgcgg cgggtgtggt ggttacgcgc agcgtgaccg ctacacttgc cagcgcccta   3840
gcgcccgctc ctttcgcttt cttcccttcc tttctcgcca cgttcgccgg ctttccccgt   3900
caagctctaa atcgggggct ccctttaggg ttccgattta gtgctttacg gcacctcgac   3960
cccaaaaaac ttgattaggg tgatggttca cgtagtgggc catcgccctg atagacggtt   4020
tttcgccctt tgacgttgga gtccacgttc tttaatagtg gactcttgtt ccaaactgga   4080
acaacactca accctatctc ggtctattct tttgatttat aagggatttt gccgatttcg   4140
gcctattggt taaaaaatga gctgatttaa caaaaattta acgcgaattt taacaaaata   4200
ttaacgttta caatttcctg atgcgctatt ttctccttac gcatctgtgc ggtatttcac   4260
accgcatatg gtgcactctc agtacaatct gctctgatgc cgcatagtta agccagcccc   4320
gacacccgcc aacacccgct gacgcgccct gacgggcttg tctgctcccg gcatccgctt   4380
```

-continued acagacaagc tgtgaccgtc tccgggagct gcatgtgtca gaggttttca ccgtcatcac 4440
cgaaacgcgc gagacgaaag ggcctcgtga tacgcctatt tttataggtt aatgtcatga 4500
taataatggt ttcttagacg tcaggtggca cttttcgggg aaatgtgcgc ggaaccccta 4560
tttgtttatt tttctaaata cattcaaata tgtatccgct catgagacaa taaccctgat 4620
aaatgcttca ataatattga aaaaggaaga gtatgagtat tcaacatttc cgtgtcgccc 4680
ttattccctt ttttgcggca ttttgccttc ctgtttttgc tcacccagaa acgctggtga 4740
aagtaaaaga tgctgaagat cagttgggtg cacgagtggg ttacatcgaa ctggatctca 4800
acagcggtaa gatccttgag agttttcgcc ccgaagaacg ttttccaatg atgagcactt 4860
ttaaagttct gctatgtggc gcggtattat cccgtattga cgccgggcaa gagcaactcg 4920
gtcgccgcat acactattct cagaatgact tggttgagta ctcaccagtc acagaaaagc 4980
atcttacgga tggcatgaca gtaagagaat tatgcagtgc tgccataacc atgagtgata 5040
acactgcggc caacttactt ctgacaacga tcggaggacc gaaggagcta accgcttttt 5100
tgcacaacat gggggatcat gtaactcgcc ttgatcgttg ggaaccggag ctgaatgaag 5160
ccataccaaa cgacgagcgt gacaccacga tgcctgtagc aatggcaaca acgttgcgca 5220
aactattaac tggcgaacta cttactctag cttcccggca acaattaata gactggatgg 5280
aggcggataa agttgcagga ccacttctgc gctcggccct tccggctggc tggtttattg 5340
cggataaatc tggagccggt gagcgtgggt ctcgcggtat cattgcagca ctggggccag 5400
atggtaagcc ctcccgtatc gtagttatct acacgacggg gagtcaggca actatggatg 5460
aacgaaatag acagatcgct gagataggtg cctcactgat taagcattgg taactgtcag 5520
accaagttta ctcatatata ctttagattg atttaaaact tcatttttaa tttaaaagga 5580
tctaggtgaa gatccttttt gataatctca tgaccaaaat cccttaacgt gagttttcgt 5640
tccactgagc gtcagacccc gtagaaaaga tcaaaggatc ttcttgagat cctttttttc 5700
tgcgcgtaat ctgctgcttg caaacaaaaa aaccaccgct accagcggtg gtttgtttgc 5760
cggatcaaga gctaccaact ctttttccga aggtaactgg cttcagcaga gcgcagatac 5820
caaatactgt ccttctagtg tagccgtagt taggccacca cttcaagaac tctgtagcac 5880
cgcctacata cctcgctctg ctaatcctgt taccagtggc tgctgccagt ggcgataagt 5940
cgtgtcttac cgggttggac tcaagacgat agttaccgga taaggcgcag cggtcgggct 6000
gaacgggggg ttcgtgcaca cagcccagct tggagcgaac gacctacacc gaactgagat 6060
acctacagcg tgagcattga gaaagcgcca cgcttcccga agggagaaag gcggacaggt 6120
atccggtaag cggcagggtc ggaacaggag agcgcacgag ggagcttcca gggggaaacg 6180
cctggtatct ttatagtcct gtcgggtttc gccacctctg acttgagcgt cgatttttgt 6240
gatgctcgtc aggggggcgg agcctatgga aaaacgccag caacgcggcc tttttacggt 6300
tcctggcctt ttgctggcct tttgctcaca tgttctttcc tgcgttatcc cctgattctg 6360
tggataaccg tattaccgcc tttgagtgag ctgataccgc t 6401

<210> SEQ ID NO 26
<211> LENGTH: 687
<212> TYPE: PRT
<213> ORGANISM: Homo sapiens

<400> SEQUENCE: 26

Met Val Ser Tyr Trp Asp Thr Gly Val Leu Leu Cys Ala Leu Leu Ser
1 5 10 15

-continued

```
Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430
```

-continued

```
Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685
```